(12) United States Patent
Khvorova et al.

(10) Patent No.: US 11,702,659 B2
(45) Date of Patent: Jul. 18, 2023

(54) OPTIMIZED ANTI-FLT1 OLIGONUCLEOTIDE COMPOUNDS FOR TREATMENT OF PREECLAMPSIA AND OTHER ANGIOGENIC DISORDERS

(71) Applicants: University of Massachusetts, Boston, MA (US); Beth Israel Deaconess Medical Center, Inc., Boston, MA (US)

(72) Inventors: Anastasia Khvorova, Westborough, MA (US); Vignesh Narayan Hariharan, Natick, MA (US); Sarah Davis, Wellesley, MA (US); Annabelle Biscans, Cambridge, MA (US); Ananth Karumanchi, Chestnut Hill, MA (US)

(73) Assignees: UNIVERSITY OF MASSACHUSETTS, Boston, MA (US); BETH ISRAEL DEACONESS MEDICAL CENTER, INC., Boston, MA (US)

( * ) Notice: Subject to any disclaimer, the term of this patent is extended or adjusted under 35 U.S.C. 154(b) by 0 days.

(21) Appl. No.: 17/846,526

(22) Filed: Jun. 22, 2022

(65) Prior Publication Data
US 2023/0078622 A1      Mar. 16, 2023

Related U.S. Application Data

(60) Provisional application No. 63/214,224, filed on Jun. 23, 2021.

(51) Int. Cl.
*C07H 21/04* (2006.01)
*C12N 15/113* (2010.01)
*A61P 7/00* (2006.01)

(52) U.S. Cl.
CPC ............ *C12N 15/113* (2013.01); *A61P 7/00* (2018.01); *C12N 2310/11* (2013.01); *C12N 2310/315* (2013.01); *C12N 2310/321* (2013.01); *C12N 2310/322* (2013.01); *C12N 2310/344* (2013.01); *C12N 2310/346* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,194,596 A | 3/1993 | Tischer et al. |
| 5,219,739 A | 6/1993 | Tischer et al. |
| 5,240,848 A | 8/1993 | Keck et al. |
| 5,328,470 A | 7/1994 | Nabel et al. |
| 5,332,671 A | 7/1994 | Ferrara et al. |
| 5,684,143 A | 11/1997 | Grayaznov et al. |
| 5,814,014 A | 9/1998 | Elsberry et al. |
| 5,858,988 A | 1/1999 | Wang |
| 6,093,180 A | 7/2000 | Elsberry et al. |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,312,900 B1 | 11/2001 | Dean et al. |
| 6,383,814 B1 | 5/2002 | Lee et al. |
| 6,447,768 B1 | 9/2002 | Van Zonneveld et al. |
| 6,471,996 B1 | 10/2002 | Sokoll et al. |
| 6,472,375 B1 | 10/2002 | Hoon et al. |
| 6,489,464 B1 | 12/2002 | Agrawal et al. |
| 7,250,496 B2 | 7/2007 | Bentwich |
| 7,459,547 B2 | 12/2008 | Zamore et al. |
| 7,691,997 B2 | 4/2010 | Khvorova et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 7,790,867 B2 | 9/2010 | Bentwich |
| 7,834,171 B2 | 11/2010 | Leake et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,501,706 B2 | 8/2013 | Yamada et al. |
| 8,507,661 B2 | 8/2013 | Manoharan et al. |
| 8,664,189 B2 | 3/2014 | Khvorova et al. |
| 8,703,731 B2 | 4/2014 | Jimenez et al. |
| 8,796,443 B2 | 8/2014 | Khvorova et al. |
| 8,815,818 B2 | 8/2014 | Samarsky et al. |

(Continued)

FOREIGN PATENT DOCUMENTS

| | | |
|---|---|---|
| CN | 101199858 A | 6/2008 |
| CN | 101365801 A | 2/2009 |

(Continued)

OTHER PUBLICATIONS

U.S. Appl. No. 15/089,319, filed Apr. 1, 2016, 2016/0355808, Dec. 8, 2016, U.S. Pat. No. 9,809,817, Nov. 7, 2017, Anastasia Khvorova, Oligonucleotide Compounds for Targeting Huntingtin mRNA.
U.S. Appl. No. 15/697,120, filed Sep. 6, 2017, 2018/0094263, Apr. 5, 2018, U.S. Pat. No. 10,435,688, Oct. 8, 2019, Anastasia Khvorova, Oligonucleotide Compounds for Targeting Huntingtin mRNA.
U.S. Appl. No. 16/263,200, filed Jan. 31, 2019, 2019/0225965, Jul. 25, 2019, U.S. Pat. No. 10,744,327, Sep. 15, 2020, Anastasia Khvorova, Oligonucleotide Compounds for Targeting Huntingtin mRNA.
U.S. Appl. No. 16/811,580, filed Mar. 6, 2020, 2020/0308584, Oct. 1, 2020, U.S. Pat. No. 11,230,713, Jan. 5, 2022, Anastasia Khvorova, Oligonucleotide Compounds for Targeting Huntingtin mRNA.

(Continued)

*Primary Examiner* — Kimberly Chong
(74) *Attorney, Agent, or Firm* — Lathrop GPM LLP; James H. Velema, Esq.; Michael J. Spellberg, Esq.

(57) ABSTRACT

This disclosure relates to novel targets for angiogenic disorders. Novel oligonucleotides are also provided. Methods of using the novel oligonucleotides for the treatment of angiogenic disorders (e.g., preeclampsia) are also provided.

30 Claims, 25 Drawing Sheets

Specification includes a Sequence Listing.

(56) References Cited

U.S. PATENT DOCUMENTS

| | | |
|---|---|---|
| 8,877,439 B2 | 11/2014 | Butora et al. |
| 8,906,874 B2 | 12/2014 | Rao et al. |
| 8,993,738 B2 | 3/2015 | Prakash et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,198,981 B2 | 12/2015 | Ambati et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 | 8/2017 | Woolf et al. |
| 9,796,756 B2 | 10/2017 | Hadwiger et al. |
| 9,809,817 B2 | 11/2017 | Khvorova et al. |
| 9,862,350 B2 | 1/2018 | Guerrero et al. |
| 9,862,952 B2 | 1/2018 | Khvorova et al. |
| 9,867,882 B2 | 1/2018 | Manoharan et al. |
| 10,087,210 B2 | 10/2018 | Prakash et al. |
| 10,435,688 B2 | 10/2019 | Khvorova et al. |
| 10,478,503 B2 | 11/2019 | Khvorova et al. |
| 10,479,992 B2 | 11/2019 | Woolf et al. |
| 10,519,451 B2 | 12/2019 | Khvorova et al. |
| 10,633,653 B2 | 4/2020 | Khvorova et al. |
| 10,774,327 B2 | 9/2020 | Khvorova et al. |
| 10,799,591 B2 | 10/2020 | Khvorova et al. |
| 10,844,377 B2 | 11/2020 | Khvorova et al. |
| 11,230,713 B2 | 1/2022 | Khvorova et al. |
| 11,279,930 B2 | 3/2022 | Khvorova et al. |
| 11,345,917 B2 | 5/2022 | Khvorova et al. |
| 11,492,619 B2 | 11/2022 | Khvorova et al. |
| 2003/0143732 A1 | 7/2003 | Fosnaugh et al. |
| 2004/0121426 A1 | 6/2004 | Hsieh |
| 2004/0198640 A1 | 10/2004 | Leake et al. |
| 2005/0096284 A1 | 5/2005 | Mcswiggen |
| 2005/0220766 A1 | 10/2005 | Amalfitano et al. |
| 2006/0009409 A1 | 1/2006 | Woolf |
| 2006/0078542 A1 | 4/2006 | Mah et al. |
| 2006/0094032 A1 | 5/2006 | Fougerolles et al. |
| 2007/0004664 A1 | 1/2007 | Mcswiggen et al. |
| 2007/0004665 A1 | 1/2007 | Mcswiggen et al. |
| 2007/0099860 A1 | 5/2007 | Sah et al. |
| 2007/0135372 A1 | 6/2007 | Maclachlan et al. |
| 2007/0160534 A1 | 7/2007 | Dennis et al. |
| 2007/0191273 A1 | 8/2007 | Ambat et al. |
| 2007/0259827 A1 | 11/2007 | Aronin et al. |
| 2008/0039415 A1 | 2/2008 | Stewart et al. |
| 2008/0108801 A1 | 5/2008 | Manoharan |
| 2008/0119427 A1 | 5/2008 | Bhat et al. |
| 2008/0188429 A1 | 8/2008 | Iyer |
| 2008/0269149 A1 | 10/2008 | Bowles et al. |
| 2009/0143322 A1 | 6/2009 | Burkoth et al. |
| 2009/0234109 A1 | 9/2009 | Han et al. |
| 2009/0306178 A1 | 12/2009 | Bhat et al. |
| 2010/0015706 A1 | 1/2010 | Quay et al. |
| 2010/0093085 A1 | 4/2010 | Yamada et al. |
| 2010/0184209 A1 | 7/2010 | Vermeulen et al. |
| 2010/0186103 A1 | 7/2010 | Gao et al. |
| 2011/0039914 A1 | 2/2011 | Pavco et al. |
| 2011/0201006 A1 | 8/2011 | Roehl et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0052487 A9 | 3/2012 | Khvorova et al. |
| 2012/0059046 A1 | 3/2012 | Woolf et al. |
| 2012/0065243 A1 | 3/2012 | Woolf et al. |
| 2012/0136039 A1 | 5/2012 | Aronin et al. |
| 2013/0065298 A1 | 3/2013 | Davidson et al. |
| 2013/0131141 A1 | 5/2013 | Khvorova et al. |
| 2013/0131142 A1 | 5/2013 | Libertine et al. |
| 2013/0178513 A1 | 7/2013 | Dobie et al. |
| 2013/0196434 A1 | 8/2013 | Maier et al. |
| 2013/0197055 A1 | 8/2013 | Kamens et al. |
| 2014/0113950 A1 | 4/2014 | Khvorova et al. |
| 2014/0288148 A1 | 9/2014 | Biegelman et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0025122 A1 | 1/2015 | Smith |
| 2015/0190525 A1 | 7/2015 | Tatro |
| 2015/0209441 A1 | 7/2015 | Carell |
| 2015/0232840 A1 | 8/2015 | Aronin et al. |
| 2015/0247142 A1 | 9/2015 | Esau et al. |
| 2015/0267200 A1 | 9/2015 | Mcswiggen et al. |
| 2015/0315584 A1 | 11/2015 | Macdonald et al. |
| 2016/0017323 A1 | 1/2016 | Prakash et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0130583 A1 | 5/2016 | Yokota et al. |
| 2016/0244765 A1 | 8/2016 | Khvorova et al. |
| 2016/0281148 A1 | 9/2016 | Greenlee et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0037456 A1 | 2/2017 | Kokoris et al. |
| 2017/0043024 A1 | 2/2017 | Khvorova et al. |
| 2017/0043204 A1 | 2/2017 | James |
| 2017/0051283 A1 | 2/2017 | Khvorova |
| 2017/0051286 A1 | 2/2017 | Smith |
| 2017/0067056 A1 | 3/2017 | Khvorova et al. |
| 2017/0189541 A1 | 7/2017 | Foster |
| 2017/0281795 A1 | 10/2017 | Geall |
| 2017/0312367 A1 | 11/2017 | Khvorova et al. |
| 2017/0327524 A1 | 11/2017 | Nanna et al. |
| 2017/0369882 A1 | 12/2017 | Khvorova et al. |
| 2018/0094263 A1 | 4/2018 | Khvorova et al. |
| 2018/0179546 A1 | 6/2018 | Khvorova et al. |
| 2018/0251764 A1 | 9/2018 | Albaek et al. |
| 2019/0002880 A1 | 1/2019 | Woolf et al. |
| 2019/0024082 A1 | 1/2019 | Khvorova et al. |
| 2019/0185855 A1 | 6/2019 | Khvorova et al. |
| 2019/0225965 A1 | 7/2019 | Khvorova et al. |
| 2019/0247507 A1 | 8/2019 | Khvorova et al. |
| 2020/0087663 A1 | 3/2020 | Aronin |
| 2020/0095580 A1 | 3/2020 | Hauptmann et al. |
| 2020/0123543 A1 | 4/2020 | Khvorova et al. |
| 2020/0165618 A1 | 5/2020 | Khvorova et al. |
| 2020/0270605 A1 | 8/2020 | Khvorova et al. |
| 2020/0308584 A1 | 10/2020 | Khvorova et al. |
| 2020/0339983 A1 | 10/2020 | Khvorova et al. |
| 2020/0385740 A1 | 12/2020 | Khvorova et al. |
| 2021/0024926 A1 | 1/2021 | Khvorova et al. |
| 2021/0071117 A9 | 3/2021 | Khvorova et al. |
| 2021/0085793 A1 | 3/2021 | Khvorova et al. |
| 2021/0115442 A1 | 4/2021 | Khvorova et al. |
| 2021/0139901 A1 | 5/2021 | Khvorova et al. |
| 2022/0010309 A1 | 1/2022 | Khvorova et al. |
| 2022/0228141 A1 | 7/2022 | Khvorova et al. |
| 2022/0251554 A1 | 8/2022 | Khvorova et al. |
| 2022/0251555 A1 | 8/2022 | Khvorova et al. |
| 2022/0364100 A1 | 11/2022 | Khvorova et al. |

FOREIGN PATENT DOCUMENTS

| | | |
|---|---|---|
| CN | 105194689 A | 12/2015 |
| EP | 1752536 A1 | 2/2007 |
| EP | 2407539 A1 | 1/2012 |
| EP | 2601204 A2 | 6/2013 |
| EP | 2853597 A1 | 4/2015 |
| EP | 3277811 A1 | 2/2018 |
| EP | 3277814 A1 | 2/2018 |
| EP | 3277815 A1 | 2/2018 |
| EP | 3408391 A1 | 12/2018 |
| EP | 3550021 A1 | 10/2019 |
| EP | 3642341 A1 | 4/2020 |
| EP | 3929293 A2 | 12/2021 |
| JP | 2001-501614 A | 2/2001 |
| JP | 2009-504782 A | 2/2009 |
| JP | 2012-502657 A | 2/2012 |
| JP | 2013-049714 A | 3/2013 |

(56) References Cited

FOREIGN PATENT DOCUMENTS

| | | |
|---|---|---|
| JP | 2015-061534 A | 4/2015 |
| JP | 2016-171815 A | 9/2016 |
| WO | WO 1998/013526 A1 | 4/1998 |
| WO | WO 2003/029459 A2 | 4/2003 |
| WO | WO 2004/008946 A2 | 1/2004 |
| WO | WO 2004/044136 A2 | 5/2004 |
| WO | WO 2004/061081 A2 | 7/2004 |
| WO | WO 2006/019430 A2 | 2/2006 |
| WO | WO 2007/022470 A2 | 2/2007 |
| WO | WO 2007/022506 A2 | 2/2007 |
| WO | WO 2007/051045 A2 | 5/2007 |
| WO | WO 2007/056153 A2 | 5/2007 |
| WO | WO 2007/091269 A2 | 8/2007 |
| WO | WO 2007/094218 A1 | 8/2007 |
| WO | WO 2007/112414 A2 | 10/2007 |
| WO | WO 2008/005562 A2 | 1/2008 |
| WO | WO 2008/049078 A1 | 4/2008 |
| WO | WO 2008/070477 A2 | 6/2008 |
| WO | WO 2008/154482 A2 | 12/2008 |
| WO | WO 2008/154482 A3 | 12/2008 |
| WO | WO 2009/002944 A1 | 12/2008 |
| WO | WO 2009/054551 A2 | 4/2009 |
| WO | WO 2009/099991 A2 | 8/2009 |
| WO | WO 2009/102427 A2 | 8/2009 |
| WO | WO 2010/008582 A2 | 1/2010 |
| WO | WO 2010/011346 A1 | 1/2010 |
| WO | WO 2010/033246 A1 | 3/2010 |
| WO | WO 2010/033247 A2 | 3/2010 |
| WO | WO 2010/033248 A2 | 3/2010 |
| WO | WO 2010/048585 A2 | 4/2010 |
| WO | WO 2010/059226 A2 | 5/2010 |
| WO | WO 2010/078536 A1 | 7/2010 |
| WO | WO 2010/090762 A1 | 8/2010 |
| WO | WO 2011/109698 A1 | 9/2011 |
| WO | WO 2011/119852 A1 | 9/2011 |
| WO | WO 2011/119871 A1 | 9/2011 |
| WO | WO 2011/119887 A1 | 9/2011 |
| WO | WO 2011/139702 A2 | 11/2011 |
| WO | WO 2012/005898 A2 | 1/2012 |
| WO | WO 2012/037254 A1 | 3/2012 |
| WO | WO 2012/078637 A2 | 6/2012 |
| WO | WO 2012/118911 A1 | 9/2012 |
| WO | WO 2012/177906 A1 | 12/2012 |
| WO | WO 2013/165816 A2 | 11/2013 |
| WO | WO 2014/009429 A1 | 1/2014 |
| WO | WO 2014/043544 A1 | 3/2014 |
| WO | WO 2014/076195 A1 | 5/2014 |
| WO | WO 2014/089313 A1 | 6/2014 |
| WO | WO 2015/025122 A1 | 2/2015 |
| WO | WO 2015/057847 A1 | 4/2015 |
| WO | WO 2015/161184 A1 | 10/2015 |
| WO | WO 2015/200078 A1 | 12/2015 |
| WO | WO 2016/028649 A1 | 2/2016 |
| WO | WO 2016/149331 A2 | 9/2016 |
| WO | WO 2016/161374 A1 | 10/2016 |
| WO | WO 2016/161378 A1 | 10/2016 |
| WO | WO 2016/161388 A1 | 10/2016 |
| WO | WO 2016/164866 A1 | 10/2016 |
| WO | WO 2016/205410 A2 | 12/2016 |
| WO | WO 2017/015555 A1 | 1/2017 |
| WO | WO 2017/024239 A1 | 2/2017 |
| WO | WO 2017/030973 A1 | 2/2017 |
| WO | WO 2017/062862 A2 | 4/2017 |
| WO | WO 2017/132669 A1 | 8/2017 |
| WO | WO 2017/174572 A1 | 10/2017 |
| WO | WO 2018/031933 A2 | 2/2018 |
| WO | WO 2018/185241 A1 | 10/2018 |
| WO | WO 2018/237245 A1 | 12/2018 |
| WO | WO 2020/033899 A1 | 2/2020 |
| WO | WO 2020/150636 A1 | 7/2020 |
| WO | WO 2021/242883 A1 | 12/2021 |

OTHER PUBLICATIONS

U.S. Appl. No. 17/536,647, filed Nov. 29, 2021, 2022/0251554, Aug. 11, 2022, Anastasia Khvorova, Oligonucleotide Compounds for Targeting Huntingtin mRNA.

U.S. Appl. No. 15/089,437, filed Apr. 1, 2016, 2016/0355826, Dec. 8, 2016, U.S. Pat. No. 9,862,952, Jan. 9, 2018, Anastasia Khvorova, Oligonucleotide Compounds for Treatment of Preeclampsia and Other Angiogenic Disorders.

U.S. Appl. No. 15/814,350, filed Nov. 15, 2017, 2018/0179546, Jun. 28, 2018, U.S. Pat. No. 10,519,451, Dec. 31, 2019, Anastasia Khvorova, Oligonucleotide Compounds for Treatment of Preeclampsia and Other Angiogenic Disorders.

U.S. Appl. No. 16/675,369, filed Nov. 6, 2019, 2020/0165618, May 28, 2020, U.S. Pat. No. 11,345,917, May 11, 2022, Anastasia Khvorova, Oligonucleotide Compounds for Treatment of Preeclampsia and Other Angiogenic Disorders.

U.S. Appl. No. 17/718,918, filed Apr. 12, 2022, 2022/0364100, Nov. 17, 2022, Anastasia Khvorova, Oligonucleotide Compounds for Treatment of Preeclampsia and Other Angiogenic Disorders.

U.S. Appl. No. 15/089,423, filed Apr. 1, 2016, 2016/0319278, Nov. 3, 2016, Anastasia Khvorova, Fully Stabilized Asymmetric Sirna.

U.S. Appl. No. 15/691,120, filed Aug. 30, 2017, 2017/0369882, Dec. 28, 2017, Anastasia Khvorova, Fully Stabilized Asymmetric Sirna.

U.S. Appl. No. 16/927,543, filed Jul. 13, 2020, 2021/0024926, Jan. 28, 2021, Anastasia Khvorova, Fully Stabilized Asymmetric Sirna.

U.S. Appl. No. 15/236,051, filed Aug. 12, 2016, 2017/0043024, Feb. 16, 2017, U.S. Pat. No. 10,633,653, Apr. 28, 2020, Anastasia Khvorova, Bioactive Conjugates for Oligonucleotide Delivery.

U.S. Appl. No. 16/812,714, filed Mar. 9, 2020, 2020/0339983, Oct. 29, 2020, Anastasia Khvorova, Bioactive Conjugates for Oligonucleotide Delivery.

U.S. Appl. No. 15/419,593, filed Jan. 30, 2017, 2017/0312367, Nov. 2, 2017, U.S. Pat. No. 10,478,503, Nov. 19, 2019, Anastasia Khvorova, Branched Oligonucleotides.

U.S. Appl. No. 16/390,712, filed Apr. 22, 2019, 2019/0247507, Aug. 15, 2019, U.S. Pat. No. 10,799,591, Oct. 13, 2020, Khvorova Anastasia, Branched Oligonucleotides.

U.S. Appl. No. 17/012,787, filed Sep. 4, 2020, 2021/0085793, Mar. 25, 2021, Anastasia Khvorova, Branched Oligonucleotides.

U.S. Appl. No. 16/322,212, filed Jan. 31, 2019, 2019/0185855, Jun. 20, 2019, Anastasia Khvorova, Conjugated Oligonucleotides.

U.S. Appl. No. 16/015,440, filed Jun. 22, 2018, 2019/0024082, Jan. 24, 2019, U.S. Pat. No. 10,844,377, Nov. 24, 2020, Anastasia Khvorova, Two-Tailed Self-Delivering Sirna.

U.S. Appl. No. 17/071,473, filed Oct. 15, 2020, 2021/0139901, May 13, 2021, Anastasia Khvorova, Two-Tailed Self-Delivering Sirna.

U.S. Appl. No. 16/537,374, filed Aug. 9, 2019, 2020/0123543, Apr. 23, 2020, Anastasia Khvorova, Modified Oligonucleotides Targeting SNPs.

U.S. Appl. No. 16/988,391, filed Aug. 7, 2020, 2021/0071177, Mar. 11, 2021, Anastasia Khvorova, Modified Oligonucleotides Targeting SNPs.

U.S. Appl. No. 16/831,470, filed Mar. 26, 2020, 2020/0385740, Dec. 10, 2020, Anastasia Khvorova, Modified Oligonucleotides with Increased Stability.

U.S. Appl. No. 17/213,852, filed Mar. 26, 2021, 20220010309, Jan. 13, 2022, Anastasia Khvorova, Synthesis of Modified Oligonucleotides with Increased Stability.

U.S. Appl. No. 16/746,555, filed Jan. 17, 2020, 2020/0270605, Aug. 27, 2020, U.S. Pat. No. 11,492,619, Nov. 8, 2022, Anastasia Khvorova, Dynamic Pharmacokinetic-Modifying Anchors.

U.S. Appl. No. 17/725,102, filed Apr. 20, 2022, 2022/0372476, Nov. 24, 2022, Anastasia Khvorova, Dynamic Pharmacokinetic-Modifying Anchors.

U.S. Appl. No. 17/792,705, filed Jul. 13, 2022, Anastasia Khvorova, Universal Dynamic Pharmacokinetic-Modifying Anchors.

U.S. Appl. No. 16/550,076, filed Aug. 23, 2019 /, 2020/0087663, Mar. 19, 2020 /, U.S. Pat. No. 11,279,930, Mar. 22, 2022, Anastasia Khvorova, O-Methyl Rich Fully Stabilized Oligonucleotides.

U.S. Appl. No. 16/999,759, filed Aug. 21, 2020 /, 2021/0115442, Apr. 22, 2021, Anastasia Khvorova, O-Methyl Rich Fully Stabilized Oligonucleotides.

(56) References Cited

OTHER PUBLICATIONS

U.S. Appl. No. 17/580,269, filed Jan. 20, 2022 /, 2022/0251555, Aug. 11, 2022, Anastasia Khvorova, O-Methyl Rich Fully Stabilized Oligonucleotides.

U.S. Appl. No. 17/022,678, filed Sep. 16, 2020, 2021/0108200, Apr. 15, 2021, Anastasia Khvorova, Branched Lipid Conjugates of siRNA for Specific Tissue Delivery.

U.S. Appl. No. 17/331,146, filed May 26, 2021, 2021/0395739, Dec. 23, 2021, Anastasia Khvorova, Synthetic Oligonucleotides Having Regions of Block and Cluster Modifications.

U.S. Appl. No. 17/377,632, filed Jul. 16, 2021, 2022/0042015, Feb. 10, 2022, Anastasia Khvorova, Conjugated Oligonucleotides for Tissue Specific Delivery.

U.S. Appl. No. 17/532,636, filed Nov. 22, 2021, 2022/0228141, Jul. 21, 2022, Anastasia Khvorova, Oligonucleotides for Modulation.

Akinc et al., A Combinatorial Library of Lipid-like Materials for Delivery of RNAi Therapeutics, Nature Biotechnology, vol. 26, No. 5, 20 Pages, May 2008.

Alagia, et al., Exploring PAZ/3'-overhang Interaction to Improve siRNA Specificity. A Combined Experimental and Modeling Study, Chemical Science, vol. 9, No. 8, pp. 2074-2086, 2018.

Alexopoulou, et al., Recognition of Double-Stranded RNA and Activation of NF-κB by Toll-like receptors, Nature, vol. 413, No. 6857, pp. 732-738, Oct. 18, 2001.

Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.

Allerson et al., "Fully 2'-modified oligonucleotide duplexes with improved in vitro potency and stability compared to unmodified small interfering RNA", J Med Chem., Feb. 24, 2005, 48(4): 901-904.

Alterman, et al., Hydrophobically Modified siRNAs Silence Huntingtin mRNA in Primary Neurons and Mouse Brain, Molecular Therapy-Nucleic Acids, vol. 4, pp. e266, Dec. 1, 2015.

Alvarez-Erviti, et al., "Delivery of siRNA to the Mouse Brain by Systemic Injection of Targeted Exosomes", Nature Biotechnology, vol. 29, No. 4, pp. 341-345, Apr. 2011.

Alves, et al., Selectivity, Cooperativity, and Reciprocity in the Interactions between the σ-Opioid Receptor, Its Ligands, and G-proteins, Journal of Biological Chemistry, vol. 279 No. 43, pp. 4673-44682, Aug. 17, 2004.

Amarzguioui, et al., "Tolerance for Mutations and Chemical Modifications in a siRNA", Nucleic Acids Research, Jan. 15, 2003, 31(2): 589-595.

Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).

Ambros, et al., MicroRNAs and Other Tiny Endogenous RNAs in C. elegans, Current Biology, vol. 13, Issue 10, pp. 807-818, May 13, 2003.

Ameres, et al., Molecular Basis for Target RNA Recognition and Cleavage by Human RISC, Cell, vol. 130, Issue 1, pp. 101-112, Jul. 13, 2007.

Ämmälä, et al., Targeted Delivery of Antisense Oligonucleotides to Pancreatic β-cells, Science Advances, vol. 4, No. 10, eaat3386, pp. 1-11, Oct. 17, 2018.

Anderson, et al., Experimental Validation of the Importance of Seed Complement Frequency to siRNA Specificity, RNA, vol. 14, No. 5, pp. 853-861, Mar. 26, 2008.

Anderson, et al., Identifying siRNA-Induced Off-Targets by Microarray Analysis, Methods in Molecular Biology, vol. 442, pp. 45-63, 2008.

Atwell, et al., Stable Heterodimers From Remodeling the Domain Interface of a Homodimer Using a Phage Display Library, Journal of Molecular Biology, vol. 270, Issue 1, pp. 26-35, Jul. 4, 1997.

Aubuchon, et al., "Preeclampsia: Animal Models fora Human Cure", Proceedings of the National Academy of Sciences, vol. 108, No. 4, pp. 1197-1198, Jan. 25, 2011.

Aureli, et al., GM1 Ganglioside: Past Studies and Future Potential, Molecular Neurobiology, vol. 53, Issue 3, pp. 1824-1842, Apr. 2016.

Avino, et al., Branched RNA: A New Architecture for RNA Interference, Journal of Nucleic Acids, Article IC586935, 7 pages, Mar. 6, 2011.

Bagella, et al., Cloning of Murine CDK9/PITALRE and Its Tissue-Specific Expression in Development, Journal of cellular physiology, vol. 177, No. 2, pp. 206-213, Dec. 7, 1998.

Bartlett, et al., Can Metastatic Colorectal Cancer Be Cured?, Journal Oncology, Cancer Network, vol. 26, No. 3, pp. 266-275, Mar. 15, 2012.

Bartlett, et al., Insights Into the Kinetics of siRNA-Mediated Gene Silencing From Live-Cell and Live-Animal Bioluminescent Imaging, Nucleic Acids Research, vol. 34, Issue 1, pp. 322-333, Jan. 1, 2006.

Behlke, et al., Chemical Modification of siRNAs for In Vivo Use, Oligonucleotides, vol. 18, No. 4, pp. 305-320, Nov. 29, 2008.

Bell, et al., Liposomal Transfection Efficiency and Toxicity on Glioma Cell Lines: In Vitro and In Vitro Studies, Neuroreport, vol. 9, Issue 5, pp. 793-798, Mar. 30, 1998.

Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201.

Billy, et al., Specific Interference With Gene Expression Induced by Long, Double-Stranded RNA in Mouse Embryonal Teratocarcinoma Cell Lines, Proceedings of the National Academy of Sciences, vol. 98, No. 25, pp. 14428-14433, Dec. 4, 2001.

Birmingham, et al., 3' UTR Seed Matches, But Not Overall Identity, Are Associated With RNAi Off-Targets, Nature Methods, vol. 3, No. 3, pp. 199-204, Feb. 17, 2006.

Birmingham, et al., A Protocol for Designing siRNAs With High Functionality and Specificity, Nature Protocols, vol. 2, No. 9, pp. 2068-2078, Aug. 23, 2007.

Biscans et al., "Docosanoic acid conjugation to siRNA enables functional and safe delivery to skeletal and cardiac muscles", Molecular Therapy, Apr. 2021, vol. 29, No. 4, pp. 1382-1394.

Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.

Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.

Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.

Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.

Boutla et al., "Short 5'-phosphorylated double-stranded RNAs induce RNA interference in *Drosophila*", Biology, 2001, 11: 1776-1780.

Braasch, et al., "RNA Interference in Mammalian Cells by Chemically-Modified RNA", Biochemistry, vol. 42, No. 26, pp. 7967-7975, Jun. 11, 2003.

Brennecke, et al., Towards a Complete Description of the microRNA Complement of Animal Genomes, Genome Biology, vol. 4, No. 9, 3 Pages, Aug. 21, 2003.

Brown, et al., Effect of Phosphorothioate Modification of Oligodeoxynucleotides on Specific Protein Binding, Journal of Biological Chemistry, vol. 269, No. 43, pp. 26801-26805, 1994.

Brummelkamp, et al., A System for Stable Expression of Short Interfering RNAs in Mammalian Cells, Science, vol. 296, Issue 5567, pp. 550-553, Apr. 19, 2002.

Burchard, et al., MicroRNA-Like Off-Target Transcript Regulation by siRNAs is Species Specific, RNA, vol. 15, No. 2, pp. 308-315, 2009.

Burke, et al., "Spiral Arterial Remodeling Is Not Essential for Normal Blood Pressure Regulation in Pregnant Mice", Hypertension, vol. 55, No. 3, pp. 729-737, Jan. 25, 2010.

(56) References Cited

OTHER PUBLICATIONS

Byrne, et al., Novel Hydrophobically Modified Asymmetric RNAi Compounds (sd-rxRNA) Demonstrate Robust Efficacy in the Eye, Journal of Ocular Pharmacology and Therapeutics, vol. 29, Issue 10, pp. 855-864, Dec. 3, 2013.
Calegari, et al., Tissue-Specific RNA Interference in Postimplantation Mouse Embryos With Endoribonuclease-Prepared Short Interfering RNA, Proceedings of the National Academy of Sciences, vol. 99, No. 22, pp. 14236-14240, Oct. 29, 2002.
Carter, "Handbook of Parvoviruses", ed., P. Tijsser, CRC Press, pp. 155-168, 1990.
Chang, et al., Asymmetric Shorter-duplex siRNA Structures Trigger Efficient Gene Silencing With Reduced Nonspecific Effects, Molecular Therapy, vol. 17, Issue 4, pp. 725-732, Apr. 2009.
Chang, et al., Enhanced intracellular delivery and multi-target gene silencing triggered by tripodal RNA Structure, The journal of gene Medicine, vol. 14, No. 2, pp. 138-146, Feb. 2012.
Chang, et al., Transgenic Animal Models for Study of the Pathogenesis of Huntington's Disease and Therapy, Drug design, development and therapy, vol. 9, pp. 2179-2188, Apr. 2015.
Chappell, et al., Mechanisms of Palmitic Acid-conjugated Antisense Oligonucleotide Distribution in Mice, Nucleic Acids Research, vol. 48, Issue 8, ,, pp. 4382-4395, May 7, 2020.
Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.
Charrier, et al., Inhibition of SRGAP2 Function by Its Human-Specific Paralogs Induces Neoteny during Spine Maturation, Cell, vol. 149, Issue 4, pp. 923-935, May 11, 2012.
Chen et al., "Lipophilic siRNAs mediate efficient gene silencing in oligodendrocytes with direct CNC delivery", Journal of Controlled Release, Elsevier, vol. 144, pp. 227-232. (Feb. 17, 2010).
Chen et al., "Thermoresponsive polypeptides from pegylated poly-L-glutamates", Biomacromolecules 2011, 12: 2859-2863.
Chen et al., Influence of Particle Size on the in Vivo Potency of Lipid Nanoparticle Formulations of siRNA, Journal of Controlled Release, vol. 235, pp. 236-244, Aug. 10, 2016.
Chen, et al., "Gene Therapy for Brain Tumors: Regression of Experimental Gliomas by Adenovirus-Mediated Gene Transfer In Vivo", Proceedings of the National Academy of Sciences, vol. 91, No. 8, pp. 3054-3057, 1994.
Cheng, et al., Enhanced Hepatic Uptake and Bioactivity of Type α1(I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.
Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.
Cho, et al., Vascular Endothelial Growth Factor Receptor 1 Morpholino Decreases Angiogenesis in a Murine Corneal Suture Model, Investigative ophthalmology & visual science, vol. 53, Issue 2, pp. 685-692, Feb. 2012.
Choe, et al., Crystal Structure of Human Toll-Like Receptor 3 (TLR3) Ectodomain, Science, vol. 309, Issue 5734, pp. 581-585, Jun. 16, 2005.
Chu, et al., Potent RNAi by Short RNA Triggers, RNA, vol. 14, pp. 1714-1719, 2008.
Chung et al., "Reducible siRNA Dimeric Conjugates for Efficient Cellular Uptake and Gene Silencing", Bioconjugate Chem., 2011, 22(2): 299-306.
Coelho, et al., Safety and Efficacy of RNAi Therapy for Transthyretin Amyloidosis, New England Journal of Medicine, vol. 369, No. 9, pp. 819-829, Aug. 29, 2013.
Coles, et al., A High-Throughput Method for Direct Detection of Therapeutic Oligonucleotide-Induced Gene Silencing In Vivo, Nucleic Acid Therapeutics, vol. 26, Issue 2, pp. 86-92, Apr. 11, 2016.

Crooke, et al., Cellular Uptake and Trafficking of Antisense Oligonucleotides, Nature Biotechnology, vol. 35, No. 3, pp. 230-237, Mar. 2017.
Crooke, et al., Phosphorothioate Modified Oligonucleotide-Protein Interactions, Nucleic Acids Research, May 1, 2020, 48(10): 5235-5253.
Cui, et al., "Role of Corin in Trophoblast Invasion and Uterine Spiral Artery Remodelling in Pregnancy", Nature, vol. 484, No. 7393, pp. 246-250, Mar. 21, 2012.
Czauderna, et al., Structural Variations and Stabilising Modifications of Synthetic siRNAs in Mammalian Cells, Nucleic Acids Research, vol. 31, Issue 11, pp. 2705-2716, Jun. 2003.
Dahlman et al., In Vivo Endothelial siRNA Delivery using Polymeric Nanoparticles with Low Molecular Weight, Nature Nanotechnology, vol. 9, No. 9, 17 Pages, Aug. 2014.
Damha et al. (1990) "An improved procedure for derivatization of controlled-pore glass beads for solid-phase oligonucleotide synthesis," Nucleic Acids Research, 18(13):3813-3821.
Dass, Crispin R., Cytotoxicity Issues Pertinent to Lipoplex-Mediated Gene Therapy In-Vivo, Journal of Pharmacy and Pharmacology, vol. 54, Issue 5, pp. 593-601, Feb. 18, 2010.
Davidson, et al., A Model System for In Vivo Gene Transfer Into the Central Nervous System Using an Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types and Regions in the Mammalian Central Nervous System, Proceedings of the National Academy of Sciences, vol. 97, No. 7, pp. 3428-3432, Mar. 28, 2000.
De Fougerolles, et al., "Interfering With Disease: a Progress Report on siRNAbased Therapeutics", Nature Reviews Drug Discovery, vol. 6, pp. 443-453, Jun. 2007.
De Marre et al., "Synthesis, characterization, and in vitro biodegradation of poly(ethylene glycol) modified poly[5N-(2-hydroxyethyl-L-glutamine]", J Bioact Compat Polym, 1996, 11: 85-99.
De Paula et al., "Hydrophobization and bioconjugation for enhanced siRNA delivery and targeting", RNA, Feb. 28, 2007, vol. 13, No. 4, pp. 431-456.
Deleavey, et al., The 5' Binding MID Domain of Human Argonaute2 Tolerates Chemically Modified Nucleotide Analogues, Nucleic acid therapeutics, vol. 23, No. 1, pp. 81-87, Feb. 7, 2013.
Difiglia, et al., Therapeutic Silencing of Mutant Huntingtin With siRNA Attenuates Striatal and Cortical Neuropathology and Behavioral Deficits, Proceedings of the National Academy of Sciences, vol. 104, No. 43, pp. 17204-17209, Oct. 23, 2007.
Dinusha, Differnce Between Sterol and Steroid, Home / Health / Medicine / Nutrients & Drugs, Aug. 4, 2011.
Doench, et al., siRNAs Can Function as miRNAs, Genes & Development, vol. 17, pp. 438-442, 2003.
Dohmen et al., "Defined Folate-PEG-siRNA Conjugates for Receptor-specific Gene Slicing", Molecular Therapy-Nucleic Acids, 2012, 1(1): e7.
Dowdy, Overcoming Cellular Barriers for RNA Therapeutics, Nature Biotechnology, vol. 35, pp. 222-229, Feb. 27, 2017.
Ducruix, et al., Crystallization of Nucleic Acids and Proteins: A Practical Approach, Second Edition, 1999, pp. 201-216.
Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.
Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.
Echevarría, et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.

(56) References Cited

OTHER PUBLICATIONS

Egli, et al., Re-engineering RNA Molecules Into Therapeutic Agents, Accounts of Chemical Research, vol. 52, pp. 1036-1047, 2019.
Egusquiaguirre, et al., "Nanoparticle Delivery Systems for Cancer Therapy: Advances in Clinical and Preclinical Research", Clinical and Translational Oncology, vol. 14, pp. 83-93, 2012.
El Andaloussi, et al., "Exosome-Mediated Delivery of siRNA In Vitro and In Vivo", Nature Protocols, vol. 7, No. 12, pp. 2112-2126, Nov. 15, 2012.
El Andaloussi, et al., "Exosomes for Targeted siRNA Delivery Across Biological Barriers", Advanced Drug Delivery Reviews, vol. 65, pp. 391-397, 2013.
El Andaloussi, et al., "Extracellular Vesicles: Biology and Emerging Therapeutic Opportunities", Nature Reviews Drug Discovery, vol. 12, pp. 347-357, May 2013.
Elbashir, et al., RNA Interference Is Mediated by 21- and 22-Nucleotide RNAs, Genes & Development, vol. 15, No. 2, pp. 188-200, 2001.
Elmen, et al., Locked Nucleic Acid (LNA) Mediated Improvements in siRNA Stability and Functionality, Nucleic Acids Research, vol. 33, Issue 1, pp. 439-447, Jan. 14, 2005.
EMBL Database, WO 2005116204-A/113070: Double Strand Polynucleotides Generating RNA Interference, EBI Accession No. EM PAT:FW706544, XP055753619, , Apr. 18, 2011.
Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.
Eremina, et al., "VEGF Inhibition and Renal Thrombotic Microangiopathy", New England Journal of Medicine, vol. 358, No. 11, pp. 1129-1136, Mar. 13, 2008.
Evers, et al., Antisense Oligonucleotides in Therapy for Neurodegenerative Disorders, Advanced Drug Delivery Reviews, vol. 87, pp. 90-103, Jun. 29, 2015.
Extended European Search Report for European Patent Application No. 16837593.9, dated Mar. 20, 2019.
Extended European Search Report for European Patent Application No. 17745083.0 , dated Jul. 31, 2019.
Extended European Search Report for European Patent Application No. 17840367.1, dated Oct. 14, 2020.
Extended European Search Report for European Patent Application No. 18819571.3, dated May 14, 2021.
Extended European Search Report for European Patent Application No. 19852320.1, dated May 2, 2022.
Extended European Search Report for European Patent Application No. 20164108.1, dated Dec. 3, 2020.
Extended European Search Report for European Patent Application No. 20216265.7, dated Feb. 10, 2022.
Extended European Search Report for European Patent Application No. 21197881.2, dated Oct. 31, 2022.
Fan, et al., Endometrial VEGF Induces Placental sFLT1 and Leads to Pregnancy Complications, The Journal of clinical investigation, vol. 124, No. 11, pp. 4941-4952, Oct. 20, 2014.
Fattal, et al., Biodegradable Polyalkylcyanoacrylate Nanoparticles for the Delivery of Oligonucleotides, Journal of Controlled Release, vol. 53, pp. 137-143, May 1998.
Fedorov, et al., Off-Target Effects by siRNA Can Induce Toxic Phenotype, RNA, vol. 12, No. 7, pp. 1188-1196, May 2006.
Felber, et al., The Interactions of Amphiphilic Antisense Oligonucleotides With Serum Proteins and Their Effects on In Vitro Silencing Activity, Biomaterials, vol. 33, Issue 25, pp. 5955-5965, Sep. 2012.
Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.
Fisher, et al., Transduction With Recombinant Adeno-Associated Virus for Gene Therapy Is Limited by Leading-Strand Synthesis, Journal of virology, vol. 70, No. 1, pp. 520-532, Jan. 1996.

Fitzgerald, et al., A Highly Durable RNAi Therapeutic Inhibitor of PCSK9, New England Journal of Medicine, vol. 376, No. 1, pp. 41-51, Jan. 5, 2017.
Foster et al., "Advanced siRNA Designs Further Improve In Vivo Performance of GalNAc-siRNA Conjugates", Molecular Therapy, vol. 26, No. 3, pp. 709-717, Mar. 2018.
Franich, et al., AAV Vector-Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.
Frank et al., Structural Basis for 5'-Nucleotide Base-specific Recognition of Guide RNA by Human AGO2, Nature, vol. 465, pp. 818-822, Jun. 2010.
Frazier, Antisense Oligonucleotide Therapies: The Promise and the Challenges from a Toxicologic Pathologist's Perspective, Toxicologic pathology, vol. 43, Issue 1, pp. 78-89, Nov. 9, 2014.
Frigg et al., Relationships between vitamin A and vitamin E in the chick, Int J Vitam Nutr Res., 1984, 54(2-3): 125-133.
Furuhashi et al., Expression of Low Density Lipoprotein Receptor Gene in Hjuman Placenta during Pregnancy, Molecular Endocrinology, 1989, 3: 1252-1256.
Gaglione, et al., Recent Progress in Chemically Modified siRNAs, Mini Reviews in Medicinal Chemistry, vol. 10, No. 7, pp. pp. 578-595, 2010.
Gaus, et al., Characterization of the Interactions of Chemically-modified Therapeutic Nucleic Acids With Plasma Proteins Using a Fluorescence Polarization Assay, Nucleic Acids Research, vol. 47, No. 3, pp. 1110-1122, 2019.
Gavrilov et al. (Jun. 2012) "Therapeutic siRNA: principles, challenges, and strategies", Yale Journal of Biology and Medicine, 85:187-200.
Geary, Antisense Oligonucleotide Pharmacokinetics and Metabolism, Expert Opinion on Drug Metabolism & Toxicology, vol. 5, pp. 381-391, Apr. 1, 2009.
Geary, et al., Pharmacokinetics, Biodistribution and Cell Uptake of Antisense Oligonucleotides, Advanced Drug Delivery Reviews, vol. 87, pp. 46-51, Jun. 29, 2015.
Genbank, Mus Musculus Non-Coding RNA, Oocyte_Clustered_Small_RNA6599, Complete Sequence, GenBank Accession No. AB341398.1, May 24, 2008, 1 page.
Genbank, Rattus Norvegicus piRNA piR-182271, Complete Sequence, GenBank Accession No. DQ766949.1, Jul. 12, 2006, 1 Page.
Genbank, Signal Recognition Particle 54 kDa protein 2 [Perkinsus marinus ATCC 50983], NCBI Reference Sequence: XP_002784438.1, Apr. 30, 2010.
Gilany, et al., The Proteome of the Human Neuroblastoma Cell Line SH-SY5Y: An Enlarged Proteome, Biochimica et Biophysica Acta (BBA)—Proteins and Proteomics, vol. 1784, Issues 7-8, pp. 983-985, Jul.-Aug. 2008.
Gilbert, et al., "Hypertension Produced by Reduced Uterine Perfusion in Pregnant Rats Is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Godinho et al., Pharmacokinetic Profiling of Conjugated Therapeutic Oligonucleotides: A High-Throughput Method based upon Serial Blood Microsampling Coupled to Peptide Nucleic Acid Hybridization Assay, Nucleic Acid Therapeutics, vol. 27, pp. 323-334, Dec. 1, 2017.
Goodson et al., Dental Applications, Medical Applications of Controlled Release, vol. 2, pp. 115-138, 1984.
Grad, et al., Computational and Experimental Identification of C. elegans microRNAs, Molecular Cell, vol. 11, Issue 5, pp. 1253-1263, May 2003.

(56) References Cited

OTHER PUBLICATIONS

Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.
Griffiths-Jones, San, The microRNA Registry, Nucleic Acids Research, vol. 32, Issue Supplement 1, pp. D109-D111, Jan. 1, 2004.
Grimm, D, Asymmetry in siRNA Design, Gene Therapy, vol. 16, No. 7, pp. 827-829, Apr. 30, 2009.
Grimm, et al., Fatality in Mice Due to Oversaturation of Cellular MicroRNA/short Hairpin RNA Pathways, Nature, vol. 441, No. 7092, pp. 537-541, May 25, 2006.
Gvozdeva et al., "Noncanonical Synthetic RNAi Inducers InL RNA Interference", InTech, Apr. 6, 2016.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Hammerling et al., Monoclonal Antibodies and T-Cell Hybridomas, Research Monographs in Immunology, vol. 3, pp. 563-681, 1981.
Haraszti, et al., "5'-Vinylphosphonate improves tissue accumulation and efficacy of conjugated siRNAs in vivo", Nucleic Acids Research, Jul. 27, 2017, 45(13): 7581-7592.
Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.
Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.
Herdewijn, Piet, Heterocyclic Modifications of Oligonucleotides and Antisense Technology, Antisense and Nucleic Acid Drug Development, vol. 10, Issue 4, pp. 297-310, Jul. 8, 2004.
Heydarian, et al., Novel Splice Variants of sFlt1 are Upregulated in Preeclampsia, Placenta, vol. 30, Issue 3, pp. 250-255, Mar. 2009.
Heyer, et al., An Optimized Kit-Free Method for Making Strand-Specific Deep Sequencing Libraries From RNA Fragments, Nucleic Acids Research, vol. 43, Issue 1, pp. 1-14, Jan. 9, 2015.
Hirashima, et al., "Trophoblast Expression of Fms-like Tyrosine Kinase 1 Is Not Required for the Establishment of the Maternal-fetal Interface in the Mouse Placenta", Proceedings of the National Academy of Sciences of the United States of America, vol. 100, No. 26, pp. 15637-15642, Dec. 23, 2003.
Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.
Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.
Huang, Preclinical and Clinical Advances of GalNAc-Decorated Nucleic Acid Therapeutics, Molecular Therapy—Nucleic Acids, vol. 6,, pp. 116-132, Mar. 17, 2017.
Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.
Hutvagner, et al., A microRNA in a Multiple-Turnover RNAi Enzyme Complex, Science, vol. 297, Issue 5589, pp. 2056-2060, Sep. 20, 2002.
Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.
International Search Report & Written Opinion Received for PCT Application No. PCT/US2019/046013, dated Jan. 9, 2020.
International Search Report & Written Opinion Received for PCT Application No. PCT/US2020/014181, dated Jun. 2, 2020.
International Search Report and Written Opinion for PCT International Patent Application No. PCT/US2019/048027 dated Nov. 15, 2019.
International Search Report and Written Opinion for PCT International Patent Application No. PCT/US2020/047492, dated Feb. 17, 2022.
International Search Report and Written Opinion in related PCT Application No. PCT/US2020/014146, dated May 22, 2020.
International Search Report and Written Opinion received for PCT Patent Application No. PCT/US2016/025722, dated Aug. 12, 2016.
International Search Report and Written Opinion received for PCT Patent Application No. PCT/US2016/025731, dated Sep. 9, 2016.
International Search Report and Written Opinion received for PCT Patent Application No. PCT/US2016/025753, dated Sep. 14, 2016.
International Search Report and Written Opinion received for PCT Patent Application No. PCT/US2016/046810, dated Nov. 29, 2016.
International Search Report and Written Opinion received for PCT Patent Application No. PCT/US2017/015633, dated May 11, 2017.
International Search Report and Written Opinion received for PCT Patent Application No. PCT/US2018/038952, dated Sep. 24, 2018.
International Search Report and Written Opinion received for PCT Patent Application No. PCT/US2020/045487, dated Dec. 31, 2020.
International Search Report and Written Opinion received for PCT Patent Application No. PCT/US2021/013620, dated Apr. 26, 2021.
International Search Report and Written Opinion received for PCT Patent Application No. PCT/US2021/034290, dated Nov. 4, 2021.
International Search Report and Written Opinion received for PCT Patent Application No. PCT/US2021/041946, dated Oct. 29, 2021.
Iriyama et al., Hypoxia-independent up-regulation of placental HIF-1α gene expression contributes to the pathogenesis of preeclampsia, Hypertension, Jun. 2015, 65(6): 1307-1315, Supplemental Data.
Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.
Jackson et al., Position-Specific Chemical Modification of siRNAs Reduces "Off-Target" Transcript Silencing, RNA, vol. 12, No. 7, pp. 1197-1205, May 8, 2006.
Jackson, et al., Recognizing and Avoiding siRNA Off-Target Effects for Target Identification and Therapeutic Application, Nature Reviews Drug Discovery, vol. 9, No. 1, pp. 57-67, Jan. 1, 2010.
Jacque, et al., Modulation of HIV-1 replication by RNA interference, Nature, vol. 418, No. 6896, pp. 435-438, Jun. 26, 2002.
Janssen, et al., Long-Chain Polyunsaturated Fatty Acids (LCPUFA) From Genesis to Senescence: The Influence of LCPUFA on Neural Development, Aging, and Neurodegeneration, Progress in Lipid Research, vol. 53, pp. 1-17, Jan. 2014.
Jebbink et al., "Expression of Placental FLT1 Transcript Variants Relates to Both Gestational Hypertensive Disease and Fetal Growth", Hypertension, Apr. 25, 2011, 58(1): 70-76.
Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.
Jo, et al., Selection and Optimization of Asymmetric siRNA Targeting the Human c-MET Gene, Molecules and cells, vol. 32, No. 6, pp. 543-548, Dec. 31, 2011.
Judge, et al., Design of Noninflammatory Synthetic siRNA Mediating Potent Gene Silencing in Vivo, Molecular Therapy, vol. 13, Issue 3, pp. 494-505, Mar. 2006.
Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.
Kamba, et al., "VEGF-dependent Plasticity of Fenestrated Capillaries in the Normal Adult Microvasculature", American Journal of Physiology-Heart and Circulatory Physiology, vol. 29, pp. H560-H576, Feb. 1, 2006.
Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.
Karlin, et al., Applications and Statistics for Multiple High-Scoring Segments in Molecular Sequences, Proceedings of the National Academy of Sciences of the USA, vol. 90, pp. 5873-5877, Jun. 1993.

(56) References Cited

OTHER PUBLICATIONS

Karlin, et al., Methods for Assessing the Statistical Significance of Molecular Sequence Features by Using General Scoring Schemes, Proceedings of the National Academy of science of the USA, vol. 87, No. 6, pp. 2264-2268, Mar. 1990.

Karra, et al., Transfection Techniques for Neuronal Cells, Journal of Neuroscience, vol. 30, No. 18, pp. 6171-6177, May 5, 2010.

Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.

Kenski et al. (2012) "siRNA-optimized Modifications for Enhanced In Vivo Activity," Mol. Ther. Nucleic Acids. 1:e5. pp. 1-8.

Khan et al., Silencing Myostatin using Cholesterol-Conjugated siRNAs Induces Muscle Growth, Molecular Therapy, Nucleic Acids, vol. 5, 9 Pages, Jan. 1, 2016.

Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.

Khvorova, et al., Abstract IA27: Advances in Oligonucleotide Chemistry for the Treatment of Neurodegenerative Disorders and Brain Tumors, Cancer Research, vol. 76, Issue 6, Abstract IA27, Mar. 2016.

Khvorova, et al., Functional siRNAs and miRNAs Exhibit Strand Bias, Cell, vol. 115, Issue 2, pp. 209-216, Oct. 17, 2003.

Khvorova, Oligonucleotide Therapeutics—A New Class of Cholesterol-Lowering Drugs, The New England Journal of Medicine, vol. 376, No. 1, pp. 4-7, Jan. 5, 2017.

Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.

Kim et al., "PEG conjugated VEGF siRNA for anti-angiogenic gene therapy", Journal of Controlled Release, Jun. 3, 2006, vol. 116, No. 2, pp. 123-129.

Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.

Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).

Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).

Kubo, et al., Modified 27-nt dsRNAs With Dramatically Enhanced Stability in Serum and Long-term RNAi Activity, Oligonucleotides, vol. 17, No. 4, pp. 445-464, 2007.

Kumar, et al., "Shielding of Lipid Nanoparticles for siRNA Delivery: Impact on Physicochemical Properties", Cytokine Induction, and Efficacy, Molecular Therapy-Nucleic Acids, vol. 3, e210, pp. 1-7, Nov. 18, 2014.

Lagos-Quintana, et al., Identification of Novel Genes Coding for Small Expressed RNAs, Science, vol. 294, Issue 5543, pp. 853-858, Oct. 26, 2001.

Lagos-Quintana, et al., Identification of Tissue-Specific MicroRNAs from Mouse, Current Biology, vol. 12, Issue 9, pp. 735-739, Apr. 30, 2002.

Lagos-Quintana, et al., New microRNAs From Mouse and Human, RNA, vol. 9, No. 2, pp. 175-179, 2003.

Lai, et al., Computational Identification of Drosophila microRNA Genes, Genome Biology, vol. 4, No. 7, pp. 1-20, Jun. 30, 2003.

Lam, et al., "A New Type of Synthetic Peptide Library for Identifying Ligand-Binding Activity", Nature, vol. 354, pp. 82-84, Nov. 7, 1991.

Lambert, et al., "Nanoparticulate Systems for the Delivery of Antisense Oligonucleotides", Advanced Drug Delivery Reviews, vol. 47, pp. 99-112, 2001.

Lan, et al., Neuroactive Steroid Actions at the GABAA Receptor, Hormones and Behavior, vol. 28, Issue 4, pp. 537-544, Dec. 1994.

Landis, et al., "A Call for Transparent Reporting to Optimize the Predictive Value of Preclinical Research", Nature, vol. 490, pp. 187-191, Oct. 10, 2012.

Lau, et al., An Abundant Class of Tiny RNAs with Probable Regulatory Roles in Caenorhabditis elegans, Science, vol. 294, Issue 5543, pp. 858-862, Oct. 26, 2001.

Lau, et al., Characterization of the piRNA Complex from Rat Testes, Science, vol. 313, Issue 5785, pp. 363-367, Jul. 21, 2006.

Laufer, et al., "Selected Strategies for the Delivery of siRNA In Vitro and In Vivo", RNA Technologies and Their Applications, 2010, pp. 29-58.

Lee et al., "Current preclinical small interfering RNA (siRNA)-based conjugate systems for RNA therapeutics", Advanced Drug Delivery Reviews, Oct. 27, 2015, vol. 104, pp. 78-92.

Lee, et al., "Recent Developments in Nanoparticle-Based siRNA Delivery for Cancer Therapy", BioMed Research International, vol. 2013, Article ID 782041, 10 Pages, Jun. 2013.

Lee, et al., An Extensive Class of Small RNAs in Caenorhabditis elegans, Science, vol. 294, Issue 5543, pp. 862-864, Oct. 26, 2001.

Lee, et al., Expression of Small Interfering RNAs Targeted Against HIV-1 rev Transcripts in Human Cells, Nature Biotechnology, vol. 20, No. 5, pp. 500-505, May 1, 2002.

Lee, et al., RNA Interference-Mediated Simultaneous Silencing of Four Genes Using Cross-Shaped RNA, Molecules and Cells, vol. 35, No. 4, pp. 320-326, Apr. 4, 2013.

Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.

Levine, et al., "Circulating Angiogenic Factors and the Risk of Preeclampsia", The New England Journal of Medicine, vol. 350, pp. 672-683, 2004.

Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.

Li, et al., Distribution of 5-Hydroxymethylcytosine in Different Human Tissues, "SAGE—Hindawi Access to Research, Journal of Nucleic Acids, vol. 2011", pp. 1-7, 2011.

Li, et al., Huntington's Disease Gene (IT15) Is Widely Expressed in Human and Rat Tissues, Neuron, vol. 11, No. 5, pp. 985-993, Nov. 1993.

Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.

Lim, et al., The microRNAs of Caenorhabditis elegans, Genes & Development, vol. 17, No. 8, pp. 991-1008, 2003.

Lim, et al., Vertebrate MicroRNA Genes, Science, vol. 299, Issue 5612, p. 1540, Mar. 7, 2003.

Lima, et al., Single-Stranded siRNAs Activate RNAi in Animals, Cell, vol. 150, Issue 5, pp. 883-894, Aug. 31, 2012.

Liu et al., Snapshot PK: A Rapid Rodent in Vivo Preclinical Screening Approach, Drug Discovery Today, vol. 13, No. 7-8, pp. 360-367, Apr. 1, 2008.

Lopes, et al., Comparison Between Proliferative and Neuron-Like SH-SY5Y Cells as an In Vitro Model for Parkinson Disease Studies, Brain Research, vol. 1337, pp. 85-94, Jun. 14, 2010.

Lorenz, et al., Steroid and Lipid Conjugates of siRNAs to Enhance Cellular Uptake and Gene Silencing in Liver Cells, Bioorganic & Medicinal Chemistry Letters, vol. 14, Issue 19, pp. 4975-4977, Oct. 4, 2004.

Lundh, et al., Hypothalamic Expression of Mutant Huntingtin Contributes to the Development of Depressive-Like Behavior in the Bac Transgenic Mouse Model of Huntington's Disease, Human Molecular Genetics, vol. 22, Issue 17, pp. 3485-3497, Sep. 1, 2013.

Luo, et al., Photoreceptor Avascular Privilege Is Shielded by Soluble VEGF Receptor-1, Elife, vol. 2, pp. 1-22, Jun. 18, 2013.

(56) References Cited

OTHER PUBLICATIONS

Ly et al., Visualization of Self-Delivering Hydrophobically Modified siRNA Cellular Internalization, Nucleic Acids Research, vol. 45, pp. 15-25, Nov. 29, 2016.
Ma et al., Structural Basis for 5'-End-Specific Recognition of Guide RNA by the A. Fulgidus Piwi Protein, Nature, vol. 434, No. 7033, pp. 666-670, Mar. 31, 2005.
Ma, et al., Structural Basis for Overhang-Specific Small Interfering RNA Recognition by the PAZ Domain, Nature, vol. 429, No. 6989, pp. 318-322, May 20, 2004.
Makris, et al., "Uteroplacental Ischemia Results in Proteinuric Hypertension and Elevated sFLT-1", Kidney International, vol. 71, Issue 1, pp. 977-984, May 2, 2007.
Maltepe, et al., "The Placenta: Transcriptional, Epigenetic, and Physiological Integration During Development", The Journal of Clinical Investigation, vol. 120, No. 4, pp. 1016-1025, Apr. 1, 2010.
Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.
Mantha, et al., Rnai-Based Therapies for Huntington's Disease: Delivery Challenges and Opportunities, Therapeutic Delivery, vol. 3, No. 9, pp. 1061-1076, Aug. 29, 2012.
Marcus, et al., FedExosomes: Engineering Therapeutic Biological Nanoparticles that Truly Deliver, Pharmaceuticals, vol. 6, Nos. pp. 659-680, Apr. 29, 2013.
Marques, et al., A Structural Basis for Discriminating Between Self and Nonself Double-Stranded Rnas in Mammalian Cells, Nature biotechnology, vol. 23, No. 11, pp. 1399-1405, 2005.
Masotti, et al., Comparison of Different Commercially Available Cationic Liposome-DNA Lipoplexes: Parameters Influencing Toxicity and Transfection Efficiency, Colloids and Surfaces B: Biointerfaces, vol. 68, Issue 2, pp. 136-144, Feb. 1, 2009.
Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.
Maynard, et al., "Excess Placental Soluble fms-like Tyrosine Kinase 1 (sFltl) may Contribute to Endothelial Dysfunction", Hypertension, and Proteinuria in Preeclampsia, The Journal of Clinical Investigation, vol. 111, pp. 649-658, 2003.
Mccaffrey, et al., Gene Expression: RNA Interference in Adult Mice, Nature, vol. 418, No. 6893, pp. 38-39, Jul. 4, 2002.
Mcmanus, et al., Gene Silencing Using Micro-RNA Designed Hairpins, RNA, vol. 8, Issue 6, pp. 842-850, Aug. 20, 2002.
Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.
Miyagishi, et al., U6 promoter-driven siRNAs With Four Uridine 3' Overhangs Efficiently Suppress Targeted Gene Expression in Mammalian Cells, Nature Biotechnology, vol. 20, No. 5, pp. 497-500, May 1, 2002.
Mok, et al., Multimeric small interfering ribonucleic acid for highly efficient sequencespecific gene silencing~, Nature Materials, vol. 9, pp. 272-278, Jan. 24, 2010.
Molitoris, et al., siRNA Targeted to p53 Attenuates Ischemic and Cisplatin-Induced Acute Kidney Injury, Journal of the American Society of Nephrology, vol. 20, Issue 8, pp. 1754-1764, Aug. 1, 2009.
Morrissey et al., "Activity of stabilized short interfering RNA in a mouse model of hepatitis B virus replication", Hepatology, 2005, 41: 1349-1356.
Mourelatos, et al., miRNPs: A Novel Class of Ribonucleoproteins Containing Numerous microRNAs, Genes & Development, vol. 16, No. 6, pp. 720-728, 2002.
Mullen, et al., NeuN, A Neuronal Specific Nuclear Protein In Vertebrates, Development, vol. 116, No. 1, pp. 201-211, 1992.
Myers, et al., Optimal Alignments in Linear Space, Computer Applications in the Biosciences, vol. 4, No. 1, pp. 11-17, Mar. 1988.

Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.
Nair, et al., Impact of Enhanced Metabolic Stability on Pharmacokinetics and Pharmacodynamics of GalNAc-siRNA Conjugates, Nucleic Acids Research, vol. 45, Issue 19, pp. 10969-10977, Nov. 2, 2017.
Nair, et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, pp. 16958-16961, Dec. 10, 2014.
Nallagatla et al., Nucleoside Modifications Modulate Activation of the Protein Kinase PKR in an RNA Structure-Specific Manner, RNA, vol. 14, pp. 1201-1213, Jun. 1, 2008.
Nelson et al. (1992) "Oligonucleotide labeling methods 3. Direct labeling of oligonucleotides employing a novel, non-nucleosidic, 2-aminobutyl-1 ,3-propanediol backbone," 20(23):6253-6259.
Neufeld, et al., "Similarities and Differences Between the Vascular Endothelial Growth Factor (VEGF) Splice Variants", Cancer and Metastasis Reviews, vol. 15, pp. 153-158, Jun. 1996.
Nielsen, et al., Sequence-Selective Recognition of DNA by Strand Displacement With a Thymine-Substituted Polyamide, Science, vol. 254, Issue 5037, pp. 1497-1500, Dec. 6, 1991.
Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.
Nikan, et al., Docosahexaenoic Acid Conjugation Enhances Distribution and Safety of siRNA upon Local Administration in Mouse Brain, Molecular Therapy—Nucleic Acids, vol. 5, No. 8, pp. 1-11, Aug. 9, 2016, with Supplement.
Nishina et al., "Efficient In Vivo Delivery of siRNA to the Liver by Conjugation of α—Tocopherol", Mol Ther., Apr. 2008, 16(4): 734-740.
Oberbauer et al., Renal Uptake of an 18-mer Phosphorothioate Oligonucleotide, Kidney International, vol. 48, pp. 1226-1232, 1005.
Ohnishi, et al., "Enhancement of Allele Discrimination by Introduction of Nucleotide Mismatches into siRNA in Allele-Specific Gene Silencing by RNAi", Pios One, vol. 3, Issue 5, e2248, 9 Pages, May 2008.
Osborn et al., Hydrophobicity Drives the Systemic Distribution of Lipid-Conjugated siRNAs via Lipid Transport Pathways, Nucleic Acids Research, vol. 47, No. 3, pp. 1070-1081, Dec. 8, 2018.
Osborn, et al., "Improving siRNA Delivery In Vivo Through Lipid Conjugation", Nucleic Acid Therapeutics, vol. 28, No. 3, pp. 128-136, May 10, 2018.
Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.
Ouimet, et al., DARPP-32, A Dopamine- and Adenosine 3':5'-Monophosphate-Regulated Phosphoprotein Enriched in Dopamine-Innervated Brain Regions. III. Immunocytochemical Localization, Journal of Neuroscience, vol. 4, No. 1, pp. 111-124, Jan. 1, 1984.
Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.
Owen, Morpholino-Mediated Increase in Soluble Flt-1 Expression Results in Decreased Ocular and Tumor Neovascularization, PLoS One, vol. 7, No. 3, pp. e33576, Mar. 15, 2012.
Paddison, et al., Short Hairpin RNAs (shRNAs) Induce Sequence-Specific Silencing in Mammalian Cells, Genes & Development, vol. 16, No. 8, pp. 948-958, 2002.
Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.
Partial European Search Report for European Patent Application No. 20216265.7, dated Nov. 10, 2021.
Partial European Search Report for European Patent Application No. 21107881.2, dated Mar. 14, 2022.

(56) References Cited

OTHER PUBLICATIONS

Partial Supplementary European Search Report for European Patent Application No. 20741865.8, dated Dec. 20, 2022.
Pasquinelli, et al., Conservation of the Sequence and Temporal Expression of let-7 Heterochronic Regulatory RNA, Nature, vol. 408, No. 6808, pp. 86-89., Nov. 2, 2000.
Paul, et al., Effective Expression of Small Interfering RNA in Human Cells, Nature Biotechnology, vol. 20, No. 5, pp. 505-508, May 1, 2002.
Peel, et al., Conjugation and Evaluation of Small Hydrophobic Molecules to Triazole-Linked siRNAs, ACS medicinal chemistry letters, vol. 6, No. 2, pp. 117-122, Dec. 4, 2014.
Pei, et al., Quantitative Evaluation of siRNA Delivery in Vivo, RNA, vol. 16, No. 12, pp. 2553-2563, Oct. 12, 2010.
Petersen, et al., LNA: A Versatile Tool for Therapeutics and Genomics, Trends in Biotechnology, vol. 21, Issue 2, pp. 74-81, Feb. 2003.
Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.
Podbevsek et al., "Solution-state structure of a fully alternately 2'-F/2'-OMe modified 42-nt dimeric siRNA construct", Nucleic Acids Research, vol. 38, No. 20, pp. 7298-7307, DOI: 10.1093/nar/gkq621. (Jul. 12, 2010).
Pokholenko et al., Lipid Oligonucleotide Conjugates as Responsive Nanomaterials for Drug Delivery, Journal of Materials Chemistry B, vol. 1, 6 Pages, 2013.
Posocco, et al., "Impact of siRNA Overhangs for Dendrimer-mediated siRNA Delivery and Gene Silencing", Molecular Pharmaceutics, Aug. 5, 2013, 10(8): 3262-3273.
Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.
Prakash et al., Targeted Delivery of Antisense Oligonucleotides to Hepatocytes Using Triantennary N-Acetyl Galactosamine Improves Potency 10-Fold in Mice, Nucleic Acids Research, vol. 42, Issue 13, pp. 8796-8807, Jul. 29, 2014.
Prakash, et al., Identification of Metabolically Stable 5'-Phosphate Analogs That Support Single-Stranded siRNA Activity, Nucleic Acids Research, Mar. 9, 2015, 43(6): 2993-3011.
Pubchem Database, Amino-Teg-Diol, National Institute or Biotechnology Information, PubChem Accession No. 22136768, 2003.
Pubchem Database, SCHEMBL867745, National Institute for Biotechnology Information, PubChem Accession No. 12454428, 12 pages, 2005.
PubChem Detabase, CID-16131506, Compund Summary: dGTGGGTGGGT, Jul. 3, 2007, Retrieved from url: https://pubchem.ncbi.nlm.nih.gov/compound/16131506.
Putnam, David A., Antisense Strategies and Therapeutic Applications, American Journal of Health System Pharmacy, vol. 53, No. 2, pp. 151-160, Jan. 15, 1996.
Raal, et al., Inclisiran for the Treatment of Heterozygous Familial Hypercholesterolemia, New England Journal of Medicine, vol. 382, No. 16, pp. 1520-1530, Apr. 16, 2020.
Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.
Raouane et al., "Lipid Conjugated Oligonucleotides: A Useful Strategy for Delivery", Chem., 2012, 23: 1091-1104.
Reed et al., Forty Mouse Strain Survey of Body Composition, Physiology & Behavior, vol. 91, No. 5, 15 Pages, Aug. 15, 2007.
Reinhart, et al., Small RNAs Correspond to Centromere Heterochromatic Repeats, Science, vol. 297, No. 5588, 1 Page, Sep. 13, 2002.
Reynolds, A, et al., Rational siRNA Design for RNA Interference, Nature Biotechnology, vol. 22, No. 3, pp. 326-330, Apr. 2004.
Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.
Rodriguez-Lebron, et al., Intrastriatal rAAV-Mediated Delivery of Anti-Huntingtin shRNAs Induces Partial Reversal of Disease Progression in R6/1 Huntington's Disease Transgenic Mice, Molecular Therapy, vol. 12, Issue 4, pp. 618-633, Oct. 2005.
Rupprecht, et al., Neuroactive Steroids: Mechanisms of Action and Neuropsychopharmacological Properties, Psychoneuroendocrinology, vol. 28, Issue 2, pp. 139-168, Feb. 2003.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Sah, et al., Oligonucleotide Therapeutic Approaches for Huntington disease, The Journal of Clinical Investigation, vol. 121, No. 2, pp. 500-507, Feb. 1, 2011.
Samuelson, Kristin W., Post-Traumatic Stress Disorder and Declarative Memory Functioning: A Review, Dialogues in Clinical Neuroscience, vol. 13, No. 3, pp. 346-351, Sep. 2011.
Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.
Scherman et al., Genetic Pharmacology: Progresses in siRNA Delivery and Therapeutic Applications, Gene Therapy, vol. 24, pp. 151-156, Mar. 2017.
Schirle, et al., Structural Basis for MicroRNA Targeting, Science, vol. 346, Issue 6209, pp. 608-613, Oct. 31, 2014.
Schoch, et al., Antisense Oligonucleotides: Translation From Mouse Models to Human Neurodegenerative Diseases, Neuron, vol. 94, Issue 6, pp. 1056-1070, Jun. 21, 2017.
Schwab, et al., An Approach for New Anticancer Drugs:Oncogene-Targeted Antisense DNA, Annals of Oncology, vol. 5, Issue 4, pp. 55-58, 1994.
Schwarz, et al., Asymmetry in the Assembly of the RNAi Enzyme Complex, Cell, vol. 115, Issue 2, pp. 199-208, Oct. 17, 2003.
SEQ ID No. 1112 from U.S. Pat. No. 7,790,867. [Accessed Nov. 28, 2018, http://seqdata.uspto.gov/.psipsv?pageRequest=viewSequence&DocID=7790867&seqID=1112.]
Setten, et al., The Current State and Future Directions of RNAi-based Therapeutics, Nature Reviews Drug Discovery, vol. 18, pp. 421-446, Mar. 7, 2019.
Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.
Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.
Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.
Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.
Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.
Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.
Soutschek, et al., Therapeutic Silencing of an Endogenous Gene by Systemic Administration of Modified siRNAs, Nature, vol. 432, No. 7014, pp. 173-178, Nov. 11, 2004.
Stalder, et al., The Rough Endoplasmatic Reticulum Is a Central Nucleation Site of siRNA-Mediated RNA Silencing, The EMBO Journal, vol. 32, Issue 8, pp. 1115-1127, Mar. 19, 2013.

(56) References Cited

OTHER PUBLICATIONS

Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Physicochemical Properties of Phosphorothioate Oligodeoxynucleotides, Nucleic Acids Research, vol. 16, No. 8, pp. 3209-3221, Apr. 25, 1988.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Stokman, et al., Application of siRNA in Targeting Protein Expression in Kidney Disease, Advanced Drug Delivery Reviews, vol. 62, Issue 14, pp. 1378-1389, Nov. 30, 2010.
Sugo et al., "Development of antibody-siRNA conjugate targeted to cardiac and skeletal muscles", Journal of Controlled Release, Jun. 29, 2016, vol. 237, pp. 1-13.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Sui, et al., A DNA Vector-Based RNAi Technology to Suppress Gene Expression in Mammalian Cells, Proceedings of the National Academy of Sciences, vol. 99, No. 8, pp. 5515-5520, Apr. 16, 2002.
Sun, et al., Asymmetric RNA Duplexes Mediate RNA Interference in Mammalian Cells, Nature Biotechnology, vol. 26, pp. 1379-1382, Dec. 2008.
Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.
Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.
Thomas et al. (2007) "Intronic polyadenylation signal sequences and alternate splicing generate human soluble Flt1 variants and regulate the abundance of soluble Flt1 in the placenta," The FASEB Journal, 21(14):3885-3895.
Thomas, et al., A Recently Evolved Novel Trophoblast-Enriched Secreted Form of fms-Like Tyrosine Kinase-1 Variant Is Up-Regulated in Hypoxia and Preeclampsia, The Journal of Clinical Endocrinology & Metabolism, vol. 94, Issue 7, pp. 2524-2530, Jul. 1, 2009.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Tischer, et al., "The Human Gene for Vascular Endothelial Growth Factor. Multiple Protein Forms are Encoded Through Alternative Exon Splicing", The Journal of Biological Chemistry, vol. 266, pp. 11947-11954, Jun. 25, 1991.
Turanov et al., "RNAi Modulation of Placental sFLT1 for the Treatment of Preeclampsia", Nature Biotechnology, Nov. 19, 2018, 36: 1164-1173.
Tuschl et al. (May 6, 2004) "The siRNA User Guide," Accessible on the Internet at URL: http://diyhpl.us/~bryan/irc/protocol-online/protocol-cache/sirna.html. [Last Accessed Aug. 11, 2016].
Tuschl, et al., Expanding small RNA interference, Nature Biotechnology, vol. 20, No. 5, pp. 446-448, 2002.

Uchida, et al., "An Integrated Approach for the Systematic Identification and Characterization of Heart-enriched Genes With Unknown Functions", BMC Genomics, vol. 10, No. 100, pp. 1-12, Mar. 2009.
Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).
Vaught, et al., T7 RNA Polymerase Transcription with 5-Position Modified UTP Derivatives, Journal of the American Chemical Society, vol. 126, No. 36, pp. 11231-11237, Aug. 19, 2004.
Vickers, et al., Development of a Quantitative BRET Affinity Assay for Nucleic Acidprotein Interactions, PloS One, vol. 11, No. 8, p.e0161930, pp. 1-17, Aug. 29, 2016.
Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.
Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wada et al., "Evaluation of the effects of chemically different linkers on hepatic accumulations, cell tropism and gene silencing ability of cholesterol-conjugated antisense oligonucleotides", Journal of Controlled Release, Elsevier, vol. 226, pp. 57-65, DOI: 10.1016/J.JCONREL.2016.02.007. (Feb. 5, 2016).
Wang, et al., Nanoparticle-Based Delivery System for Application of siRNA In Vivo, Current Drug Metabolism, vol. 11, No. 2, pp. 182-196, 2010.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Watanabe, et al., Endogenous siRNAs From Naturally Formed dsRNAs Regulate Transcripts in Mouse Oocytes, Nature, vol. 453, No. 7194, pp. 539-543, Apr. 10, 2008.
Weyer, et al., Developmental and Cell Type-Specific Expression of the Neuronal Marker NeuN in the Murine Cerebellum, Journal of Neuroscience Research, vol. 73, Issue 3, pp. 400-409, May 23, 2003.
Whitehead et al., Degradable Lipid Nanoparticles with Predictable in Vivo siRNA Delivery Activity, Nature Communications, vol. 5, pp. 1-10, Jun. 27, 2014.
Whitehead, et al., "Knocking Down Barriers: Advances in siRNA Delivery", Nature Reviews Drug Discovery, vol. 8, No. 2, pp. 129-138, Feb. 2009.
Wickstrom, Oligodeoxynucleotide Stability in Subcellular Extracts and Culture Media, Journal of Biochemical and Biophysical Methods, vol. 13, Issue 2, pp. 97-102, Sep. 1986.
Wolfrum et al., "Mechanisms and optimization of in vivo delivery of lipophilic siRNAs", Nature Biotechnology, Oct. 2007, 25(10): 1149-1157.
Wong, et al., Co-Injection of a Targeted, Reversibly Masked Endosomolytic Polymer Dramatically Improves the Efficacy of Cholesterol-Conjugated Small Interfering RNAs In Vivo, Nucleic Acid Therapeutics, vol. 22, No. 6, pp. 380-390, Nov. 26, 2012.
Wooddell, et al., Hepatocyte-targeted RNAi Therapeutics for the Treatment of Chronic Hepatitis B Virus Infection, Molecular Therapy, vol. 21, Issue 5, pp. 973-985, May 2013.
Wright, et al., Identification of Factors That Contribute to Recombinant AAV2 Particle Aggregation and Methods to Prevent Its Occurrence During Vector Purification and Formulation, Molecular Therapy, vol. 12, Issue 1,, pp. 171-178, Jul. 2005.
Xia, et al., siRNA-Mediated Gene Silencing in Vitroand In Vivo, Nature Biotechnology, vol. 20, No. 10, pp. 1006-1010, Sep. 16, 2002.
Yamana, et al., 2'-Pyrene Modified Oligonucleotide Provides a Highly Sensitive Fluorescent Probe of RNA, Nucleic Acids Research, 1999, 27(11): 2387-2392.
Yekta, et al., MicroRNA-Directed Cleavage of HOXB8 mRNA, Science, Apr. 23, 2004, 304(5670): 594-596.

(56) References Cited

OTHER PUBLICATIONS

Young, et al., Pathogenesis of Preeclampsia, Annual Review of Pathology: Mechanisms of Disease, vol. 5, pp. 173-192, Feb. 2, 2010.
Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.
Yu, et al., RNA Interference by Expression of Short-Interfering RNAs and Hairpin Rnas in Mammalian Cells, Proceedings of the National Academy of Sciences, vol. 99, No. 9, pp. 6047-6052., Apr. 30, 2002.
Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.
Yuan, et al., Recent Advances of siRNA Delivery by Nanoparticles, Expert Opinion on Drug Delivery vol. 8, Issue 4, pp. 521-536, 2011.
Zamore, et al., Ancient Pathways Programmed by Small RNAs, Science, May 17, 2002, 296(5571): 1265-1269.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones and Their Inhibition of Mutant SOD1-Dependent Protein Aggregation and Toxicity in PC12 Cells, Bioorganic & Medicinal Chemistry, vol. 20, Issue 2, pp. 1029-1045, Jan. 15, 2012.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Zlatev, et al., Reversal of siRNA-mediated Gene Silencing in Vivo, Nature Biotechnology, vol. 36, No. 6, pp. 509-511, 2018.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutic Targets in Huntington's Disease, Physiological Reviews, vol. 90, No. 3, pp. 905-981, Jul. 1, 2010.

*sFLT-1 siRNA: Combination (1:1 mixture of siRNA-2283 (sFLT1-i13-targeting) and siRNA-2519 (sFLT1-e15a-targeting)

OPTIMIZED ANTI-FLT1 OLIGONUCLEOTIDE COMPOUNDS FOR TREATMENT OF PREECLAMPSIA AND OTHER ANGIOGENIC DISORDERS

RELATED APPLICATION

This application claims the benefit of U.S. Provisional Patent Application Ser. No. 63/214,224 filed Jun. 23, 2021, the entire disclosure of which is incorporated herein by reference.

STATEMENT REGARDING FEDERALLY SPONSORED RESEARCH OR DEVELOPMENT

This invention was made with government support under Grant No. HD086111 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 14, 2023, is named 728301_UM9-267_ST25.txt and is 7,084 bytes in size.

FIELD OF THE INVENTION

This disclosure relates to novel angiogenic targets and novel oligonucleotide compounds for the treatment of angiogenic disorders (e.g., preeclampsia).

BACKGROUND

Pre-eclampsia (PE) is a serious and progressively fatal complication occurring in 5-8% of pregnancies worldwide and resulting in premature birth as well as increased morbidity and mortality of both the mother and the fetus. Characterized by hypertension and proteinuria, PE can lead to extensive kidney and liver damage, hemolysis, thrombocytopenia and death.

Maternal symptoms of PE are primarily caused by high levels of placental secreted soluble fms-like tyrosine kinase-1 (sFLT1), which is both a diagnostic and prognostic marker of the disease. Studies have shown that sFLT1 is a viable therapeutic target for the treatment of PE.

Previous work has identified siRNAs targeting the major isoforms of sFLT1 to reduce both placental and circulating sFLT1 levels in pregnant mice and non-human primates (Turanov et. al. Nat Biotechnol. 2018 Nov. 19:10.1038/nbt.4297.). However there remains a need to develop siRNAs that are optimized for therapeutic use in pregnant women.

SUMMARY

The present invention is based in part on the discovery of optimized oligonucleotides which target mRNA isoforms encoding sFLT1 proteins and not full length FLT1 (fl-FLT1) protein. The novel oligonucleotides of the invention can be used to treat PE, postpartum PE, eclampsia and/or HELLP syndrome. The novel oligonucleotide sequences of the invention (e.g., small interfering RNAs (siRNAs)) have been engineered to selectively decrease sFLT1 levels without affecting fl-FLT1 by binding to one or more of the sequences that are not present in fl-FLT1, e.g., one or more intronic regions of mRNA encoding one or more sFLT1 proteins. Novel optimized oligonucleotides (e.g., siRNAs) described herein can be preferentially delivered to the placental trophoblasts (the cell type responsible for excess sFLT1 production) using systemic (i.e., intravenous or subcutaneous) delivery to the mother without delivery to the fetus. In certain embodiment, the optimized oligonucleotides described herein retain a high level of silencing efficacy with increased placental tissue accumulation, reduced off-target tissue accumulation, reduced siRNA degradation, reduced toxicity, and a wider therapeutic index.

In some aspects, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 20 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; and (6) a portion of the antisense strand is complementary to a portion of the sense strand.

In another aspect, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 20 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises at least 65% 2'-O-methyl modifications; (9) the nucleotides at any one of more of positions 4, 6, 8, 10, and 14 from the 5' end of the sense strand are not 2'-methoxy-ribonucleotides; and (10) the nucleotides at positions 1-2 from the 5' end of the sense strand are connected to each other via phosphorothioate internucleotide linkages.

In certain embodiments, the nucleotides at positions 2, 4, 5, 6, 8, 10, 12, 14, 16, and 20 from the 5' end of the antisense strand are not 2'-methoxy-ribonucleotides.

In some aspects, the disclosure provides a double stranded RNA (dsRNA), said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; and (5) a portion of the antisense strand is complementary to a portion of the sense strand.

In another aspect, the disclosure provides a double stranded RNA (dsRNA), said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In some aspects, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 18 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; and (6) a portion of the antisense strand is complementary to a portion of the sense strand.

In another aspect, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 18 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises at least 80% 2'-O-methyl modifications; (9) the nucleotides at any one or more of positions 7, 9, and 11 from the 5' end of the sense strand are not 2'-methoxy-ribonucleotides; and (10) the nucleotides at positions 1-2 from the 5' end of the sense strand are connected to each other via phosphorothioate internucleotide linkages.

In certain embodiments, the nucleotides at positions 2, 4, 5, 6, 8, 10, 12, 14, 16, and 18 from the 5' end of the antisense strand are not 2'-methoxy-ribonucleotides.

In certain embodiments, the nucleotides at positions 7, 9, and 11 from the 5' end of the sense strand are not 2'-methoxy-ribonucleotides.

In some aspects, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 70% 2'-O-methyl modifications; (4) the nucleotides at any one or more of positions 2, 4, 5, 6, 8, and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; and (6) a portion of the antisense strand is complementary to a portion of the sense strand.

In another aspect, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 70% 2'-O-methyl modifications; (4) the nucleotides at any one or more of positions 2, 4, 5, 6, 8, and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In certain embodiments, the nucleotides at positions 2, 4, 5, 6, 8, and 14 from the 5' end of the antisense strand are not 2'-methoxy-ribonucleotides.

In some aspects, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 75% 2'-O-methyl modifications; (4) the nucleotides at any one or more of positions 2, 4, 5, 6, and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; and (6) a portion of the antisense strand is complementary to a portion of the sense strand.

In another aspect, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 75% 2'-O-methyl modifications; (4) the nucleotides at any one or more of positions 2, 4, 5, 6, and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In some aspects, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 85% 2'-O-methyl modifications; (4) the nucleotides at any one or more of positions 2 and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; and (6) a portion of the antisense strand is complementary to a portion of the sense strand.

In another aspect, the disclosure provides a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 85% 2'-O-methyl modifications; (4) the nucleotides at any one or more of positions 2 and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In certain embodiments, the antisense strand is 20 nucleotides in length. In certain embodiments, the antisense strand is 21 nucleotides in length. In certain embodiments, the antisense strand is 22 nucleotides in length.

In certain embodiments, the sense strand is 15 nucleotides in length. In certain embodiments, the sense strand is 16 nucleotides in length. In certain embodiments, the sense strand is 18 nucleotides in length. In certain embodiments, the sense strand is 20 nucleotides in length.

In certain embodiments, the dsRNA comprises a double-stranded region of 15 base pairs to 20 base pairs. In certain embodiments, the dsRNA comprises a double-stranded region of 15 base pairs. In certain embodiments, the dsRNA comprises a double-stranded region of 16 base pairs. In certain embodiments, the dsRNA comprises a double-stranded region of 18 base pairs. In certain embodiments, the dsRNA comprises a double-stranded region of 20 base pairs.

In certain embodiments, the dsRNA comprises a blunt-end.

In certain embodiments, the dsRNA comprises at least one single stranded nucleotide overhang.

In certain embodiments, the dsRNA comprises about a 2-nucleotide to 5-nucleotide single stranded nucleotide overhang.

In certain embodiments, the dsRNA comprises 4-16 phosphorothioate internucleotide linkages. In certain embodiments, the dsRNA comprises 8-13 phosphorothioate internucleotide linkages.

In certain embodiments, the sense strand comprises one or more nucleotide mismatches between the antisense strand and the sense strand.

In certain embodiments, the antisense strand comprises a 5' phosphate, a 5'-alkyl phosphonate, a 5' alkylene phosphonate, or a 5' alkenyl phosphonate.

In certain embodiments, the antisense strand comprises a 5' vinyl phosphonate.

In certain embodiments, a functional moiety is linked to the 3' end of the sense strand.

In certain embodiments, the functional moiety comprises a hydrophobic moiety.

In certain embodiments, the hydrophobic moiety is selected from the group consisting of fatty acids, steroids, secosteroids, lipids, gangliosides, nucleoside analogs, endocannabinoids, vitamins, and a mixture thereof.

In certain embodiments, the steroid selected from the group consisting of cholesterol and Lithocholic acid (LCA).

In certain embodiments, the fatty acid selected from the group consisting of Eicosapentaenoic acid (EPA), Docosahexaenoic acid (DHA) and Docosanoic acid (DCA). In some embodiments, the fatty acid is EPA. In some embodiments, the fatty acid is DHA. In some embodiments, the fatty acid is DCA. In some embodiments, the fatty acid is PC-DCA.

In certain embodiments, the vitamin is selected from the group consisting of choline, vitamin A, vitamin E, and derivatives or metabolites thereof.

In certain embodiments, the functional moiety is linked to the sense strand by a linker.

In certain embodiments, the linker is a cleavable linker.

In certain embodiments, the cleavable linker comprises a phosphodiester linkage, a disulfide linkage, an acid-labile linkage, or a photocleavable linkage.

In certain embodiments, the cleavable linker comprises a dTdT dinucleotide with phosphodiester internucleotide linkages.

In certain embodiments, the acid-labile linkage comprises a β-thiopropionate linkage or a carboxydimethylmaleic anhydride (CDM) linkage.

In certain embodiments, the linker comprises a divalent or trivalent linker.

In certain embodiments, the divalent or trivalent linker is selected from the group consisting of:

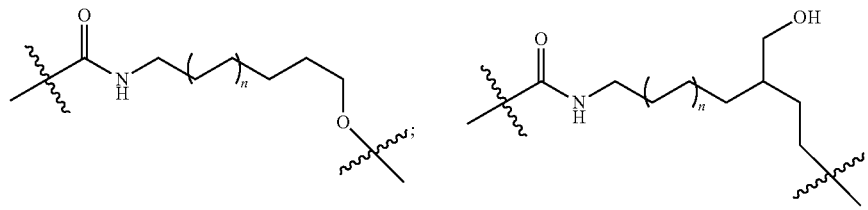

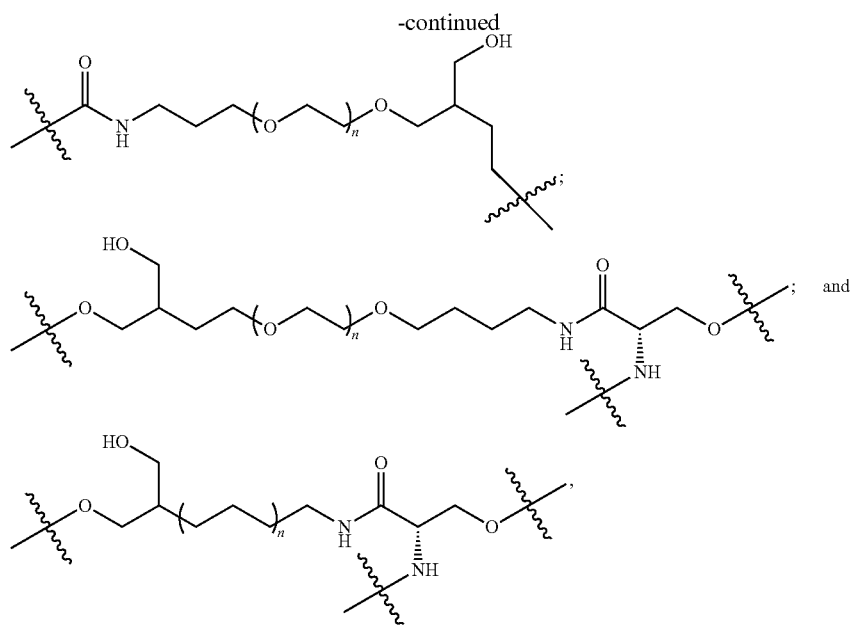

wherein n is 1, 2, 3, 4, or 5.

In certain embodiments, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments, when the linker is a trivalent linker, the linker further links a phosphodiester or phosphodiester derivative.

In certain embodiments, the linker further links a phosphodiester or phosphodiester derivative.

In certain embodiments, the phosphodiester or phosphodiester derivative is selected from the group consisting of:

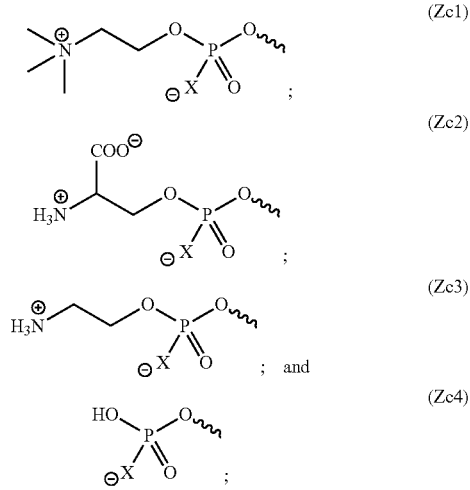

wherein X is O, S or BH$_3$.

In certain embodiments, the nucleotides at positions 1 and 2 from the 3' end of sense strand, and the nucleotides at positions 1 and 2 from the 5' end of antisense strand, are connected to adjacent ribonucleotides via phosphorothioate linkages.

In certain embodiments, the region of complementarity is complementary to at least 15, 16, 17 or 18 contiguous nucleotides of SEQ ID NO: 1 or SEQ ID NO: 2.

In certain embodiments, the region of complementarity contains no more than 3 mismatches with SEQ ID NO: 1 or SEQ ID NO: 2.

In certain embodiments, the region of complementarity is fully complementary to SEQ ID NO: 1 or SEQ ID NO: 2.

In certain embodiments, the antisense strand comprises or consists of the nucleic acid sequence of 5' UAAAUUUG-GAGAUCCGAGAGA 3' (SEQ ID NO: 8) and the sense strand comprises or consists of the nucleic acid sequence of 5' CGGAUCUCCAAAUUUA 3' (SEQ ID NO: 9).

In certain embodiments, the antisense strand comprises or consists of the nucleic acid sequence of 5' UAUAAAUG-GUAGCUAUGAUGA 3' (SEQ ID NO: 10) and the sense strand comprises or consists of the nucleic acid sequence of 5' AUAGCUACCAUUUAUA 3' (SEQ ID NO: 11).

In some embodiments, the disclosure provides a salt of the dsRNA molecule. In some embodiments, the salt comprises a sodium salt or potassium salt. In some embodiments, the salt comprises a pharmaceutically acceptable salt.

In certain embodiments, expression of a sFLT1 protein in a cell or organism is reduced by at least about 20%.

In an aspect, the disclosure provides a method of treating or managing PE, postpartum PE, eclampsia or HELLP syndrome comprising administering to a subject in need of such treatment or management a therapeutically effective amount of the dsRNA described above.

In some aspects, the disclosure provides a method of treating or managing PE comprising administering to a subject in need of such treatment or management a therapeutically effective amount of the dsRNA described above.

In some aspects, the disclosure provides a method of treating or managing postpartum PE comprising administering to a subject in need of such treatment or management a therapeutically effective amount of the dsRNA described above.

In some aspects, the disclosure provides a method of treating or managing eclampsia comprising administering to a subject in need of such treatment or management a therapeutically effective amount of the dsRNA described above.

In some aspects, the disclosure provides a method of treating or managing HELLP syndrome comprising administering to a subject in need of such treatment or management a therapeutically effective amount of the dsRNA described above.

In certain embodiments, the pharmaceutical composition is administered intravenously or subcutaneously.

In certain embodiments, sFLT1 protein expression is reduced in the subject by at least about 20%

In an aspect, the disclosure provides a method of treating one or more symptoms of PE, postpartum PE, eclampsia or HELLP syndrome in a subject in need thereof, comprising administering to the subject the dsRNA described above.

In an aspect, the disclosure provides a method of treating one or more symptoms of an angiogenic disorder in a subject in need thereof, comprising administering to the subject the dsRNA described above.

In certain embodiments, the angiogenic disorder is selected from the group consisting of PE, postpartum PE, eclampsia and HELLP syndrome.

In an aspect, the disclosure provides a pharmaceutical composition comprising: a first dsRNA comprising a first sense strand and a first antisense strand, wherein the first antisense strand comprises a region of complementarily which is substantially complementary to SEQ ID NO: 1, wherein the first dsRNA comprises the dsRNA described above; a second dsRNA comprising a second sense strand and a second antisense strand, wherein the second antisense strand comprises a region of complementarity which is substantially complementary to SEQ ID NO: 2, wherein the second dsRNA comprises the dsRNA described above; and a pharmaceutically acceptable carrier.

In an aspect, the disclosure provides a pharmaceutical composition comprising: a first dsRNA comprising a first sense strand and a first antisense strand, each strand with a 5' end and a 3' end, wherein the first antisense strand comprises a region of complementarity which is substantially complementary to SEQ ID NO: 1; a second dsRNA comprising a second sense strand and a second antisense strand, each strand with a 5' end and a 3' end, wherein the second antisense strand comprises a region of complementarity which is substantially complementary to SEQ ID NO: 2; and a pharmaceutically acceptable carrier, wherein for each of the first dsRNA and second dsRNA: (1) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 20 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises at least 65% 2'-O-methyl modifications; (9) the nucleotides at any one of more of positions 4, 6, 8, 10, and 14 from the 5' end of the sense strand are not 2'-methoxy-ribonucleotides; and (10) the nucleotides at positions 1-2 from the 5' end of the sense strand are connected to each other via phosphorothioate internucleotide linkages.

In some aspects, the disclosure provides a double stranded RNA (dsRNA) molecule, said dsRNA comprising an antisense strand and a sense strand, each strand with a 5' end and a 3' end, wherein: (1) the antisense strand comprises (mU)#(fA)#(mA)(fA)(fU)(fU)(mU)(fG)(mG)(fA)(mG)(fA)(mU)(fC)#(mC)#(fG)#(m A)#(mG)#(mA)#(fG)#(mA) (SEQ ID NO: 12); and (2) the sense strand comprises (mC)#(mG)#(mG)(fA)(mU)(fC)(mU)(fC)(mC)(fA)(mA)(mA)(mU)(fU)#(mU)#(mA) (SEQ ID NO: 13), wherein "m" corresponds to a 2'-O-methyl modification, "f" corresponds to a 2'-fluoro modification, "#" corresponds to a phosphorothioate internucleotide linkage.

In some aspects, the disclosure provides a double stranded RNA (dsRNA) molecule, said dsRNA comprising an antisense strand and a sense strand, each strand with a 5' end and a 3' end, wherein: the antisense strand comprises (mU)#(fA)#(mA)(fA)(fU)(fU)(mU)(fG)(mG)(fA)(mG)(fA)(mU)(fC)#(mC)#(fG)#(m A)#(mG)#(mA)#(fG)#(mA) (SEQ ID NO: 12), wherein "m" corresponds to a 2'-O-methyl modification, "f" corresponds to a 2'-fluoro modification, "#" corresponds to a phosphorothioate internucleotide linkage.

In some aspects, the disclosure provides a double stranded RNA (dsRNA) molecule, said dsRNA comprising an antisense strand and a sense strand, each strand with a 5' end and a 3' end, wherein: the sense strand comprises (mC)#(mG)#(mG)(fA)(mU)(fC)(mU)(fC)(mC)(fA)(mA)(mA)(mU)(fU)#(mU)#(mA) (SEQ ID NO: 13), wherein "m" corresponds to a 2'-O-methyl modification, "f" corresponds to a 2'-fluoro modification, "#" corresponds to a phosphorothioate internucleotide linkage.

In some aspects, the disclosure provides a double stranded RNA (dsRNA) molecule, said dsRNA comprising an antisense strand and a sense strand, each strand with a 5' end and a 3' end, wherein: (1) the antisense strand comprises (mU)#(fA)#(mU)(fA)(fA)(fA)(mU)(fG)(mG)(fU)(mA)(fG)(mC)(fU)#(mA)#(fU)#(m G)#(mA)#(mU)#(fG)#(mA (SEQ ID NO: 14)); and (2) the sense strand comprises (mA)#(mU)#(mA)(fG)(mC)(fU)(mA)(fC)(mC)(fA)(mU)(mU)(mU)(fA)#(mU)#(mA) (SEQ ID NO: 15), wherein "m" corresponds to a 2'-O-methyl modification, "f" corresponds to a 2'-fluoro modification, "#" corresponds to a phosphorothioate internucleotide linkage.

In some aspects, the disclosure provides a double stranded RNA (dsRNA) molecule, said dsRNA comprising an antisense strand and a sense strand, each strand with a 5' end and a 3' end, wherein: the antisense strand comprises (mU)#(fA)#(mU)(fA)(fA)(fA)(mU)(fG)(mG)(fU)(mA)(fG)(mC)(fU)#(mA)#(fU)#(m G)#(mA)#(mU)#(fG)#(mA) (SEQ ID NO: 16), wherein "m" corresponds to a 2'-O-methyl modification, "f" corresponds to a 2'-fluoro modification, "#" corresponds to a phosphorothioate internucleotide linkage.

In some aspects, the disclosure provides a double stranded RNA (dsRNA) molecule, said dsRNA comprising an antisense strand and a sense strand, each strand with a 5' end and a 3' end, wherein: the sense strand comprises (mA)#(mU)#(mA)(fG)(mC)(fU)(mA)(fC)(mC)(fA)(mU)(mU)(mU)(fA)#(mU)#(mA) (SEQ ID NO: 15), wherein "m" corresponds to a 2'-O-methyl modification, "f" corresponds to a 2'-fluoro modification, "#" corresponds to a phosphorothioate internucleotide linkage.

In some embodiments, the antisense strand comprises a 5' vinyl phosphonate.

In some embodiments, the dsRNA comprises a docosanoic acid (DCA) conjugate linked to the 3' end of the sense strand.

In some embodiments, the DCA is linked to the sense strand by a linker.

In some embodiments, the linker is a cleavable linker.

In some embodiments, the cleavable linker comprises a phosphodiester linkage, a disulfide linkage, an acid-labile linkage, or a photocleavable linkage.

In some embodiments, the cleavable linker comprises a dTdT dinucleotide with phosphodiester internucleotide linkages.

In some embodiments, the linker comprises a divalent or trivalent linker.

In some embodiments, the divalent or trivalent linker is selected from the grout, consisting of:

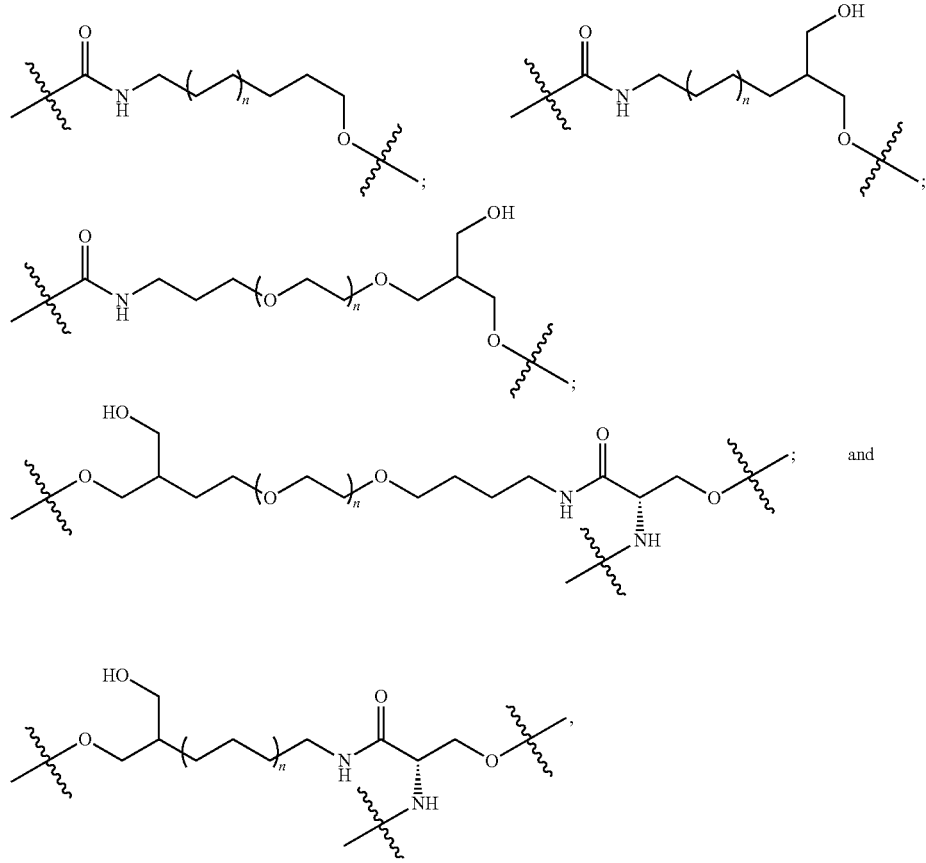

wherein n is 1, 2, 3, 4, or 5.

In some embodiments, when the linker is a trivalent linker, the linker further links a phosphodiester or phosphodiester derivative.

In some embodiments, the phosphodiester or phosphodiester derivative is selected from the group consisting of:

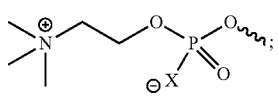
(Zc1)

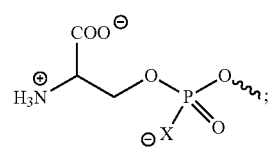
(Zc2)

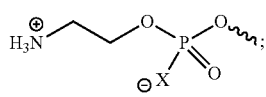
(Zc3) and

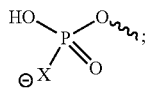
(Zc4)

wherein X is O, S or BH$_3$.

In some aspects, the disclosure provides a double stranded RNA (dsRNA) molecule, said dsRNA comprising an antisense strand and a sense strand, each strand with a 5' end and a 3' end, wherein: (1) the antisense strand comprises V(mU)#(fA)#(mA)(fA)(fU)(fU)(mU)(fG)(mG)(fA)(mG)(fA)(mU)(fC)#(mC)#(fG)#(mA)#(mG)#(mA)#(fG)#(mA) (SEQ ID NO: 17); and (2) the sense strand comprises (mC)#(mG)#(mG)(fA)(mU)(fC)(mU)(fC)(mC)(fA)(mA)(mA)(mU)(fU)#(mU)#(mA)(T)(T)-PCDCA (SEQ ID NO: 18), wherein "m" corresponds to a 2'-O-methyl modification, "f" corresponds to a 2'-fluoro modification, "T" corresponds to a thymidine DNA nucleotide, "#" corresponds to a phosphorothioate internucleotide linkage, "V" corresponds to a 5'-vinylphosphonate, and "PCDCA" corresponds to a 3'-C7-phosphocholine-docosanoic acid conjugate through a phosphate linker.

In some aspects, the disclosure provides a double stranded RNA (dsRNA) molecule, said dsRNA comprising an antisense strand and a sense strand, each strand with a 5' end and a 3' end, wherein: (1) the antisense strand comprises V(mU)#(fA)#(mU)(fA)(fA)(fA)(mU)(fG)(mG)(fU)(mA)(fG)(mC)(fU)#(mA)#(fU)#(mG)#(mA)#(mU)#(fG)#(mA) (SEQ ID NO: 19); and (2) the sense strand comprises (mA)#(mU)#(mA)(fG)(mC)(fU)(mA)(fC)(mC)(fA)(mU)(mU)(mU)(fA)#(mU)#(mA)(T)(T)-PCDCA (SEQ ID NO: 20), wherein "m" corresponds to a 2'-O-methyl modification, "f" corresponds to a 2'-fluoro modification, "T" corresponds to a thymidine DNA nucleotide, "#" corresponds to a phosphorothioate internucleotide linkage, "V" corresponds to a 5'-vinylphosphonate, and "PCDCA" corresponds to a 3'-C7-phosphocholine-docosanoic acid conjugate through a phosphate linker.

In some embodiments, the disclosure provides a salt of the dsRNA molecule. In some embodiments, the salt comprises a sodium salt or potassium salt. In some embodiments, the salt comprises a pharmaceutically acceptable salt.

In some aspects, the disclosure provides a double stranded RNA (dsRNA) molecule, said dsRNA comprising an antisense strand and a sense strand, each strand with a 5' end and a 3' end, wherein:

(1) the antisense strand comprises Formula I, or a salt thereof:

Formula I

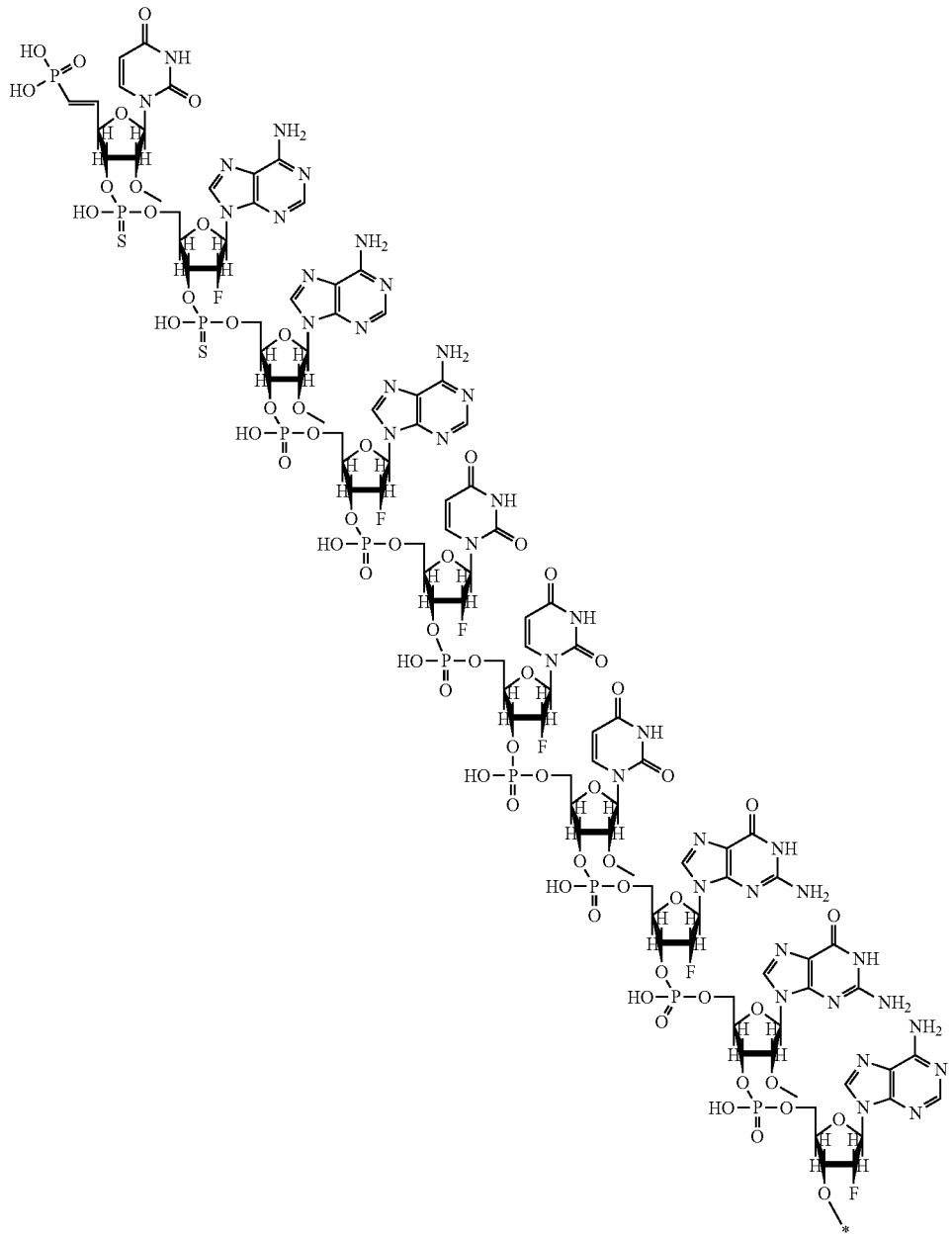

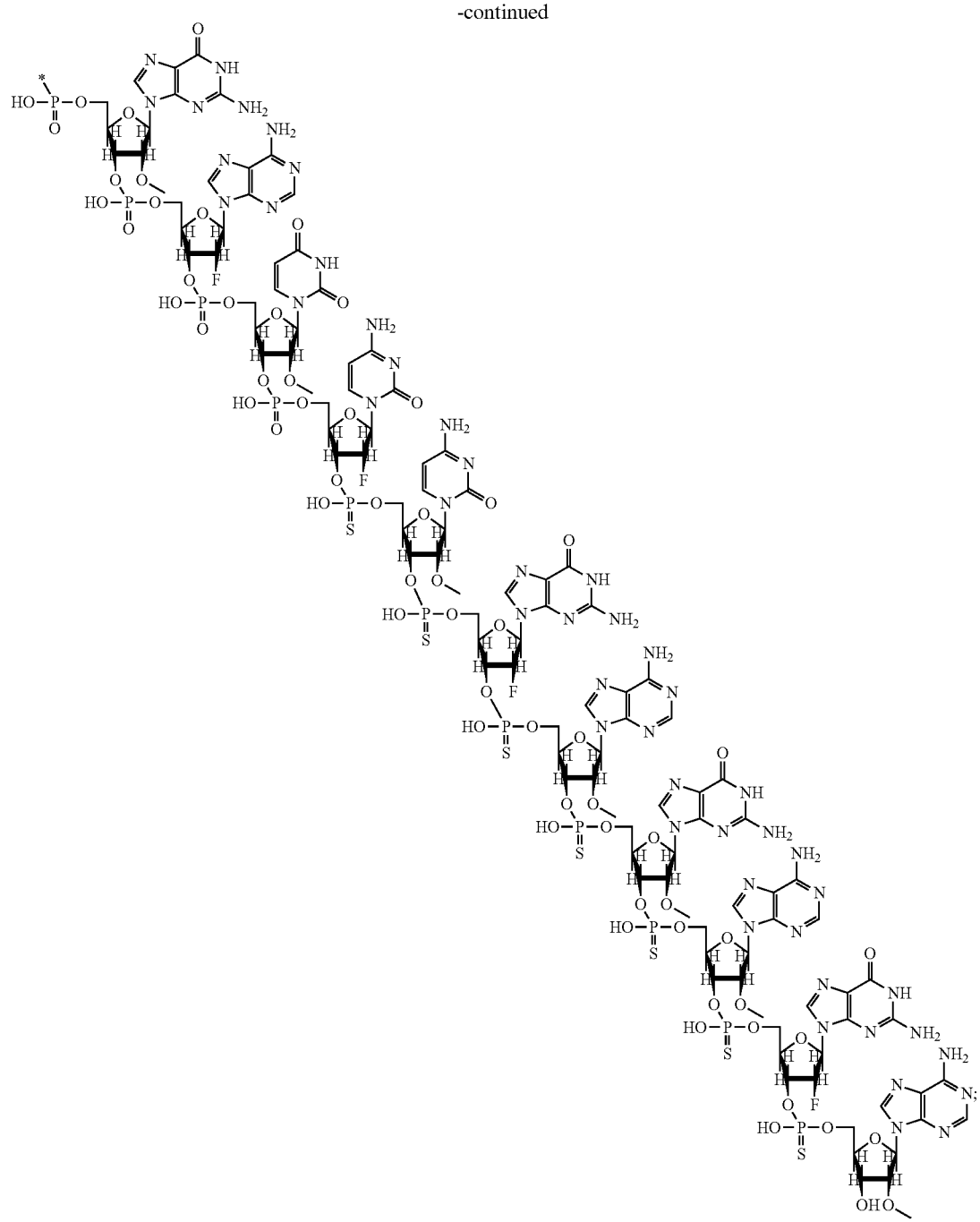
and
(2) the sense strand comprises Formula II, or a salt thereof:

Formula II
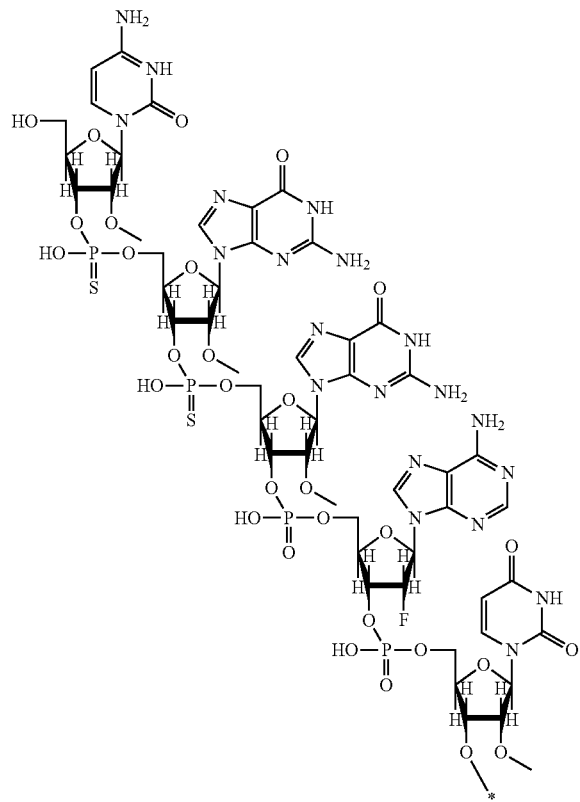
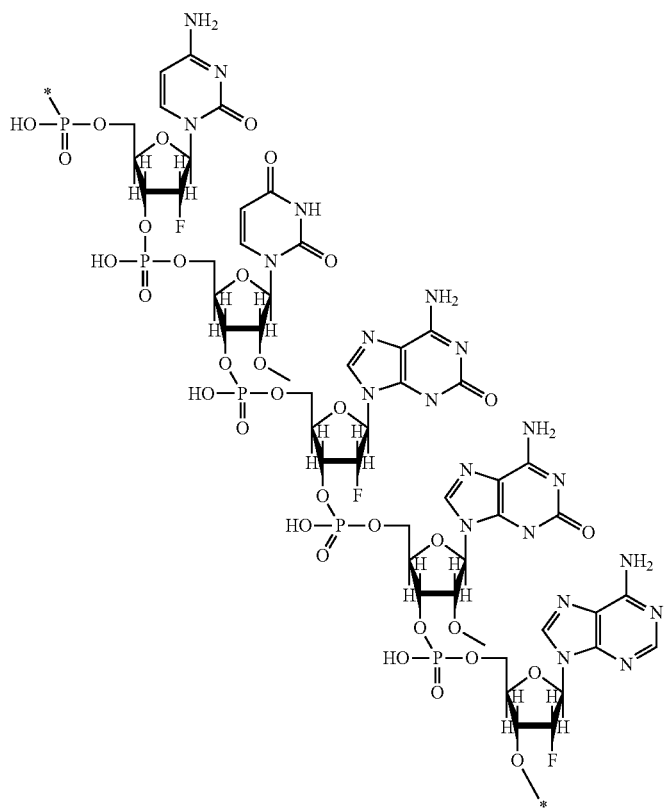

-continued
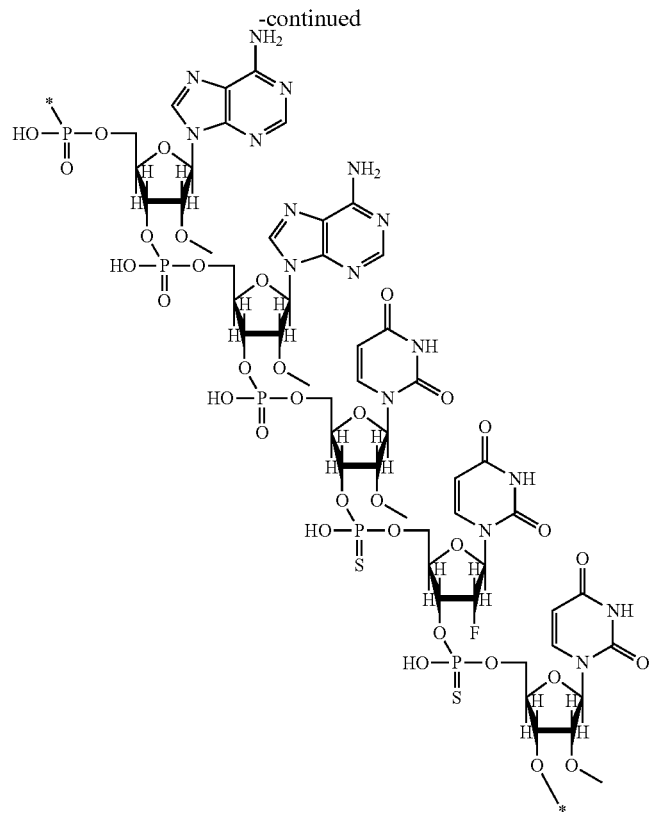
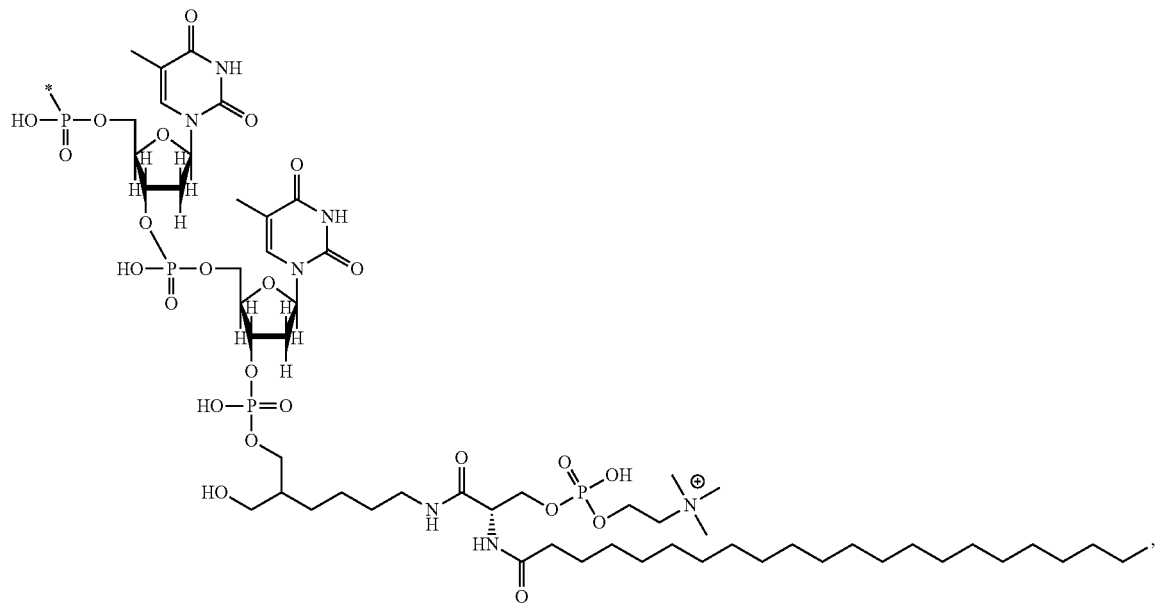
In some aspects, the disclosure provides a double stranded RNA (dsRNA) molecule, said dsRNA comprising an antisense strand and a sense strand, each strand with a 5' end and a 3' end, wherein:
(1) the antisense strand comprises Formula III, or a salt thereof:

Formula III
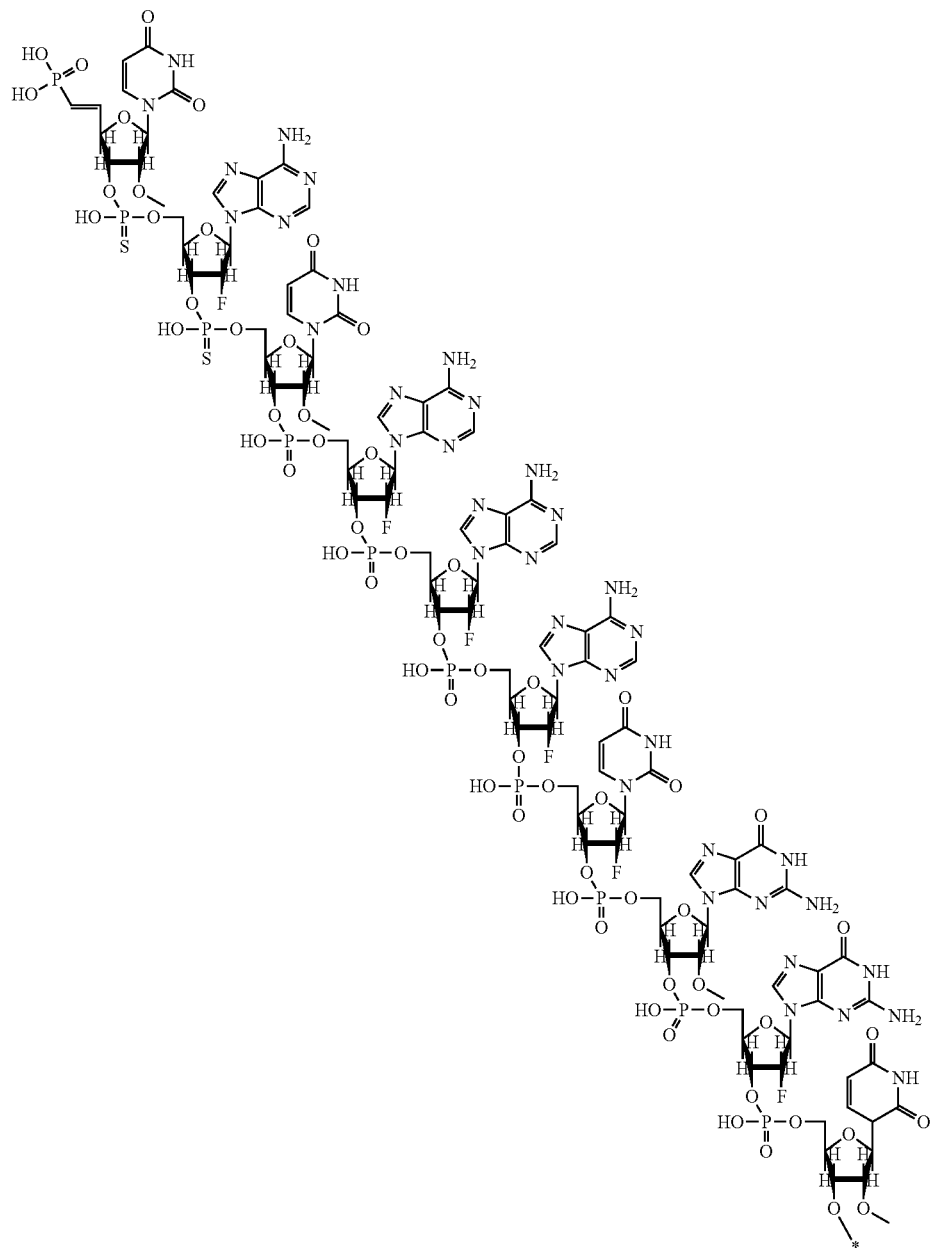

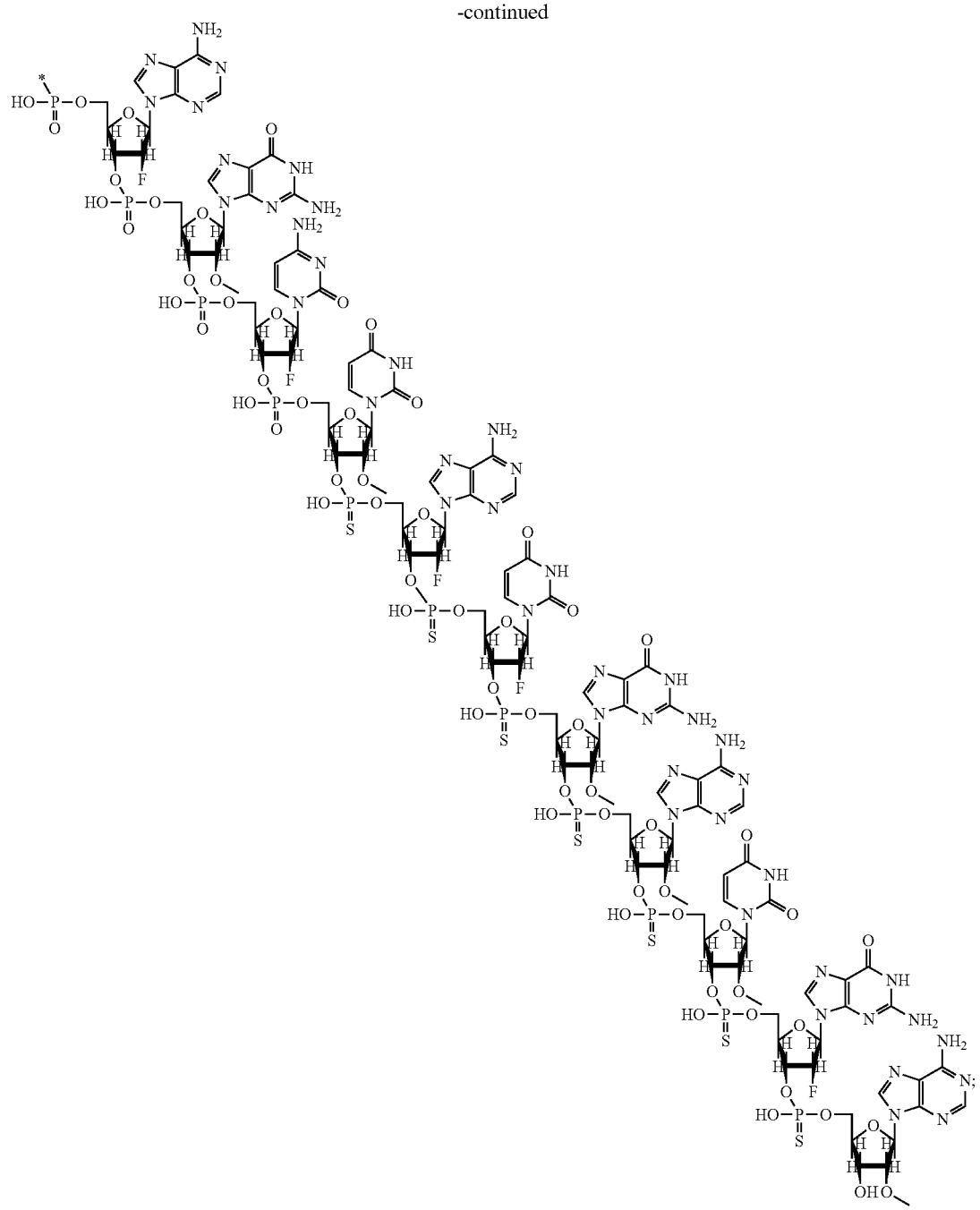
and
(2) the sense strand comprises Formula IV, or a salt thereof:

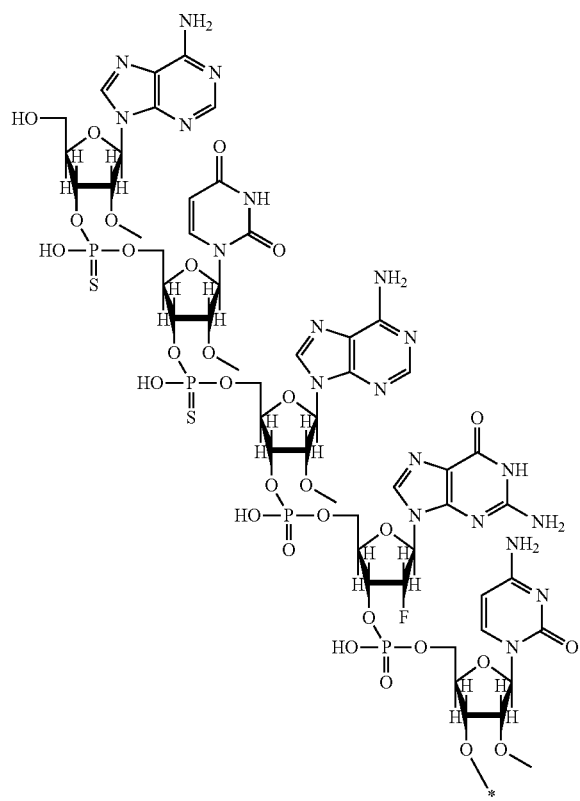
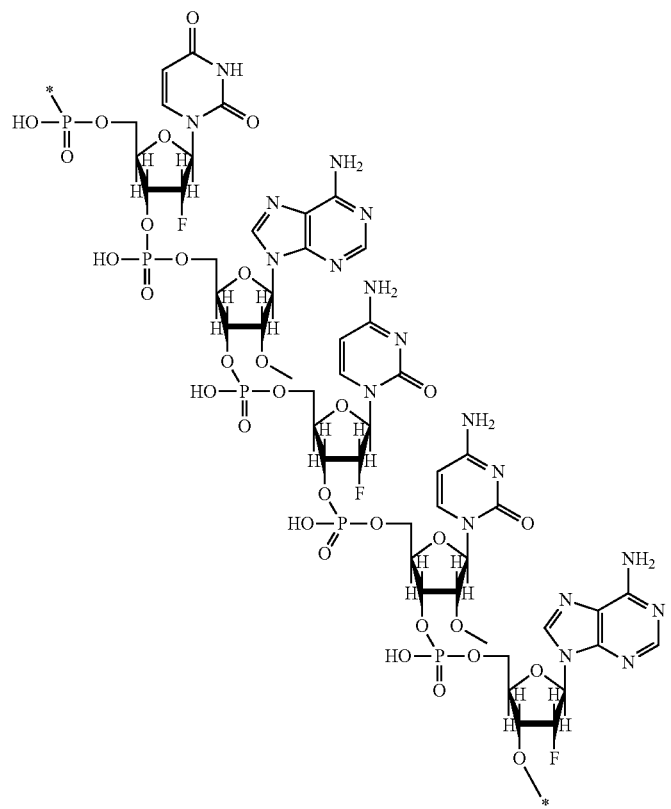

-continued
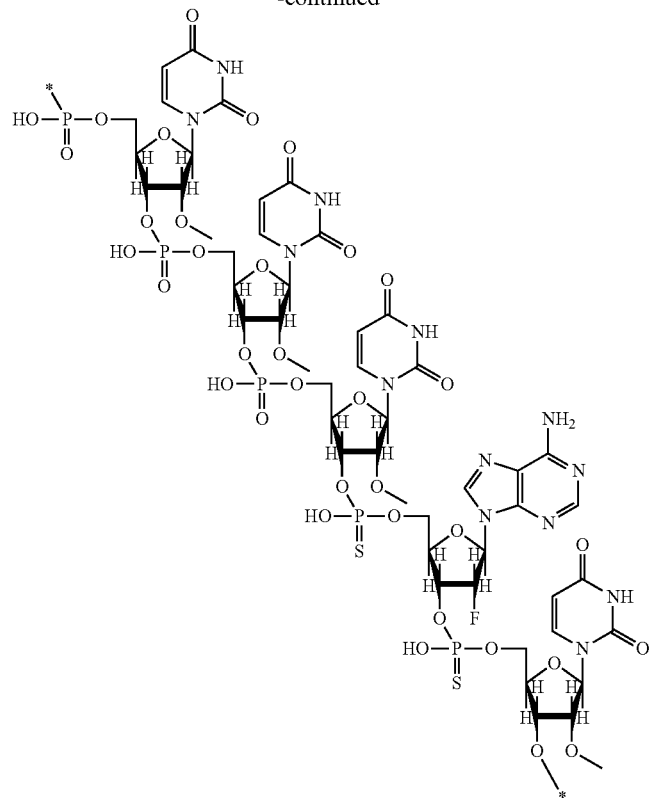
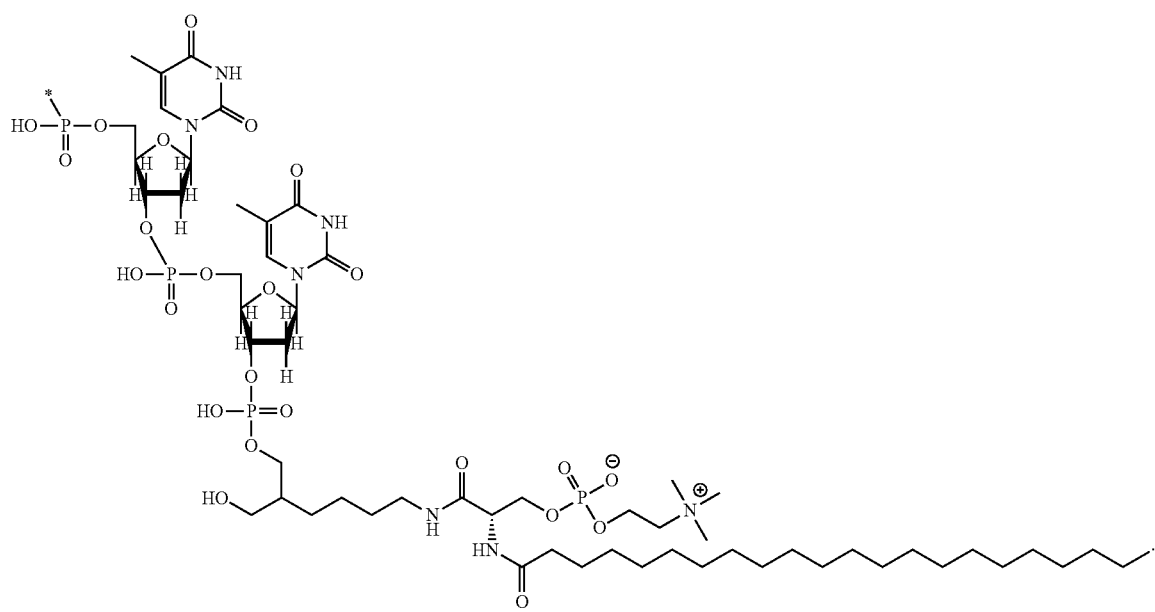
In some aspects, the disclosure provides a double stranded RNA (dsRNA) molecule, said dsRNA comprising an antisense strand and a sense strand, each strand with a 5' end and a 3' end, wherein the antisense strand comprises Formula I, or a salt thereof:

Formula I
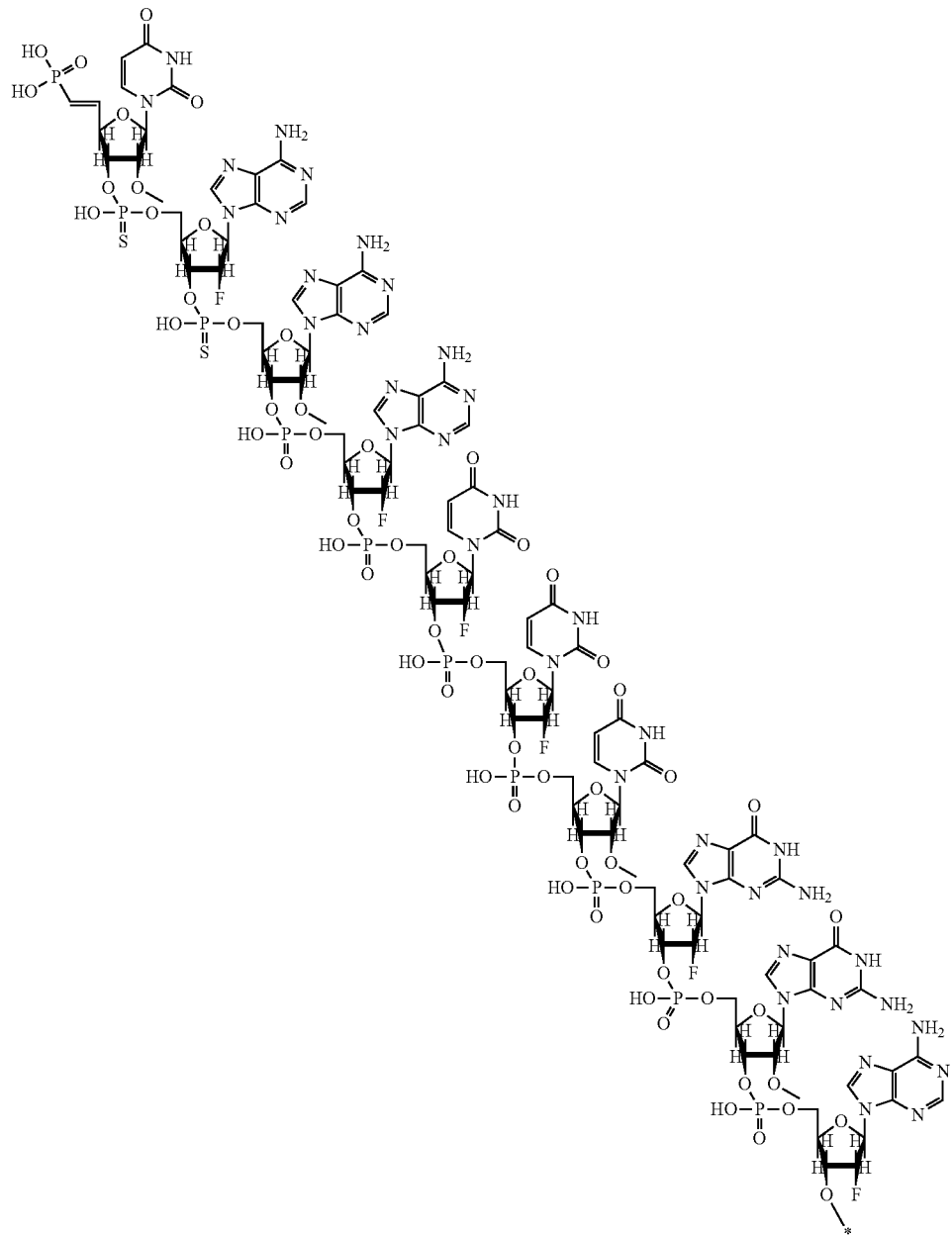

-continued
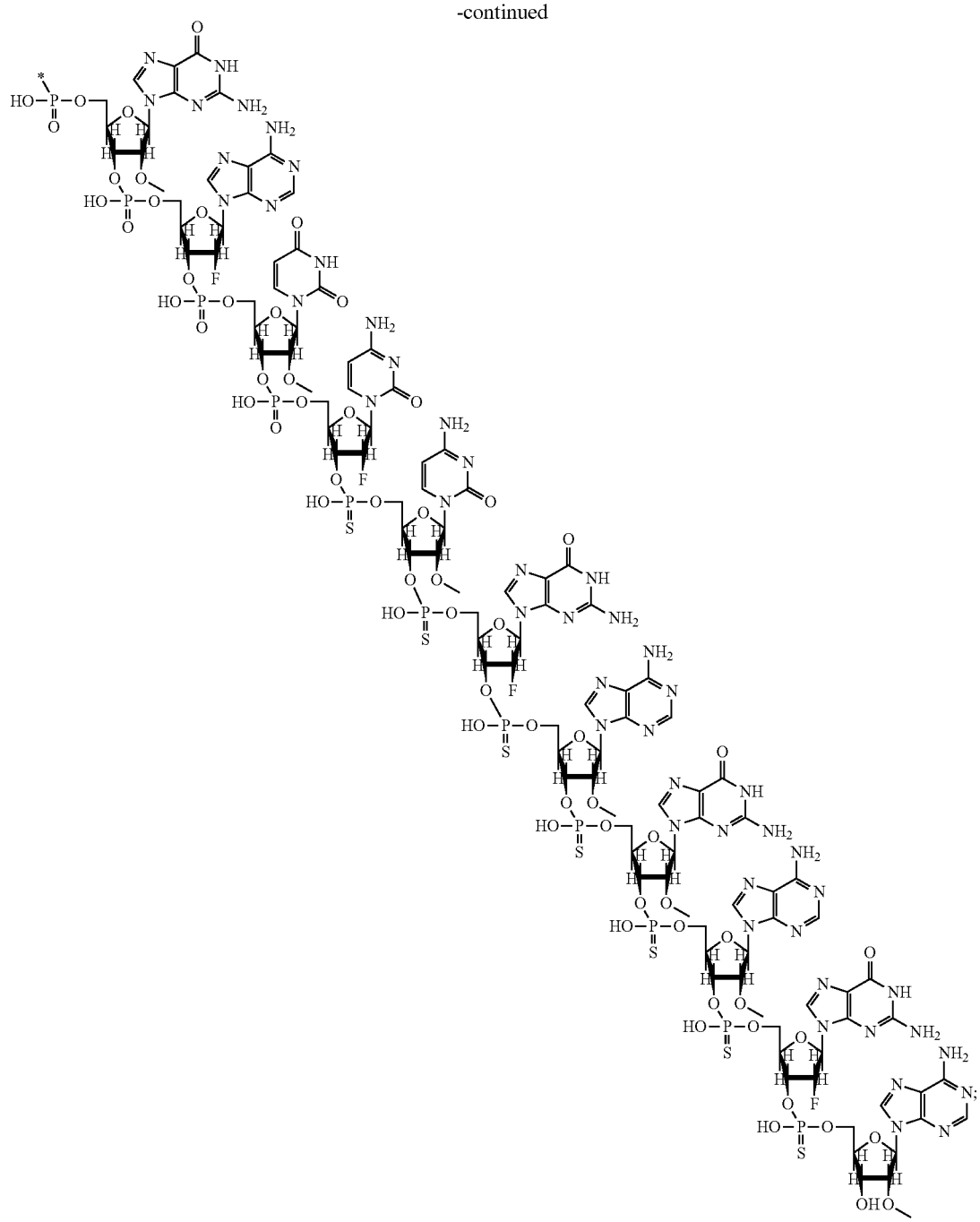
In some aspects, the disclosure provides a double stranded RNA (dsRNA) molecule, said dsRNA comprising an antisense strand and a sense strand, each strand with a 5' end and a 3' end, wherein the sense strand comprises Formula II, or a salt thereof:

Formula II
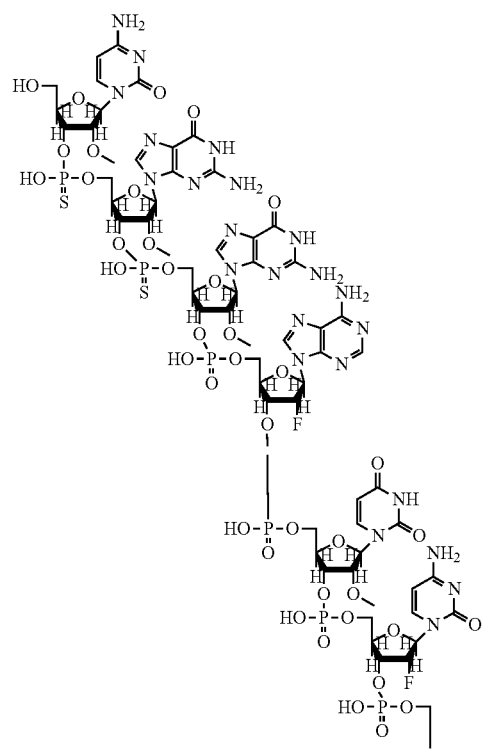
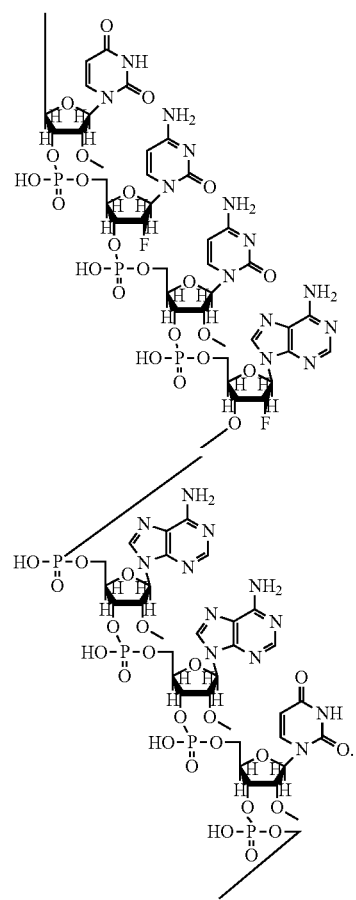

-continued
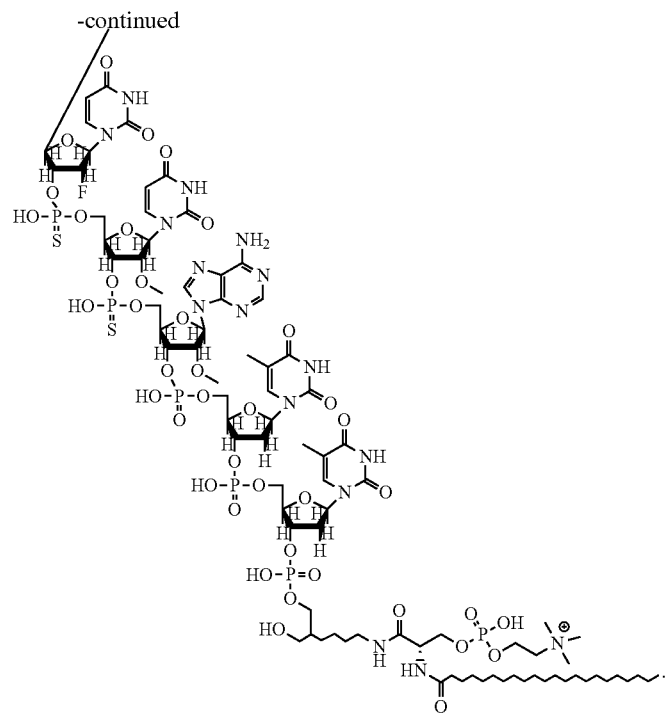
In some aspects, the disclosure provides a double stranded RNA (dsRNA) molecule, said dsRNA comprising an antisense strand and a sense strand, each strand with a 5' end and a 3' end, wherein the antisense strand comprises Formula III, or a salt thereof:
Formula III
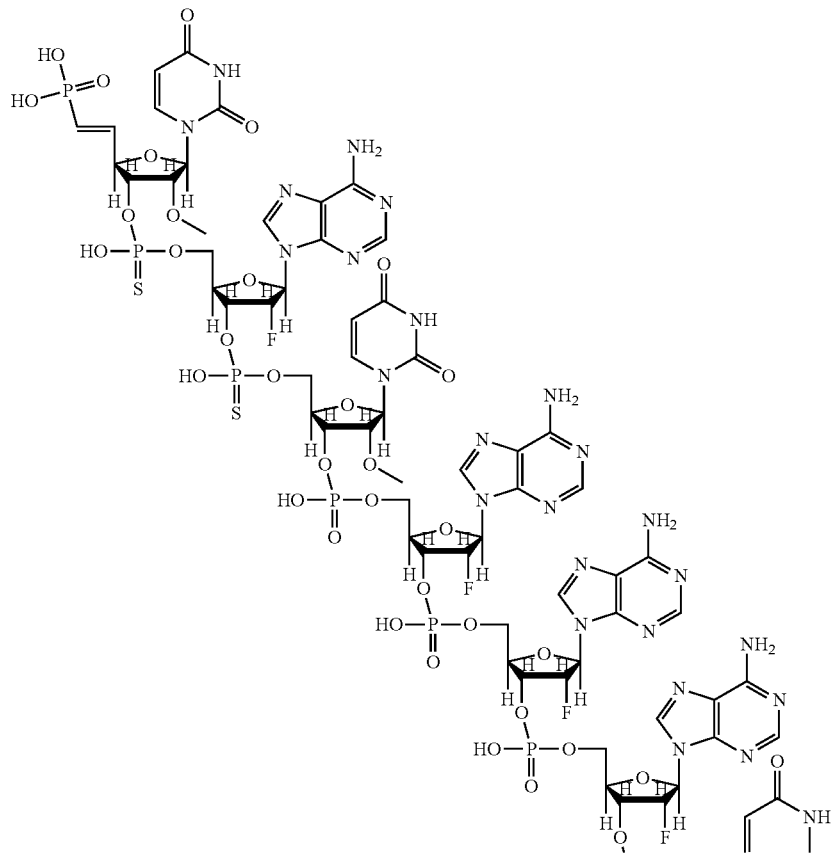

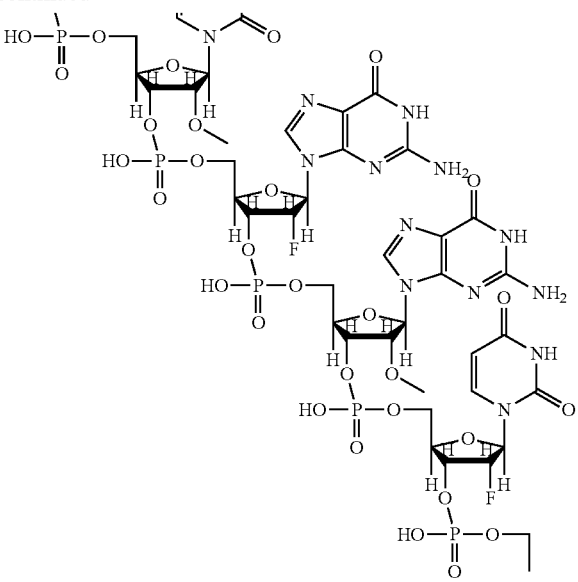
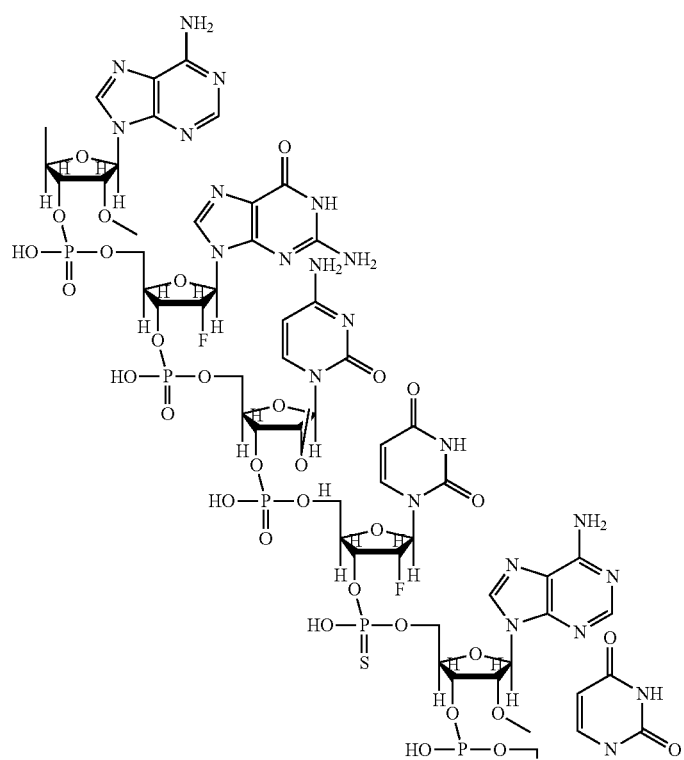

-continued
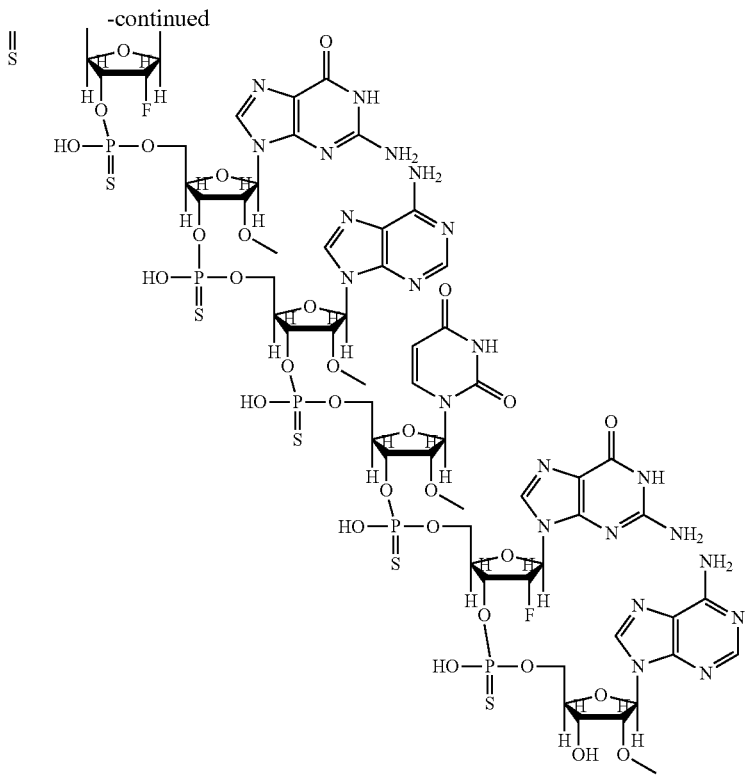
In some aspects, the disclosure provides a double stranded RNA (dsRNA) molecule, said dsRNA comprising an antisense strand and a sense strand, each strand with a 5' end and a 3' end, wherein the sense strand comprises Formula IV, or a salt thereof:
Formula IV
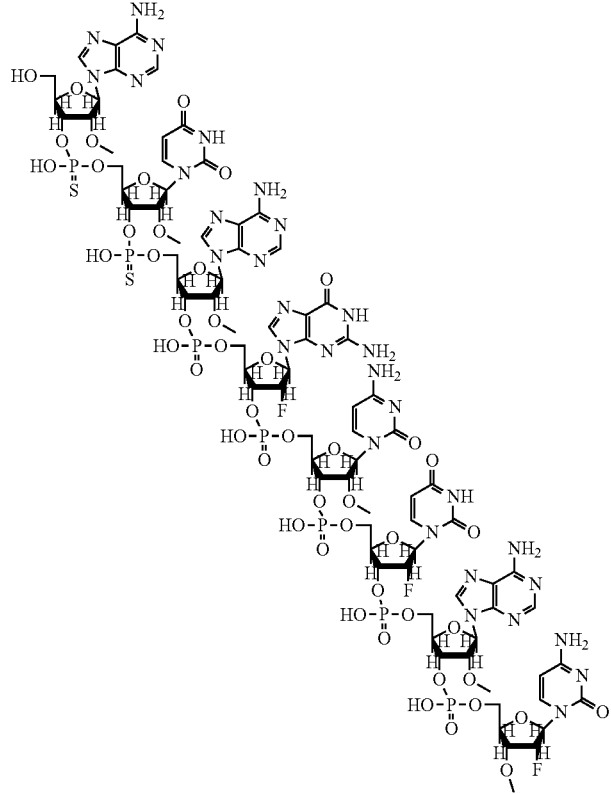

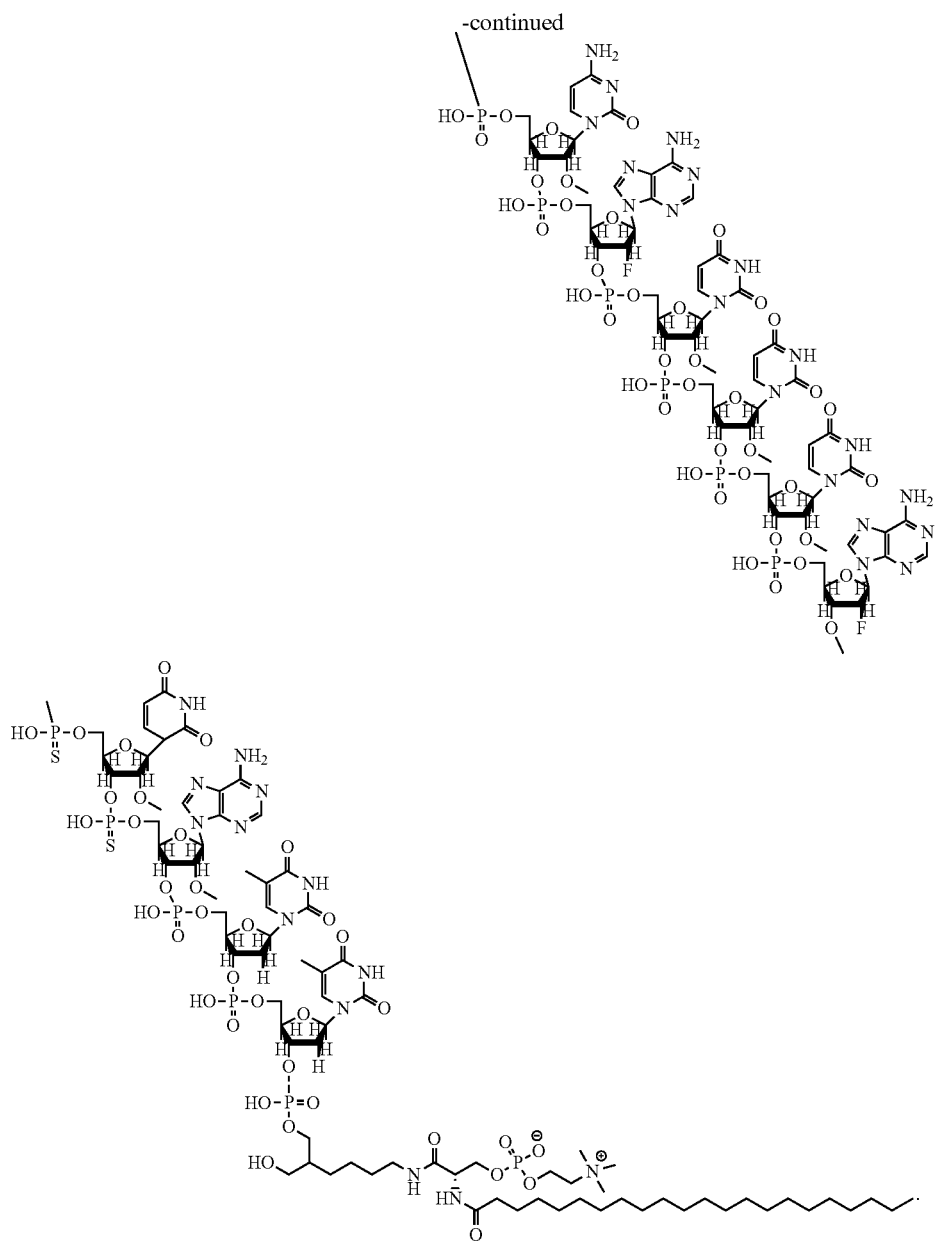

-continued

In some embodiments, the salt comprises a pharmaceutically acceptable salt. In some embodiments, the salt comprises a sodium salt or potassium salt.

In some aspects, the disclosure provides a method of treating or managing PE, postpartum PE, eclampsia or HELLP syndrome comprising administering to a subject in need of such treatment or management a therapeutically effective amount of the dsRNA described above.

In some aspects, the disclosure provides a pharmaceutical composition comprising: a first dsRNA, said first dsRNA comprising an antisense strand and a sense strand, each strand with a 5' end and a 3' end, wherein: (1) the antisense strand comprises V(mU)#(fA)#(mA)(fA)(fU)(fU)(mU)(fG) (mG)(fA)(mG)(fA)(mU)(fC)#(mC)#(fG)#(mA)#(mG)# (mA)#(fG)#(mA) (SEQ ID NO: 17); and (2) the sense strand comprises (mC)#(mG)#(mG)(fA)(mU)(fC)(mU)(fC)(mC) (fA)(mA)(mU)(fU)#(mU)#(mA)(T)(T)-PCDCA (SEQ ID NO: 18); and a second dsRNA, said second dsRNA comprising an antisense strand and a sense strand, each strand with a 5' end and a 3' end, wherein: (1) the antisense strand comprises V(mU)#(fA)#(mU)(fA)(fA)(fA)(mU)(fG) (mG)(fU)(mA)(fG)(mC)(fU)#(mA)#(fU)#(mG)#(mA)# (mU)#(fG)#(mA) (SEQ ID NO: 19); and (2) the sense strand comprises (mA)#(mU)#(mA)(fG)(mC)(fU)(mA)(fC)(mC) (fA)(mU)(mU)(mU)(fA)#(mU)#(mA)(T)(T)-PCDCA (SEQ ID NO: 20), wherein "m" corresponds to a 2'-O-methyl modification, "f" corresponds to a 2'-fluoro modification, "T" corresponds to a thymidine DNA nucleotide, "#" corresponds to a phosphorothioate internucleotide linkage, "V" corresponds to a 5'-vinylphosphonate, and "PCDCA" corresponds to a 3'-C7-phosphocholine-docosanoic acid conjugate through a phosphate linker.

In some aspects, the disclosure provides a pharmaceutical composition comprising: a first dsRNA, said first dsRNA comprising an antisense strand and a sense strand, each strand with a 5' end and a 3' end, wherein:

(1) the antisense strand comprises Formula I, or a salt thereof:
Formula I
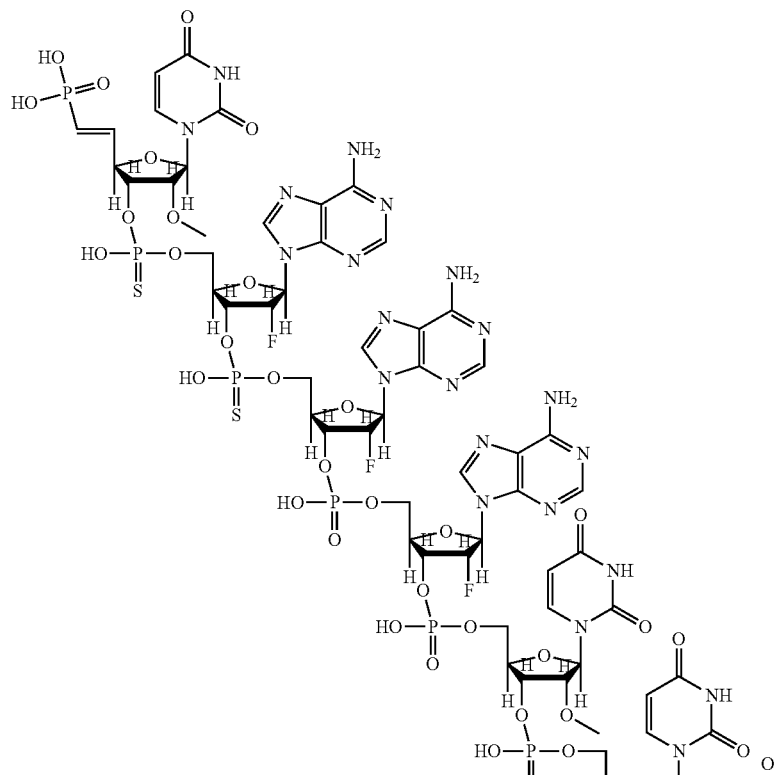
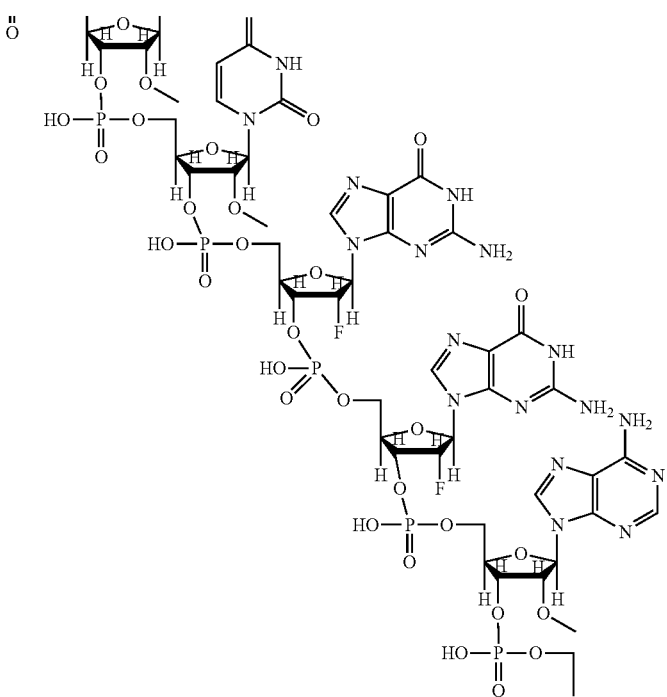

-continued
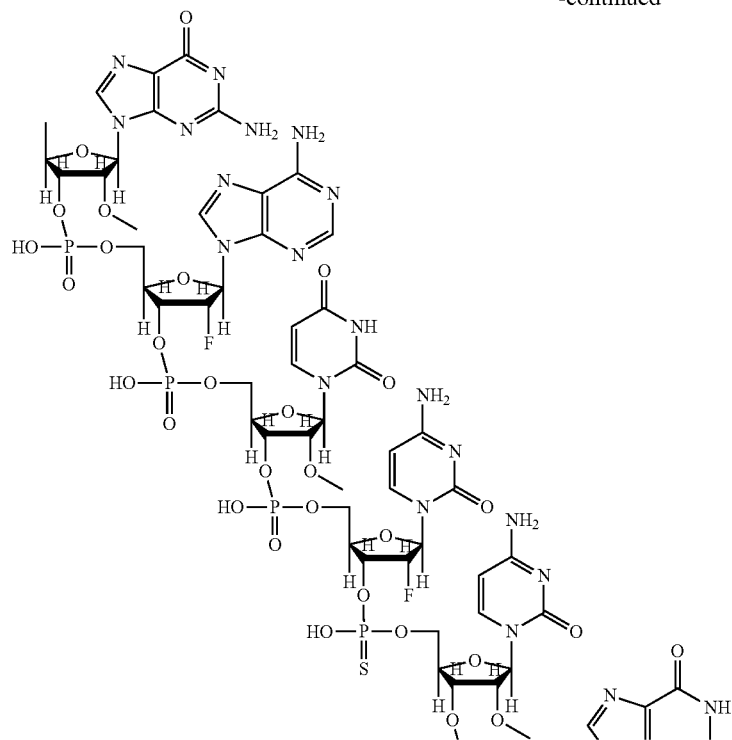
and
(2) the sense strand comprises Formula II, or a salt thereof:
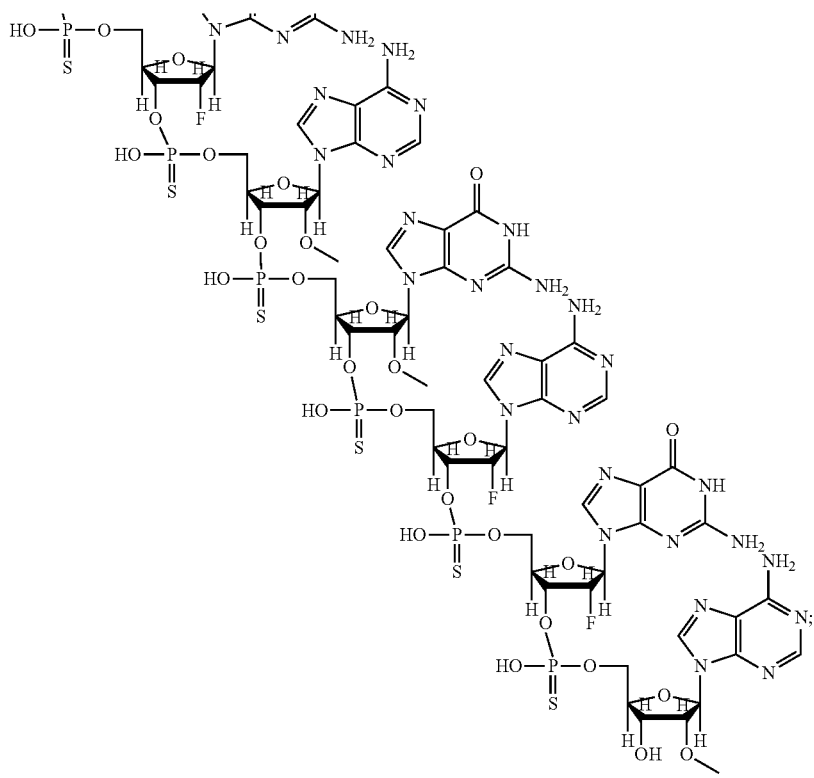

Formula II
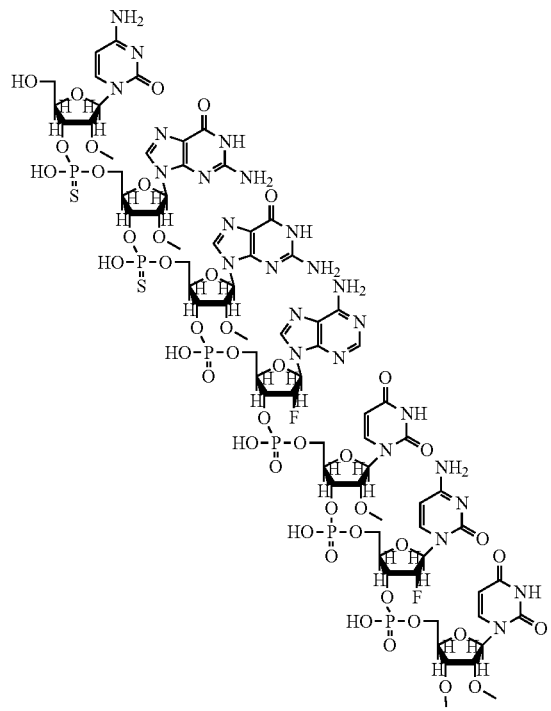
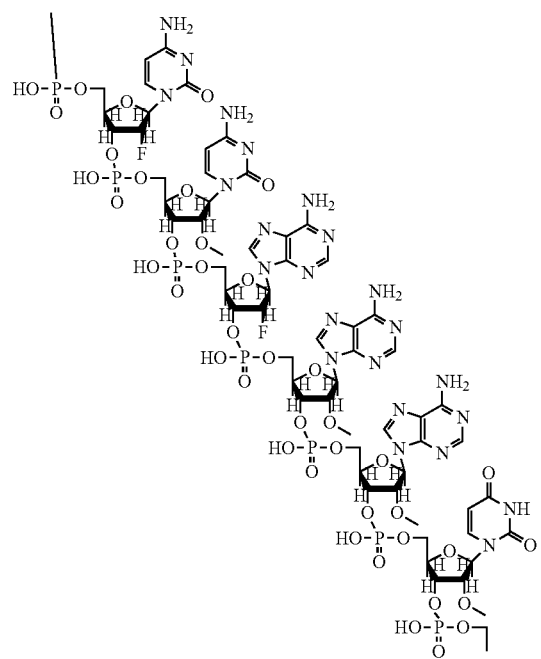

-continued
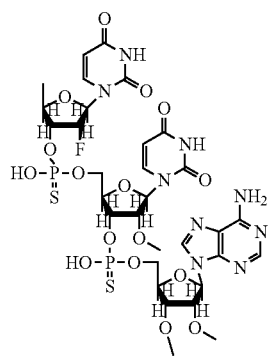
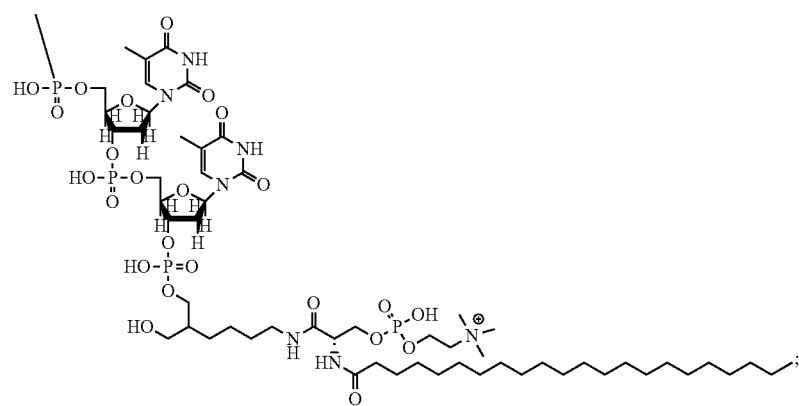
and
a second dsRNA, said second dsRNA comprising an antisense strand and a sense strand, each strand with a 5' end and a 3' end, wherein:
(1) the antisense strand comprises Formula III, or a salt thereof:

Formula III
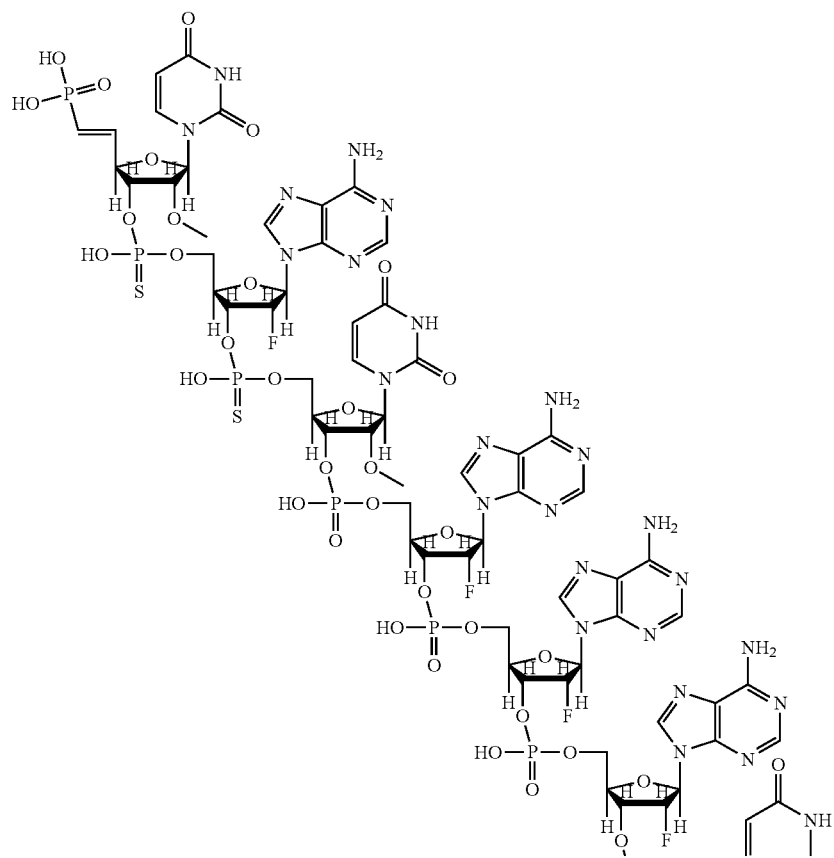
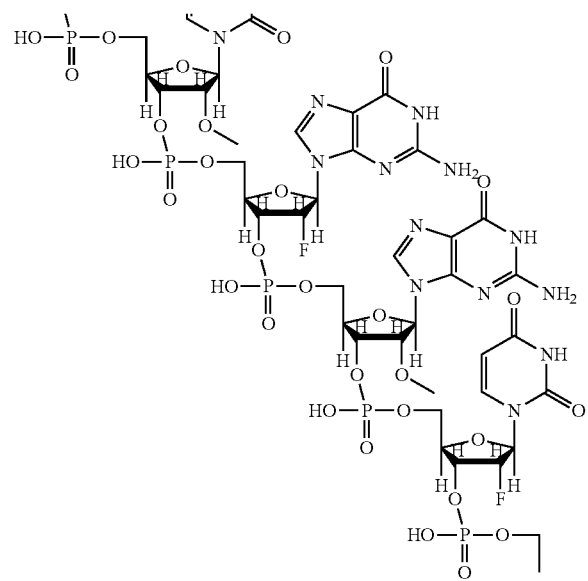

-continued
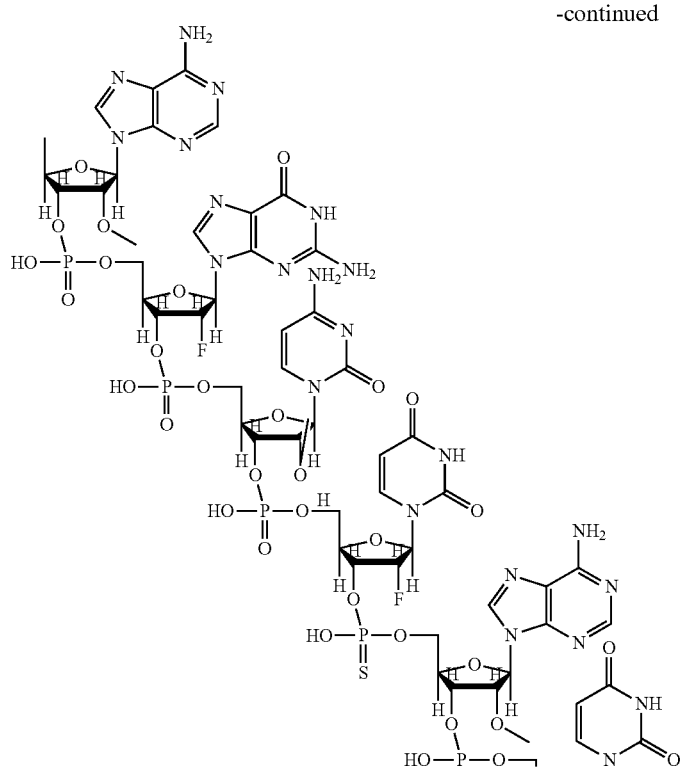
and
(2) the sense strand comprises Formula IV, or a salt thereof:
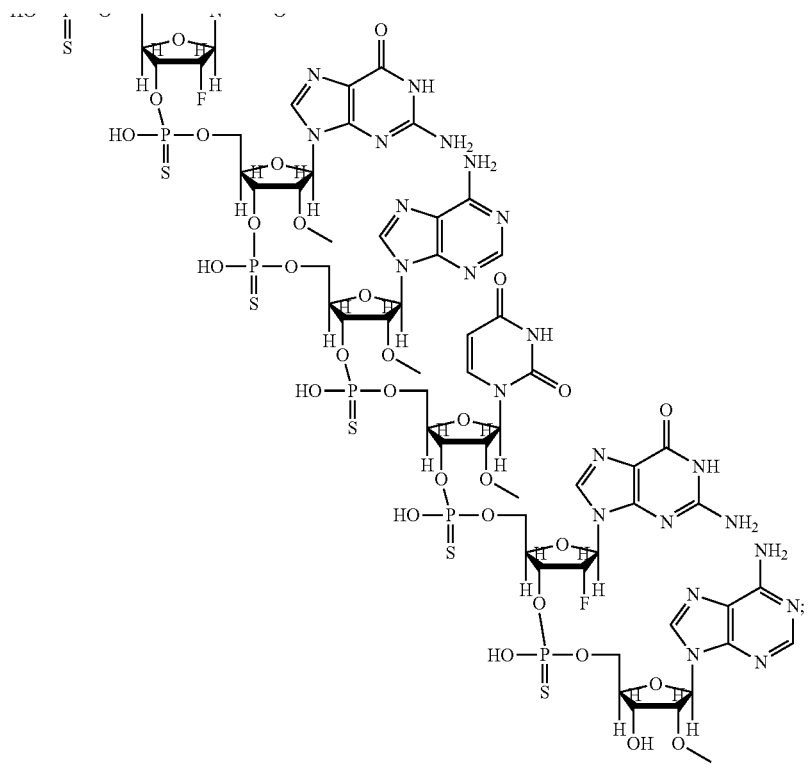

Formula IV
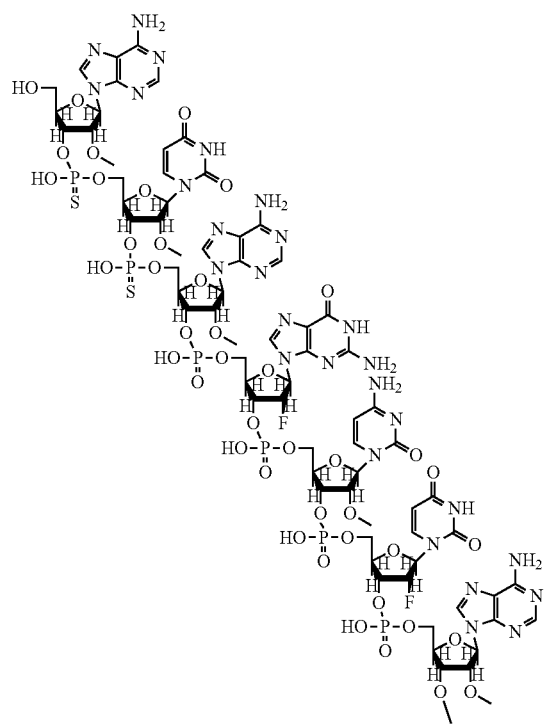
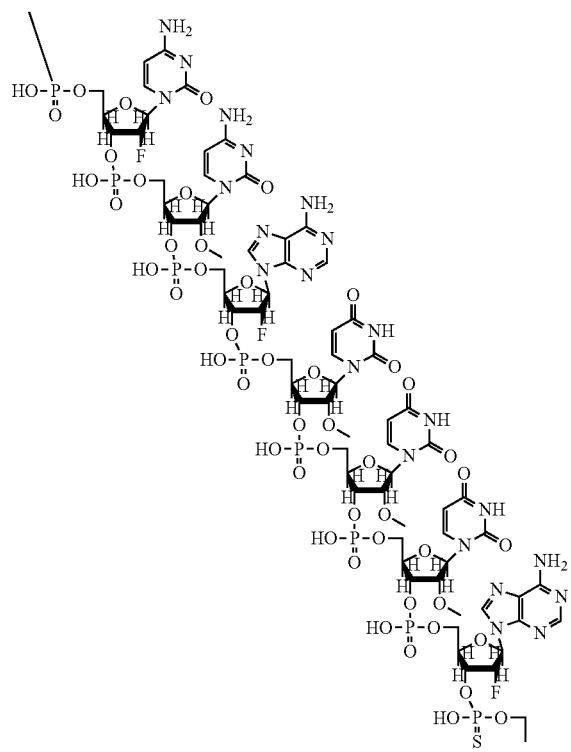

-continued

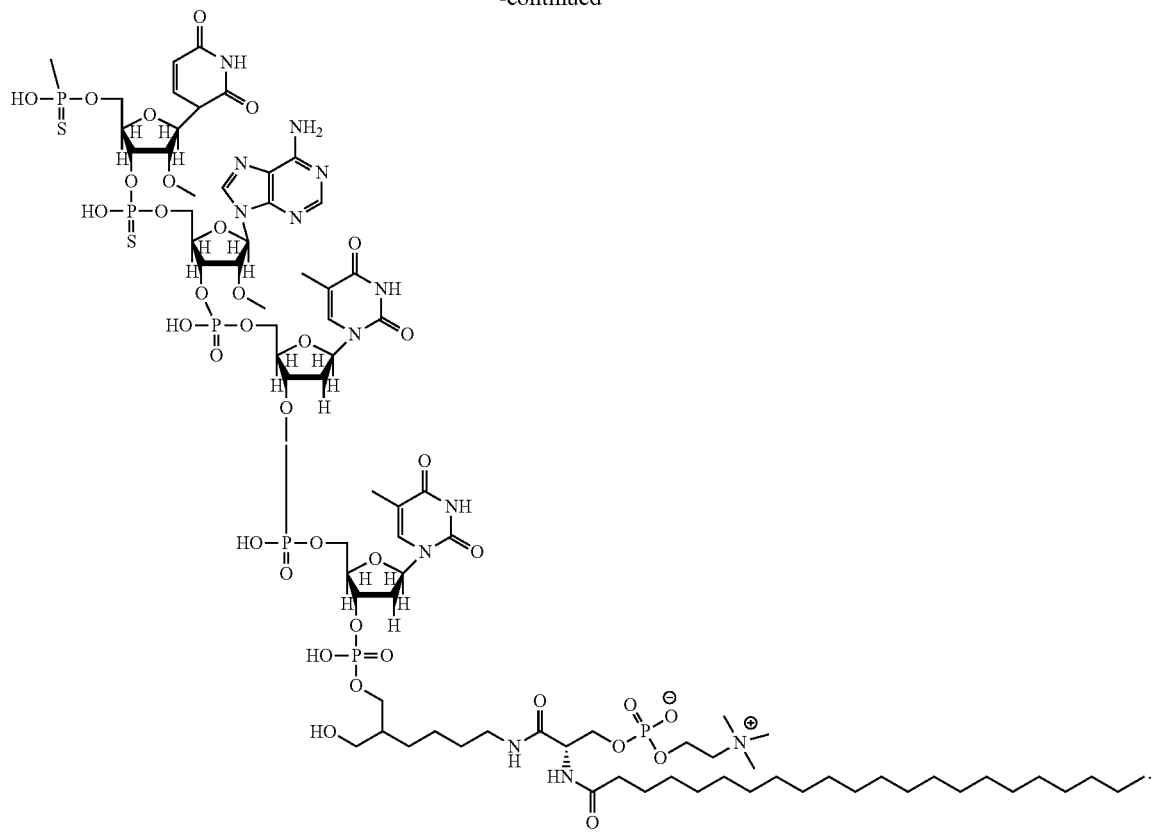

In some embodiments, the salt comprises a pharmaceutically acceptable salt. In some embodiments, the salt comprises a sodium salt or potassium salt.

In some aspects, the disclosure provides a method of treating or managing PE, postpartum PE, eclampsia or HELLP syndrome comprising administering to a subject in need of such treatment or management a therapeutically effective amount of the pharmaceutical composition described above. In some aspects, the disclosure provides a method of treating or managing PE comprising administering to a subject in need of such treatment or management a therapeutically effective amount of the pharmaceutical composition described above. In some aspects, the disclosure provides a method of treating or managing postpartum PE comprising administering to a subject in need of such treatment or management a therapeutically effective amount of the pharmaceutical composition described above. In some aspects, the disclosure provides a method of treating or managing eclampsia comprising administering to a subject in need of such treatment or management a therapeutically effective amount of the pharmaceutical composition described above. In some aspects, the disclosure provides a method of treating or managing HELLP syndrome comprising administering to a subject in need of such treatment or management a therapeutically effective amount of the pharmaceutical composition described above.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 1A depicts schematics of the 2'OMe-rich siRNA chemical modifications patterns. FIG. 1B depicts dose response curves and a summary table of the siRNAs targeting human flt1. HeLa cells treated with siRNAs at concentrations shown for 72 hours. mRNA levels measured using the Dual-Glo® Luciferase Assay System and calculated as percentage of untreated control (C). Table of FIG. 1B—Max. KD (%)—maximum percent target mRNA knockdown with top treatment dose of siRNA, IC50—half maximal inhibitory concentration, AUC—area under the dose response curve, p-value—significance.

FIG. 2A depicts tissue fluorescent images of Cy3-labelled siRNAs conjugated with various functional moieties in liver, kidney, and placental tissue. FIG. 2B depicts guide strand accumulation, quantified after 48 hours by PNA hybridization assay (n=3). p-values describe statistically significant differences between each compound and the cholesterol-conjugated compound (One-way ANOVA;  p<0.01; * p<0.001; non-significant differences not marked). NOC—no conjugate, Chol—cholesterol, DCA—docosanoic acid, PC-DCA—phosphocholine-docosanoic acid, DHA—docosahexanoic acid, PC-DHA—phosphocholine-docosahexanoic acid, DIO—di-branched oligonucleotide.

FIG. 3A shows the gating scheme used to quantify Cy3 intensity of specific cell populations in the bone marrow in FIG. 3B-FIG. 3D. FIG. 3B shows the frequency distribution histogram of Cy3 fluorescence intensity (left) and bar graphs of Cy3 median fluorescence intensity (right) of bone marrow neutrophils 24 h post injection of siRNA variants. FIG. 3C shows the frequency distribution histogram of Cy3 fluorescence intensity (left) and bar graphs of Cy3 median fluorescence intensity (right) of bone marrow granulocytes 24 h post injection of siRNA variants. FIG. 3D shows the frequency distribution histogram of Cy3 fluorescence intensity (left) and bar graphs of Cy3 median fluorescence intensity (right) of bone marrow monocytes 24 h post injection of siRNA variants. (n=3, mean±SD) p-values describe statistically significant differences between compounds (One-way ANOVA; * p<0.05; non-significant differences not marked).

FIG. 4A depicts schematic representations of the chemical pattern of siRNA compounds injected and the chemical structures of 5' moieties tested. FIG. 4B depicts sFlt1-i13 mRNA levels in placenta on E18 were measured using Quantigene 2.0 RNA Assay. Levels were normalized to Flt1 and presented as percentage of PBS control (n=5, mean±SD). FIG. 4C depicts the amount of siRNA accumulation in the placenta on E18 measured using PNA hybridization assay (n=5). p-values describe statistically significant differences between compounds (One-way ANOVA;  p<0.01;  p<0.0001; non-significant differences not marked). FIG. 4D depicts sFlt1-i13 mRNA levels in placenta on E18 measured using Quantigene 2.0 RNA Assay. Levels were normalized to Flt1 and presented as percentage of PBS control (n=6, mean±SD). FIG. 4E depicts the amount of siRNA accumulation in the placenta on E18 measured using PNA hybridization assay (n=6). p-values describe statistically significant differences between compounds (One-way ANOVA;  p<0.01; **** p<0.0001; non-significant differences not marked. Unpaired t-test; # p<0.05; #### p<0.0001). FIG. 4F depicts average mouse pup number, average pup weight, and average placental weight from control and treated pregnant mice.

FIG. 6 discloses SEQ ID NOS 8-11, respectively, in order of appearance.

FIG. 8A depicts the treatment scheme with the RUPP rat model, receiving a combination of two siRNA, (1:1 mixture of siRNA-2283 (sFlt1-i13-targeting) and siRNA-2519 targeting)). FIG. 8B depicts maternal blood pressure and placental weights in the treated and control rats. FIG. 8C depicts fetal absorption and fetal weight in the treated and control rats.

FIG. 9 discloses SEQ ID NOS 21-24, respectively, in order of appearance.

FIG. 10A depicts the antisense strand and FIG. 10B depicts the sense strand. FIG. 10 discloses SEQ ID NOS 17-18, respectively, in order of appearance.

FIG. 11A depicts the antisense strand and FIG. 11B depicts the sense strand. FIG. 11 discloses SEQ ID NOS 25-26, respectively, in order or appearance.

DETAILED DESCRIPTION

Figure 1A:
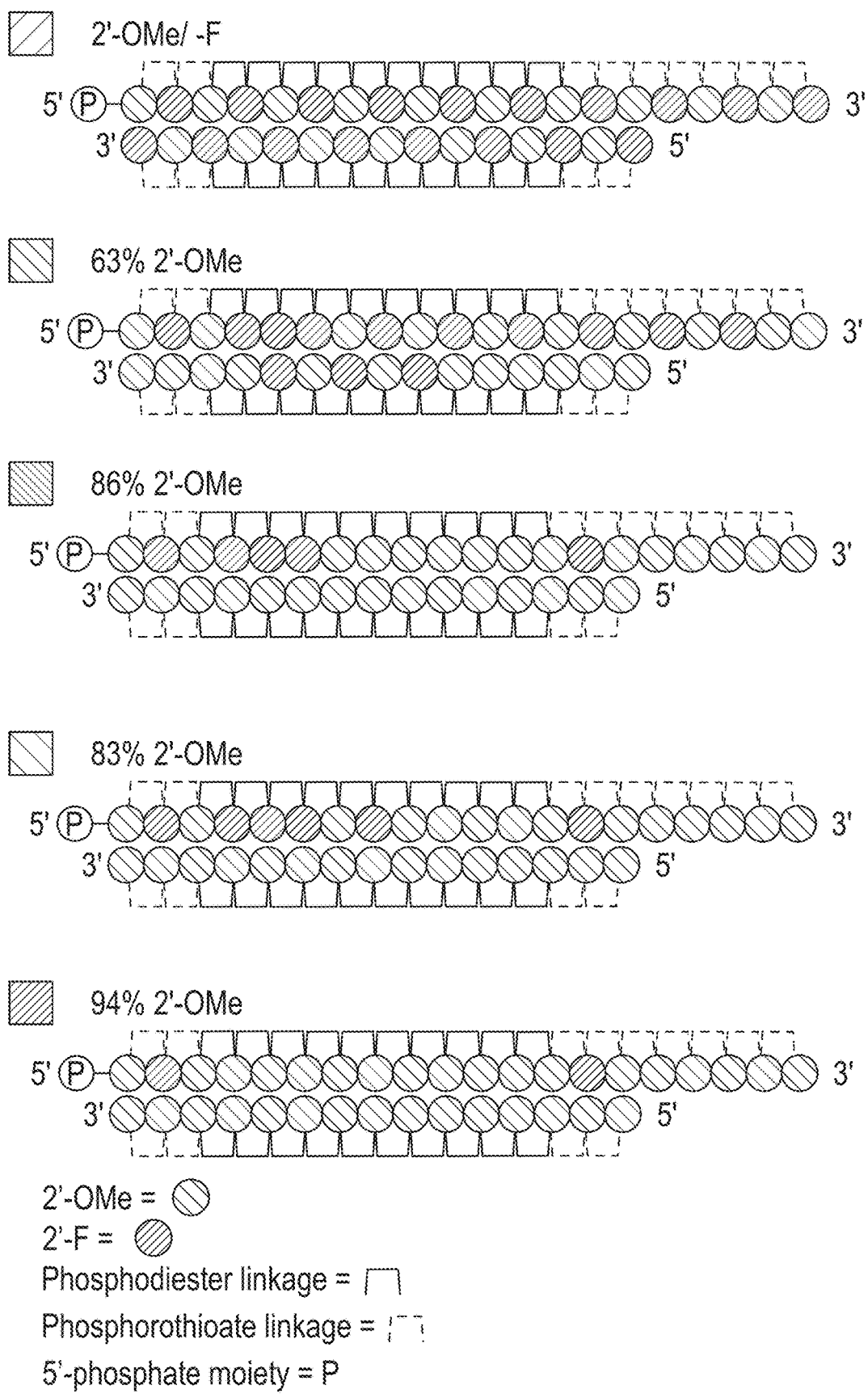
FIG. 1A-FIG. 1B depicts the silencing efficacy of several 2'OMe-rich siRNA chemical modifications patterns.

Novel angiogenic targets (e.g., PE target sequences, e.g., intron sequences of sFlt1 mRNAs) are provided. Also provided are novel siRNAs that selectively target intronic regions of mRNAs encoding angiogenic targets (e.g., sFLT1 proteins). Methods of treating angiogenic disorders, e.g., PE, postpartum PE, eclampsia and/or HELLP, are also provided.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

By "alteration" is meant a change (increase or decrease) in the expression levels of a gene, mRNA or polypeptide as detected by standard art known methods such as those described herein. As used herein, an increase or decrease includes a 10% change in expression levels, a 25% change, a 40% change, or a 50% or greater change in expression levels. In certain embodiments, an increase or decrease is a change in expression levels of between about 30% and about 50% or between about 30% and about 40%. "Alteration" can also indicate a change (increase or decrease) in the biological activity of any of the mRNAs or polypeptides of the invention (e.g., sFlt1 (e.g., sFlt1-i13 short, sFlt1-i13 long and/or sFlt1-i15a (also known as sFlt1-e15a)). Examples of biological activity for sFlt-1 include one or more clinical symptoms of PE or eclampsia. As used herein, an increase or decrease includes a 10% change in biological activity, preferably a 25% change, more preferably a 40% change, and most preferably a 50% or greater change in biological activity. In certain preferred embodiments, an increase or decrease is a change in expression levels of between about 30% and about 50% or between about 30% and about 40%.

Certain embodiments of the invention are directed to the treatment of one or more angiogenic disorders. By "treatment of an angiogenic disorder" is meant use of an oligonucleotide (e.g., an siRNA) of the invention in a pharmaceutical composition for the treatment of diseases involving the physiological and pathological processes of neovascularization, vasculogenesis and/or angiogenesis. As such, these pharmaceutical compositions are useful for treating diseases, conditions and disorders that require inhibition of neovascularization, vasculogenesis or angiogenesis, including but not limited to cancer tumor growth and metastasis, neoplasm, ocular neovascularization (including macular degeneration, diabetic retinopathy, ischemic retinopathy, retinopathy of prematurity, choroidal neovascularization), rheumatoid arthritis, osteoarthritis, chronic asthma, septic shock, inflammatory diseases, synovitis, bone and cartilage destruction, pannus growth, osteophyte formation, osteomyelitis, psoriasis, obesity, haemangioma, Kaposi's sarcoma, atherosclerosis (including atherosclerotic plaque rupture), endometriosis, warts, excess hair growth, scar keloids, allergic edema, dysfunctional uterine bleeding, follicular cysts, ovarian hyperstimulation, endometriosis, osteomyelitis, inflammatory and infectious processes (hepatitis, pneumonia, glumerulonephtritis), asthma, nasal polyps, transplantation, liver regeneration, leukomalacia, thyroiditis, thyroid enlargement, lymphoproliferative disorders, haematologic malignancies, vascular malformations, pre-eclampsia, eclampsia and/or HELLP syndrome. In some embodiments, the disease or disorder is preeclampsia. In some embodiments, the disease or disorder is postpartum preeclampsia. In some embodiments, the disease or disorder is eclampsia. In some embodiments, the disease or disorder is HELLP syndrome.

By "preeclampsia" ("PE") is meant the multi-system disorder that is characterized by hypertension with proteinuria or edema, or both, and one or more of glomerular dysfunction, brain edema, liver edema, or coagulation abnormalities due to pregnancy or the influence of a recent pregnancy. PE generally occurs after the 20th week of gestation. PE is generally defined as some combination of the following symptoms: (1) a systolic blood pressure (BP) >140 mmHg and a diastolic BP>90 mmHg after 20 weeks gestation (generally measured on two occasions, 4-168 hours apart), (2) new onset proteinuria (1+ by dipstick on urinalysis, >300 mg of protein in a 24-hour urine collection, or a single random urine sample having a protein/creatinine ratio>v0.3), and (3) resolution of hypertension and proteinuria by 12 weeks postpartum.

Severe PE is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In PE, hypertension and proteinuria generally occur within seven days of each other. In severe PE, severe hypertension, severe proteinuria and HELLP syndrome (Hemolysis, Elevated Liver enzymes, Low Platelets) or eclampsia can occur simultaneously or only one symptom at a time.

Occasionally, severe PE can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "HELLP" syndrome is meant a group of symptoms that occur in pregnant woman characterized by hemolysis, elevated liver enzymes, and low platelet count. HELLP syndrome is thought to be a variant of PE, but it may be an entity of its own.

In certain aspects, PE includes postpartum PE. Postpartum PE is a rare condition that occurs when a woman has high blood pressure and excess protein in her urine soon after childbirth. Postpartum PE typically develops within 48 hours of childbirth. However, postpartum PE sometimes develops up to six weeks after childbirth, which is known as late postpartum PE. Signs and symptoms of postpartum PE and late postpartum PE are typically similar to those of PE that occurs during pregnancy and may include one or any combination of the following: high blood pressure (i.e., 140/90 mm Hg or greater; proteinuria; severe headaches; changes in vision, including temporary loss of vision, blurred vision or light sensitivity; swelling of the face and limbs; upper abdominal pain, usually under the ribs on the right side; nausea or vomiting; and decreased urination; sudden weight gain, typically more than 2 pounds (0.9 kilogram) a week.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 grams (5 lbs. 8 oz.) or below the 10th percentile for gestational age according to U.S. tables of birth weight for gestational age by race, parity, and infant sex (Zhang and Bowes, Obstet. Gynecol. 86:200-208, 1995). These low birth weight babies are also referred to as "small for gestational age (SGA)." PE is a condition known to be associated with IUGR or SGA.

Certain embodiments of the invention are directed to the treatment of one or more kidney disorders. By "treatment of a kidney disorder" is meant use of an oligonucleotide (e.g., an siRNA) of the invention in a pharmaceutical composition for the treatment of diseases, conditions or disorders associated with the kidney. Diseases, conditions or disorders associated with the kidney include, but are not limited to, Chronic Kidney Disease (CKD) (stages 1-5 with stage 1 being the mildest and usually causing few symptoms and stage 5 being a severe illness with poor life expectancy if untreated (stage 5 CKD is often called end stage renal disease, end stage renal failure, or end-stage kidney disease, chronic kidney failure or chronic renal failure), and Acute Renal Failure (ARF) (caused by traumatic injury with blood loss, sudden reduction of blood flow to the kidneys, damage to the kidneys from sepsis, obstruction of urine flow, damage from certain drugs or toxins, pregnancy complications (e.g., eclampsia, PE and/or HELLP syndrome) and the like).

Certain embodiments of the invention are directed to the treatment of one or more liver disorders. By "treatment of a liver disorder" is meant use of an oligonucleotide (e.g., an siRNA) of the invention in a pharmaceutical composition for the treatment of diseases, conditions or disorders associated with the liver. Diseases, conditions or disorders associated with the liver include, but are not limited to, fascioliasis, hepatitis (e.g., viral hepatitis, alcoholic hepatitis autoimmune hepatitis, hereditary hepatitis and the like), alcoholic liver disease (including alcoholic fatty liver disease, alcoholic hepatitis, and alcoholic cirrhosis), non-alcoholic fatty liver disease, steatohepatitis, non-alcoholic cirrhosis, primary liver cancer (e.g., hepatocellular carcinoma, cholangiocarcinoma, angiosarcoma, hemangiosarcoma and the like), primary biliary cirrhosis, primary sclerosing, centrilobular necrosis, Budd-Chiari syndrome, hemochromatosis, Wilson's disease, alpha 1-antitrypsin deficiency, glycogen storage disease type II, transthyretin-related hereditary amyloidosis, Gilbert's syndrome, biliary atresia, alpha-1 antitrypsin deficiency, Alagille syndrome, progressive familial intrahepatic cholestasis, and the like.

By "therapeutic amount" is meant an amount that when administered to a patient suffering from PE or eclampsia is sufficient to cause a qualitative or quantitative reduction in the symptoms of PE or eclampsia as described herein. A "therapeutic amount" can also mean an amount that when administered to a patient or subject suffering from PE or eclampsia is sufficient to cause a reduction in the expression levels of one or more sFLT1 proteins (e.g., one or more of sFLT1-i13 short, sFLT1-i13 long and sFLT1-i15a) as measured by one or more of the assays described herein.

By "subject" is meant a mammal, including, but not limited to, a human or non-human mammal, such as non-human primates or other animals such as, e.g., bovine, equine, canine, ovine, feline, murine and the like. Included in this definition are pregnant, post-partum and non-pregnant mammals.

By "soluble FLT1 (sFLT1)" (also known as sVEGF-R1) is meant a soluble form of the FLT1 receptor that has sFLT1 biological activity (e.g., sFLT1-i13 short, sFLT1-i13 long and/or sFLT1-i15a (also known as sFLT1-e15a)). The biological activity of an sFLT1 polypeptide may be assayed using any standard method, for example, by assaying for one or more clinical symptoms of PE, postpartum PE, eclampsia and/or HELLP, by assaying sFLT1 mRNA and/or protein levels, by assaying sFLT1 binding to VEGF and the like. sFLT1 proteins lack the transmembrane domain and the cytoplasmic tyrosine kinase domain of the FLT1 receptor. sFLT1 proteins can bind to VEGF and P1GF bind with high affinity, but cannot induce proliferation or angiogenesis and are therefore functionally different from the FLT1 and KDR receptors. sFLT1 was initially purified from human umbilical endothelial cells and later shown to be produced by trophoblast cells in vivo. As used herein, sFLT1 includes any sFLT1 family member or isoform, e.g., sFLT1-i13 (e.g., sFLT1-i13 short and/or sFLT1-i13 long (sFLT1 v1), sFLT1-i15a (sFLT1 v2), sFLT1-e15a, sFLT1 v3, sFLT1 v4 and the like.

The sequence of the sFLT1-i13 short isoform is:
(SEQ ID NO: 5)
GTGAGCACTGCAACAAAAAGGCTGTTTTCTCTCGGATCTCCA

AATTTAAAAGCACAAGGAATGATTGTACCACACAAAGTAATG

TAAAACATTAAAGGACTCATTAAAAAGTAA.

The sequence of the sFLT1-U3 long isoform is:
(SEQ ID NO: 6)
GAAGAAAGAAATTACAATCAGAGGTGAGCACTGCAACAAAAA

GGCTGTTTTCTCTCGGATCTCCAAATTTAAAAGCACAAGGAA

TGATTGTACCACACAAAGTAATGTAAAACATTAAAGGACTCA

TTAAAAAGTAACAGTTGTCTCATATCATCTTGATTTATTGTC

ACTGTTGCTAACTTTCAGGCTCGGAGGAGATGCTCCTCCCAA

AATGAGTTCGGAGATGATAGCAGTAATAATGAGACCCCCGGG

CTCCAGCTCTGGGCCCCCCATTCAGGCCGAGGGGGCTGCTCC

GGGGGGCCGACTTGGTGCACGTTTGGATTTGGAGGATCCCTG

CACTGCCTTCTCTGTGTTTGTTGCTCTTGCTGTTTTCTCCTG

CCTGATAAACAACAACTTGGGATGATCCTTTCCATTTTGATG

CCAACCTCTTTTTATTTTTAAGCGGCGCCCTATAGT.

The sequence of the sFLT1-i15a
(also known as sFLT1-e15d) isoform
is:
(SEQ ID NO: 7)
AACTGTATACATCAACGTCACCATCGTCATCGTCATCATCAC

CATTGTCATCATCATCATCATCGTCATCATCATCATCATCAT

AGCTATCATCATTATCATCATCATCATCATCATCATAGC

TACCATTTATTGAAAACTATTATGTGTCAACTTCAAAGAACT

TATCCTTTAGTTGGAGAGCCAAGACAATCATAACAATAACAA

ATGGCCGGGCATGGTGGCTCACGCCTGTAATCCCAGCACTTT

GGGAGGCCAAGGCAGGTGGATCATTTGAGGTCAGGAGTCCAA

GACCAGCCTGACCAAGATGGTGAAATGCTGTCTCTATTAAAA

ATACAAAATTAGCCAGGCATGGTGGCTCATGCCTGTAATGCC

AGCTACTCGGGAGGCTGAGACAGGAGAATCACTTGAACCCAG

GAGGCAGAGGTTGCAGGGAGCCGAGATCGTGTACTGCACTCC

AGCCTGGGCAACAAGAGCGAAACTCCGTCTCAAAAAACAAAT

AAATAAATAAATAAATAAACAGACAAAATTCACTTTTTATTC

TATTAAACTTAACATACATGCTAA.

sFLT1 protein levels can be measured by measuring the amount of free, bound (i.e., bound to growth factor), or total sFLT1 (bound+free). VEGF or P1GF levels are determined by measuring the amount of free P1GF or free VEGF (i.e., not bound to sFLT1). One exemplary metric is [sFLT1/(VEGF+P1GF)], also referred to as the PE anti-angiogenic index (PAAI).

By "pre-eclampsia anti-angiogenesis index (PAAI)" is meant the ratio of sFLT1/VEGF+P1GF used as an indicator of anti-angiogenic activity. A PAAI greater than 20 is considered to be indicative of PE or risk of PE.

By "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (Biol. Reproduction, 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g. VEGF-A, VEGF-B, VEGF-C, VEGF-D, VEGF-E, VEGF189, VEGF165, or VEGF 121). In certain embodiments, VEGF is the VEGF121 or VEGF 165 isoform (Tischer et al., J. Biol. Chem. 266, 11947-11954, 1991; Neufed et al. Cancer Metastasis 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (J. Biol. Chem. 276:3222-3230, 2001). VEGF includes human forms and can include other animal forms of VEGF (e.g. mouse, rat, dog, chicken or the like).

By "placental growth factor (P1GF)" is meant a mammalian growth factor that is homologous to the protein defined by GenBank accession number P49763 and that has P1GF biological activity. P1GF is a glycosylated homodimer belonging to the VEGF family and can be found in two distinct isoforms through alternative splicing mechanisms. P1GF is expressed by cyto- and syncytiotrophoblasts in the placenta and P1GF biological activities include induction of proliferation, migration, and activation of endothelial cells, particularly trophoblast cells.

By "trophoblast" is meant the mesectodermal cell layer covering the blastocyst that erodes the uterine mucosa and through which the embryo receives nourishment from the mother. Trophoblast cells contribute to the formation of the placenta.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein (e.g., causes production of one or more sFLT1 proteins) or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target (sFLT1) and non-target (flFLT1) genes) can differ by one or more nucleotides, e.g., at an intronic region. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is a allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-µ, wherein T is an mRNA targeting moiety, L is a linking moiety, and µ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portions of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

In some embodiments, the RNA silencing agents of the invention are designed to target intronic regions in mRNA molecules encoding one or more sFLT1 proteins.

The present invention targets one or more sFLT1 mRNAs and their corresponding proteins. One strand of double-stranded RNA (siRNA) complements a target sequence within the sFLT1 mRNA. After introduction of siRNA into a subject or cell, the siRNA partially unwinds, binds to an intronic target region within the sFLT1 mRNA in a site-specific manner, and activates an mRNA nuclease. This nuclease cleaves the sFLT1 mRNA, thereby halting translation of the sFLT1 protein. Cells rid themselves of partially digested mRNA, thus precluding translation, or cells digest partially translated proteins. In certain embodiments, sFLT1 protein expression is reduced in a subject or cell by about 30% to 50%, or by about 30% to 40%.

In embodiments of the invention, RNA silencing agents of the invention are capable of targeting the human flt1 gene can be found at positions 2283 (5' CTCTCGGATCTC-CAAATTTA 3' (SEQ ID NO:1)) or 2519 (5' CATCATAGC-TACCATTTATT 3' (SEQ ID NO:2)).

Various aspects of the invention are described in further detail in the following subsections.

I. siRNA Design

In some embodiments, siRNAs are designed as follows. First, a portion of the target gene (e.g., the flt1 gene), e.g., one or more of the target sequences, is selected, e.g., one or any combination of sFLT1-i13-2283, sFLT1-i15a-2519, sFLT1-i13-2318, sFLT1-i15a-2585 from an intronic region of a target gene. Cleavage of mRNA at these sites should eliminate translation of corresponding soluble protein. Sense strands were designed based on the target sequence. Preferably, the portion (and corresponding sense strand) includes about 30 to 35 nucleotides, e.g., 30, 31, 32, 33, 34 or 35 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably, the RNAi agents of the invention do not elicit a PKR response (i.e., are of a sufficiently short length). However, longer RNAi agents may be useful, for example, in cell types incapable of generating a PRK response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2- or 3-nucleotide overhangs are generated, i.e., the 3' end of the sense strand extends 1, 2 or 3 nucleotides further than the 5' end of the antisense strand and/or the 3' end of the antisense strand extends 1, 2 or 3 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the sFLT1 target sequences is described in detail below. siRNAs can be designed according to the above exemplary teachings for any other target sequences found in the flt1 gene. Moreover, the technology is applicable to targeting any other target sequences, e.g., non-disease causing target sequences.

To validate the effectiveness by which siRNAs destroy mRNAs (e.g., sFLT1 mRNA), the siRNA can be incubated with cDNA (e.g., Flt1 cDNA) in a *Drosophila*-based in vitro mRNA expression system. Radiolabeled with $^{32}$P, newly synthesized mRNAs (e.g., Flt1 mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

II. RNAi Agents

The present invention includes siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (i.e., flt1 genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs, such as multiple regions of the gene encoding sFlt1, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fatal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

III. Anti-sFlt1 RNA Silencing Agents

The present invention features anti-sFlt1 RNA silencing agents (e.g., siRNA and shRNAs), methods of making said RNA silencing agents, and methods (e.g., research and/or therapeutic methods) for using said improved RNA silencing agents (or portions thereof) for RNA silencing of one or more sFLT1 proteins. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

a) Design of Anti-sFlt1 siRNA Molecules

An siRNA molecule of the invention is a duplex consisting of a sense strand and complementary antisense strand, the antisense strand having sufficient complementary to an sFLT1 mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence, e.g., a target sequence. In one embodiment, a target sequence is found in a soluble Flt1 mRNA, but not in the full-length Flt mRNA. In another embodiment, a target sequence is found in both a soluble Flt1 mRNA and the full-length Flt mRNA. In another embodiment, a target sequence is found in the full-length Flt mRNA. The first strand should be complementary to the target sequence, and the other strand is substantially complementary to the first strand. In one embodiment, the target sequence is encoded in an intronic region of one or more soluble Flt mRNA sequences. Exemplary target sequences correspond to one or more intronic regions of a target gene. Cleavage of mRNA at these sites should eliminate translation of corresponding soluble protein but not of the full-length protein. Target sequences from other regions of the flt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. In some embodiments, the sense strand includes 16 nucleotides. In some embodiments, the sense strand includes 17 nucleotides. In some embodiments, the sense strand includes 18 nucleotides. In some embodiments, the sense strand includes 19 nucleotides. In some embodiments, the sense strand includes 20 nucleotides. In some embodiments, the sense strand includes 21 nucleotides. In some embodiments, the sense strand includes 22 nucleotides. In some embodiments, the sense strand includes 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a soluble flt1 and a full-length flt1 allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In some embodiments, the antisense or guide strand is longer than the sense strand. In some embodiments, the antisense or guide strand is shorter than the sense strand. In some embodiments, the antisense or guide strand includes about 19 to 25 nucleotides, e.g., 19, 20, 21, 22, 23, 24 or 25 nucleotides. In some embodiments, the antisense or guide strand includes 21, 22 or 23 nucleotides. In some embodiments, the antisense or guide strand includes 16 nucleotides. In some embodiments, the antisense or guide strand includes 17 nucleotides. In some embodiments, the antisense or guide strand includes 18 nucleotides. In some embodiments, the antisense or guide strand includes 19 nucleotides. In some embodiments, the antisense or guide strand includes 20 nucleotides. In some embodiments, the antisense or guide strand includes 21 nucleotides. In some embodiments, the antisense or guide strand includes 22 nucleotides. In some embodiments, the antisense or guide strand includes 23 nucleotides.

In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. In some embodiments, the 3' overhang is 1 nucleotide. In some embodiments, the 3' overhang is 2 nucleotides. In some embodiments, the 3' overhang is 3 nucleotides. In some embodiments, the 3' overhang is 4 nucleotides. In some embodiments, the 3' overhang is 5 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., sFLT1 mRNA corresponding to soluble FLT1), the siRNA may be incubated with target cDNA (e.g., flt1 cDNA) in a *Drosophila*-based in vitro mRNA expression system. Radiolabeled with $^{32}P$, newly synthesized target mRNAs (e.g., sFlt1 mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-sflt1 siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

Sites of siRNA-mRNA complementation are selected which result in optimal mRNA specificity and maximal mRNA cleavage.

b) siRNA-Like Molecules siRNA-like molecules of the invention have a sequence (i.e., have a strand having a sequence) that is "sufficiently complementary" to a target sequence of a sflt1 mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5 or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5 or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an sFlt1 target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or antisense) to the sFlt1 target sequence. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., sFlt1 mRNA), for example, from a region 100 to 200 or 300 nucleotides upstream or downstream of the start of translation. In general, the sequence can be selected from any portion of the target RNA (e.g., mRNA) including an intronic region, the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, miR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-µ, wherein T is an mRNA targeting moiety, L is a linking moiety, and µ is an miRNA recruiting moiety. Any one or more moiety may be double stranded. Preferably, however, each moiety is single stranded.

Moieties within the tethers can be arranged or linked (in the 5' to 3' direction) as depicted in the formula T-L-µ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the invention, the miRNA may be any miRNA capable of repressing the target mRNA (e.g., one or more sflt1 mRNAs). Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., sflt1 gene expression) can be modulated using oligonucleotide-based compounds comprising two or more single stranded antisense oligonucleotides that are linked through their 5'-ends that allow the presence of two or more accessible 3'-ends to effectively inhibit or decrease sflt1 gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

IV. Modified Anti-sFlt1 RNA Silencing Agents

In certain aspects of the invention, an RNA silencing agent (or any portion thereof) of the invention as described supra may be modified such that the activity of the agent is further improved. For example, the RNA silencing agents described in herein may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

In certain embodiments, siRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications) or a 2'-methoxy-rich pattern (over 50% 2'-methoxy in the antisense strand and over 65% 2'-methoxy in the sense strand); and (5) single-stranded, fully phosphorothioated tails of 5-8 bases. The number of phosphorothioate modifications is varied from 6 to 17 total in different embodiments.

Certain compounds of the invention having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

The compounds of the invention can be described in the following aspects and embodiments.

In a first aspect, provided herein is a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 20 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises at least 65% 2'-O-methyl modifications; (9) the nucleotides at any one or more of positions 4, 6, 8, 10, and 14 from the 5' end of the sense strand are not 2'-methoxy-ribonucleotides; and (10) the nucleotides at positions 1-2 from the 5' end of the sense strand are connected to each other via phosphorothioate internucleotide linkages.

In an embodiment of the first aspect of the disclosure, the nucleotides at positions 2, 4, 5, 6, 8, 10, 12, 14, 16, and 20 from the 5' end of the antisense strand are not 2'-methoxy-ribonucleotides and the nucleotides at positions 4, 6, 8, 10, and 14 from the 5' end of the sense strand are not 2'-methoxy-ribonucleotides.

In an embodiment of the first aspect of the disclosure, the antisense strand is 21 nucleotides in length and the sense strand is 16 nucleotides in length.

In an embodiment of the first aspect of the disclosure, the antisense strand comprises the nucleic acid sequence of 5'

UAAAUUUGGAGAUCCGAGAGA 3' (SEQ ID NO: 8) and the sense strand comprises the nucleic acid sequence of 5' CGGAUCUCCAAAUUUA 3' (SEQ ID NO: 9).

In an embodiment of the first aspect of the disclosure, the antisense strand comprises the nucleic acid sequence of 5' UAUAAAUGGUAGCUAUGAUGA 3' (SEQ ID NO: 10) and the sense strand comprises the nucleic acid sequence of 5' AUAGCUACCAUUUAUA 3' (SEQ ID NO: 11).

In an embodiment of the first aspect of the disclosure, the antisense strand comprises a 5' vinyl phosphonate.

In a second aspect, provided herein is a double stranded RNA (dsRNA), said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In an embodiment of the second aspect of the disclosure, the antisense strand is 21 nucleotides in length and the sense strand is 16 nucleotides in length.

In an embodiment of the second aspect of the disclosure, the antisense strand comprises the nucleic acid sequence of 5' UAAAUUUGGAGAUCCGAGAGA 3' (SEQ ID NO: 8) and the sense strand comprises the nucleic acid sequence of 5' CGGAUCUCCAAAUUUA 3' (SEQ ID NO: 9).

In an embodiment of the second aspect of the disclosure, the antisense strand comprises the nucleic acid sequence of 5' UAUAAAUGGUAGCUAUGAUGA 3' (SEQ ID NO: 10) and the sense strand comprises the nucleic acid sequence of 5' AUAGCUACCAUUUAUA 3' (SEQ ID NO: 11).

In an embodiment of the second aspect of the disclosure, the antisense strand comprises a 5' vinyl phosphonate.

In a third aspect, provided herein is a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 50% 2'-O-methyl modifications; (4) the nucleotides at any one or more of positions 2, 4, 5, 6, 8, 10, 12, 14, 16, and 18 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises at least 80% 2'-O-methyl modifications; (9) the nucleotides at any one or more of positions 7, 9, and 11 from the 5' end of the sense strand are not 2'-methoxy-ribonucleotides; and (10) the nucleotides at positions 1-2 from the 5' end of the sense strand are connected to each other via phosphorothioate internucleotide linkages.

In an embodiment of the third aspect of the disclosure, the nucleotides at positions 2, 4, 5, 6, 8, 10, 12, 14, 16, and 18 from the 5' end of the antisense strand are not 2'-methoxy-ribonucleotides and the nucleotides at positions 7, 9, and 11 from the 5' end of the sense strand are not 2'-methoxy-ribonucleotides.

In an embodiment of the third aspect of the disclosure, the antisense strand is 21 nucleotides in length and the sense strand is 16 nucleotides in length.

In an embodiment of the third aspect of the disclosure, the antisense strand comprises the nucleic acid sequence of 5' UAAAUUUGGAGAUCCGAGAGA 3' (SEQ ID NO: 8) and the sense strand comprises the nucleic acid sequence of 5' CGGAUCUCCAAAUUUA 3' (SEQ ID NO: 9).

In an embodiment of the third aspect of the disclosure, the antisense strand comprises the nucleic acid sequence of 5' UAUAAAUGGUAGCUAUGAUGA 3' (SEQ ID NO: 10) and the sense strand comprises the nucleic acid sequence of 5' AUAGCUACCAUUUAUA 3' (SEQ ID NO: 11).

In an embodiment of the third aspect of the disclosure, the antisense strand comprises a 5' vinyl phosphonate.

In a fourth aspect, provided herein is a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 70% 2'-O-methyl modifications; (4) the nucleotides at any one or more of positions 2, 4, 5, 6, 8, and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In an embodiment of the fourth aspect of the disclosure, the nucleotides at positions 2, 4, 5, 6, 8, and 14 from the 5' end of the antisense strand are not 2'-methoxy-ribonucleotides.

In an embodiment of the fourth aspect of the disclosure, the antisense strand is 21 nucleotides in length and the sense strand is 16 nucleotides in length.

In an embodiment of the fourth aspect of the disclosure, the antisense strand comprises the nucleic acid sequence of 5' UAAAUUUGGAGAUCCGAGAGA 3' (SEQ ID NO: 8) and the sense strand comprises the nucleic acid sequence of 5' CGGAUCUCCAAAUUUA 3' (SEQ ID NO: 9).

In an embodiment of the fourth aspect of the disclosure, the antisense strand comprises the nucleic acid sequence of 5' UAUAAAUGGUAGCUAUGAUGA 3' (SEQ ID NO: 10) and the sense strand comprises the nucleic acid sequence of 5' AUAGCUACCAUUUAUA 3' (SEQ ID NO: 11).

In an embodiment of the fourth aspect of the disclosure, the antisense strand comprises a 5' vinyl phosphonate.

In a five aspect, provided herein is a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 75% 2'-O-methyl modifications; (4) the nucleotides at any one or more of positions 2, 4, 5, 6, and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In an embodiment of the fifth aspect of the disclosure, the nucleotides at positions 2, 4, 5, 6, and 14 from the 5' end of the antisense strand are not 2'-methoxy-ribonucleotides.

In an embodiment of the fifth aspect of the disclosure, the antisense strand is 21 nucleotides in length and the sense strand is 16 nucleotides in length.

In an embodiment of the fifth aspect of the disclosure, the antisense strand comprises the nucleic acid sequence of 5' UAAAUUUGGAGAUCCGAGAGA 3' (SEQ ID NO: 8) and the sense strand comprises the nucleic acid sequence of 5' CGGAUCUCCAAAUUUA 3' (SEQ ID NO: 9).

In an embodiment of the fifth aspect of the disclosure, the antisense strand comprises the nucleic acid sequence of 5' UAUAAAUGGUAGCUAUGAUGA 3' (SEQ ID NO: 10) and the sense strand comprises the nucleic acid sequence of 5' AUAGCUACCAUUUAUA 3' (SEQ ID NO: 11).

In an embodiment of the fifth aspect of the disclosure, the antisense strand comprises a 5' vinyl phosphonate.

In a sixth aspect, provided herein is a double stranded RNA (dsRNA) molecule, said dsRNA comprising an antisense strand and a sense strand, each strand with a 5' end and a 3' end, wherein: (1) the antisense strand comprises a sequence substantially complementary to a nucleic acid sequence of 5' CTCTCGGATCTCCAAATTTA 3' (SEQ ID NO:1) or 5' CATCATAGCTACCATTTATT 3' (SEQ ID NO:2); (2) the antisense strand is at least 20 nucleotides in length; (3) the antisense strand comprises at least 85% 2'-O-methyl modifications; (4) the nucleotides at any one or more of positions 2 and 14 from the 5' end of the antisense strand are not 2'-methoxy-ribonucleotides; (5) the nucleotides at positions 1-2 to 1-8 from the 3' end of the antisense strand are connected to each other via phosphorothioate internucleotide linkages; (6) a portion of the antisense strand is complementary to a portion of the sense strand; (7) the sense strand is at least 15 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In an embodiment of the sixth aspect of the disclosure, the nucleotides at positions 2 and 14 from the 5' end of the antisense strand are not 2'-methoxy-ribonucleotides.

In an embodiment of the sixth aspect of the disclosure, the antisense strand is 21 nucleotides in length and the sense strand is 16 nucleotides in length.

In an embodiment of the sixth aspect of the disclosure, the antisense strand comprises the nucleic acid sequence of 5' UAAAUUUGGAGAUCCGAGAGA 3' (SEQ ID NO: 8) and the sense strand comprises the nucleic acid sequence of 5' CGGAUCUCCAAAUUUA 3' (SEQ ID NO: 9).

In an embodiment of the sixth aspect of the disclosure, the antisense strand comprises the nucleic acid sequence of 5' UAUAAAUGGUAGCUAUGAUGA 3' (SEQ ID NO: 10) and the sense strand comprises the nucleic acid sequence of 5' AUAGCUACCAUUUAUA 3' (SEQ ID NO: 11).

In an embodiment of the sixth aspect of the disclosure, the antisense strand comprises a 5' vinyl phosphonate.

In an embodiment of any of the first to sixth aspect of the disclosure, the 3' end of the sense strand is linked to PC-DCA (phosphocholine-docosanoic acid) via a C7 amino linker and a dTdT cleavable linker.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In some embodiments, the sense strand is modified by the substitution of at least 50% of the internal nucleotides. In some embodiments, the sense strand is modified by the substitution of at least 55% of the internal nucleotides. In some embodiments, the sense strand is modified by the substitution of at least 60% of the internal nucleotides. In some embodiments, the sense strand is modified by the substitution of at least 65% of the internal nucleotides. In some embodiments, the sense strand is modified by the substitution of at least 70% of the internal nucleotides. In some embodiments, the sense strand is modified by the substitution of at least 75% of the internal nucleotides. In some embodiments, the sense strand is modified by the substitution of at least 80% of the internal nucleotides. In some embodiments, the sense strand is modified by the substitution of at least 85% of the internal nucleotides. In some embodiments, the sense strand is modified by the substitution of at least 90% of the internal nucleotides. In some embodiments, the sense strand is modified by the substitution of at least 95% of the internal nucleotides. In some embodiments, the sense strand is modified by the substitution of at least 96% of the internal nucleotides. In some embodiments, the sense strand is modified by the substitution of at least 97% of the internal nucleotides. In some embodiments, the sense strand is modified by the substitution of at least 98% of the internal nucleotides. In some embodiments, the sense strand is modified by the substitution of at least 99% of the internal nucleotides. In some embodiments, the sense strand is modified by the substitution of 100% of the internal nucleotides.

In some embodiments, the antisense strand is modified by the substitution of at least 50% of the internal nucleotides. In some embodiments, the antisense strand is modified by the substitution of at least 55% of the internal nucleotides. In some embodiments, the antisense strand is modified by the substitution of at least 60% of the internal nucleotides. In some embodiments, the antisense strand is modified by the substitution of at least 65% of the internal nucleotides. In some embodiments, the antisense strand is modified by the substitution of at least 70% of the internal nucleotides. In some embodiments, the antisense strand is modified by the substitution of at least 75% of the internal nucleotides. In some embodiments, the antisense strand is modified by the substitution of at least 80% of the internal nucleotides. In some embodiments, the antisense strand is modified by the substitution of at least 85% of the internal nucleotides. In some embodiments, the antisense strand is modified by the substitution of at least 90% of the internal nucleotides. In some embodiments, the antisense strand is modified by the substitution of at least 95% of the internal nucleotides. In some embodiments, the antisense strand is modified by the substitution of at least 96% of the internal nucleotides. In some embodiments, the antisense strand is modified by the substitution of at least 97% of the internal nucleotides. In some embodiments, the antisense strand is modified by the substitution of at least 98% of the internal nucleotides. In some embodiments, the antisense strand is modified by the substitution of at least 99% of the internal nucleotides.

In some embodiments, the antisense strand is modified by the substitution of 100% of the internal nucleotides.

In a preferred embodiment of the present invention, the RNA silencing agents may contain at least one modified nucleotide analogue. The one or more nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH- group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, and/or a 2' F moiety on a U in a sense or antisense strand, but especially on a sense strand, and/or a 2' OMe moiety in a 3' overhang, e.g., at the 3' terminus (3' terminus means at the 3' atom of the molecule or at the most 3' moiety, e.g., the most 3' P or 2' position, as indicated by the context) and/or a 2' F moiety; (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Heavily Modified RNA Silencing Agents

In certain embodiments, the RNA silencing agent comprises at least 80% chemically modified nucleotides. In certain embodiments, the RNA silencing agent is fully chemically modified, i.e., 100% of the nucleotides are chemically modified.

In certain embodiments, the RNA silencing agent is 2'-O-methyl rich, i.e., comprises greater than 50% 2'-O-methyl content. In certain embodiments, the RNA silencing agent comprises at least about 55%, 60%, 65%, 70%, 75%, 80%, 85%, 90%, 95%, or 100% 2'-O-methyl nucleotide content. In certain embodiments, the RNA silencing agent comprises at least about 70% 2'-O-methyl nucleotide modifications. In certain embodiments, the RNA silencing agent comprises between about 70% and about 90% 2'-O-methyl nucleotide modifications.

In certain embodiments, the RNA silencing agent is a dsRNA comprising an antisense strand and sense strand. In some embodiments, the antisense strand comprises at least about 50% 2'-O-methyl nucleotide modifications. In some embodiments, the antisense strand comprises greater than about 50% 2'-O-methyl nucleotide modifications (e.g., 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% 2'-O-methyl nucleotide modifications). In some embodiments, the antisense strand comprises greater than 50% 2'-O-methyl nucleotide modifications. In some embodiments, the antisense strand comprises greater than 60% 2'-O-methyl nucleotide modifications. In some embodiments, the antisense strand comprises about 50% 2'-O-methyl nucleotide modifications. In some embodiments, the antisense strand comprises about 55% 2'-O-methyl nucleotide modifications. In some embodiments, the antisense strand comprises about 60% 2'-O-methyl nucleotide modifications. In some embodiments, the antisense strand comprises about 65% 2'-O-methyl nucleotide modifications. In some embodiments, the antisense strand comprises about 70% 2'-O-methyl nucleotide modifications. In some embodiments, the antisense strand comprises about 75% 2'-O-methyl nucleotide modifications. In some embodiments, the antisense strand comprises about 80% 2'-O-methyl nucleotide modifications. In some embodiments, the antisense strand comprises about 85% 2'-O-methyl nucleotide modifications. In some embodiments, the antisense strand comprises about 90% 2'-O-methyl nucleotide modifications. In some embodiments, the antisense strand comprises about 95% 2'-O-methyl nucleotide modifications. In some embodiments, the antisense strand comprises about 99% 2'-O-methyl nucleotide modifications. In some embodiments, the antisense strand comprises about 100% 2'-O-methyl nucleotide modifications. In certain embodiments, the antisense strand comprises at least about 70% 2'-O-methyl nucleotide modifications. In certain embodiments, the antisense strand comprises between about 70% and about 90% 2'-O-methyl nucleotide modifications. In some embodiments, the antisense strand comprises about 70% to about 90% 2'-O-methyl nucleotide modifications. In some embodiments, the antisense strand comprises about 50% to about 100% 2'-O-methyl nucleotide modifications. In some embodiments, the antisense strand comprises about 50% to about 90% 2'-O-methyl nucleotide modifications. In some embodiments, the antisense strand comprises about 50% to about 80% 2'-O-methyl nucleotide modifications. In some embodiments, the antisense strand comprises about 50% to about 75% 2'-O-methyl nucleotide modifications. In some embodiments, the antisense strand comprises about 50% to about 70% 2'-O-methyl nucleotide modifications. In some embodiments, the antisense strand comprises about 50% to about 65% 2'-O-methyl nucleotide modifications. In some embodiments, the antisense strand comprises about 50% to about 60% 2'-O-methyl nucleotide modifications. In some embodiments, the antisense strand comprises about 50% to about 55% 2'-O-methyl nucleotide modifications.

In some embodiments, the sense strand comprises at least about 60% 2'-O-methyl nucleotide modifications. In some embodiments, the sense strand comprises greater than 60% 2'-O-methyl nucleotide modifications. In certain embodiments, the sense strand comprises at least about 70% 2'-O-methyl nucleotide modifications. In some embodiments, the sense strand comprises 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% 2'-O-methyl nucleotide modifications. In some embodiments, the sense strand comprises about 60% 2'-O-methyl nucleotide modifications. In some embodiments, the sense strand comprises about 65% 2'-O-methyl nucleotide modifications. In some embodiments, the sense strand comprises about 70% 2'-O-methyl nucleotide modifications. In some embodiments, the sense strand comprises about 75% 2'-O-methyl nucleotide modifications. In some embodiments, the sense strand comprises about 80% 2'-O-methyl nucleotide modifications. In some embodiments, the sense strand comprises about 85% 2'-O-methyl nucleotide modifications. In some embodiments, the sense strand comprises about 90% 2'-O-methyl nucleotide modifications. In some embodiments, the sense strand comprises about 99% 2'-O-methyl nucleotide modifications. In some embodiments, the sense strand comprises about 100% 2'-O-methyl nucleotide modifications. In certain embodiments, the sense strand comprises between about 70% and about 90% 2'-O-methyl nucleotide modifications. In certain embodiments, the sense strand comprises between 100% 2'-O-methyl nucleotide modifications. In some embodiments, the sense strand comprises about 70% to about 90% 2'-O-methyl nucleotide modifications. In some embodiments, the sense strand comprises about 60% to about 100% 2'-O-methyl nucleotide modifications. In some embodiments, the sense strand comprises about 60% to about 95% 2'-O-methyl nucleotide modifications. In some embodiments, the sense strand comprises about 60% to about 90% 2'-O-methyl nucleotide modifications. In some embodiments, the sense strand comprises about 60% to about 85% 2'-O-methyl nucleotide modifications. In some embodiments, the sense strand comprises about 60% to about 80% 2'-O-methyl nucleotide modifications. In some embodiments, the sense strand comprises about 60% to about 75% 2'-O-methyl nucleotide modifications. In some embodiments, the sense strand comprises about 60% to about 70% 2'-O-methyl nucleotide modifications. In some embodiments, the sense strand comprises about 65% to about 90% 2'-O-methyl nucleotide modifications. In some embodiments, the sense strand comprises about 65% to about 85% 2'-O-methyl nucleotide modifications. In some embodiments, the sense strand comprises about 65% to about 80% 2'-O-methyl nucleotide modifications. In some embodiments, the sense strand comprises about 65% to about 75% 2'-O-methyl nucleotide modifications. In some embodiments, the sense strand comprises about 65% to about 70% 2'-O-methyl nucleotide modifications.

2'-O-methyl rich RNA silencing agents and specific chemical modification patterns are further described in U.S. Pat. No. 11,279,930B2 and US2021/0115442A1, each of which is incorporated herein by reference.

Internucleotide Linkage Modifications

In certain embodiments, at least one internucleotide linkage, intersubunit linkage, or nucleotide backbone is modified in the RNA silencing agent. In certain embodiments, all of the internucleotide linkages in the RNA silencing agent are modified. In certain embodiments, the modified internucleotide linkage comprises a phosphorothioate internucleotide linkage. In certain embodiments, the RNA silencing agent comprise 1, 2, 3, 4, 5, 6, 7, 8, 9, 10, 11, 12, 13, 14, 15, 16, 17, 18, 19, 20, 21, 22, 23, 24, or 25 phosphorothioate internucleotide linkages. In certain embodiments, the RNA silencing agent comprises 4-16 phosphorothioate internucleotide linkages. In certain embodiments, the RNA silencing agent comprises 8-13 phosphorothioate internucleotide linkages. In certain embodiments, the RNA silencing agent is a dsRNA comprising an antisense strand and a sense strand, each comprising a 5' end and a 3' end. In certain embodiments, the nucleotides at positions 1 and 2 from the 5' end of sense strand are connected to adjacent ribonucleotides via phosphorothioate internucleotide linkages. In certain embodiments, the nucleotides at positions 1 and 2 from the 3' end of sense strand are connected to adjacent ribonucleotides via phosphorothioate internucleotide linkages. In certain embodiments, the nucleotides at positions 1 and 2 from the 5' end of antisense strand are connected to adjacent ribonucleotides via phosphorothioate internucleotide linkages. In certain embodiments, the nucleotides at positions 1-2 to 1-8 from the 3' end of antisense strand are connected to adjacent ribonucleotides via phosphorothioate internucleotide linkages. In certain embodiments, the nucleotides at positions 1-2, 1-3, 1-4, 1-5, 1-6, 1-7, or 1-8 from the 3' end of antisense strand are connected to adjacent ribonucleotides via phosphorothioate internucleotide linkages. In certain embodiments, the nucleotides at positions 1-2 to 1-7 from the 3' end of antisense strand are connected to adjacent ribonucleotides via phosphorothioate internucleotide linkages.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., 0-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a placental cell, a kidney cell and/or a liver cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue. For example, the target tissue can be the placenta, the kidneys or the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the placenta, liver and/or kidney and therefore less likely to be cleared from the body. A lipid or lipid-based ligand that binds to HSA less strongly can be used to target the conjugate to the placenta, liver and/or kidney. Other moieties that target to placental, liver and/or kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45 or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties.

In certain embodiments, the functional moiety is linked to the 5' end and/or 3' end of the RNA silencing agent of the disclosure. In certain embodiments, the functional moiety is linked to the 5' end and/or 3' end of an antisense strand of the RNA silencing agent of the disclosure. In certain embodiments, the functional moiety is linked to the 5' end and/or 3' end of a sense strand of the RNA silencing agent of the disclosure. In certain embodiments, the functional moiety is linked to the 3' end of a sense strand of the RNA silencing agent of the disclosure.

In certain embodiments, the functional moiety is linked to the RNA silencing agent by a linker. In certain embodiments, the functional moiety is linked to the antisense strand and/or sense strand by a linker. In certain embodiments, the functional moiety is linked to the 3' end of a sense strand by a linker. In certain embodiments, the linker comprises a divalent or trivalent linker. In certain embodiments, the linker comprises an ethylene glycol chain, an alkyl chain, a peptide, RNA, DNA, a phosphodiester, a phosphorothioate, a phosphoramidate, an amide, a carbamate, or a combination thereof. In certain embodiments, the divalent or trivalent linker is selected from:

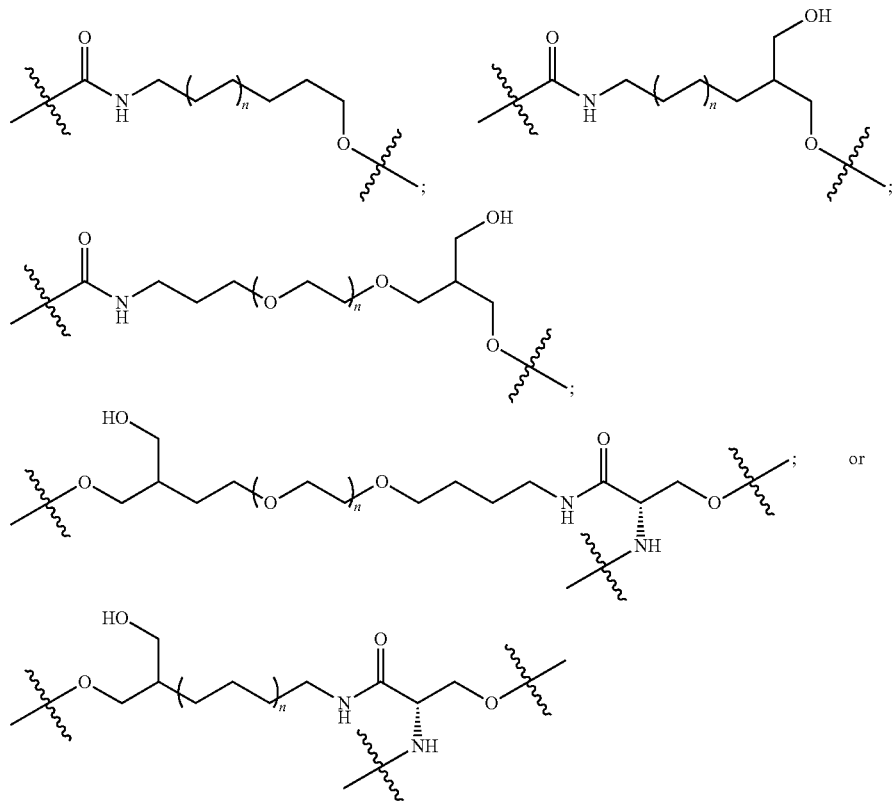

wherein n is 1, 2, 3, 4, or 5.

In certain embodiments, the linker further comprises a phosphodiester or phosphodiester derivative. In certain embodiments, the phosphodiester or phosphodiester derivative is selected from the group consisting of:

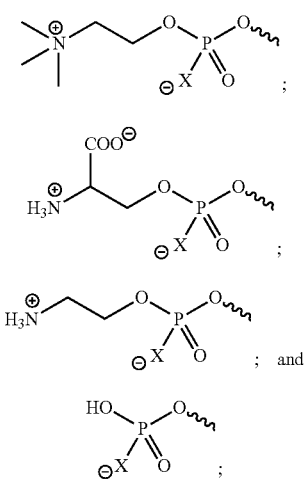

wherein X is O, S or $BH_3$.

The various functional moieties of the disclosure and means to conjugate them to RNA silencing agents are described in further detail in WO2017/030973A1 and WO2018/031933A2, incorporated herein by reference.

In certain embodiments, the linker is a cleavable linker.

In certain embodiments, the cleavable linker comprises a phosphodiester linkage, a disulfide linkage, an acid-labile linkage, or a photocleavable linkage.

In certain embodiments, the cleavable linker comprises a dTdT dinucleotide with phosphodiester internucleotide linkages.

In certain embodiments, the acid-labile linkage comprises a β-thiopropionate linkage or a carboxydimethylmaleic anhydride (CDM) linkage.

In certain embodiments, the functional moiety PC-DCA with a C7 amino linker is represented by:

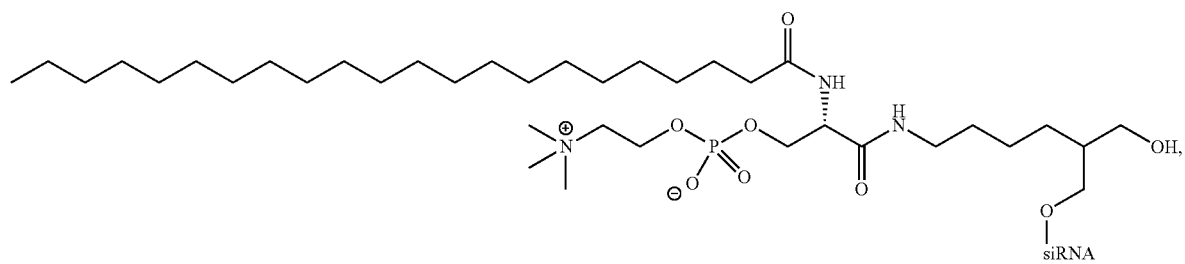

where "siRNA" corresponds to the 3' end of the sense strand.

V. Methods of Introducing Nucleic Acids, Vectors and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucuronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an flt1 intronic target sequence) is tested for its ability to specifically degrade mutant mRNA (e.g., sflt1 mRNA and/or the production of sFlt1 protein) in cells, in particular, in placental cells (e.g., labyrinth cells, trophoblasts (e.g., syncytiotrophoblasts and/or cytotrophoblasts), mesenchymal cells, mesenchymal-derived macrophages (Hofbauer cells), fibroblasts, fetal vascular cells (e.g., smooth muscle cells, perivascular cells (pericytes), and endothelial cells)), liver cells and/or kidney cells. Also suitable for cell-based validation assays are other readily transfectable cells, for example, trophoblast cells, HeLa cells or COS cells. Cells are transfected with human wild type or mutant cDNAs (e.g., human wild-type or secreted flt1 cDNA). Standard siRNA, modified siRNA or vectors able to produce siRNA from U-looped mRNA are co-transfected. Selective reduction in target mRNA (e.g., sflt1 mRNA) and/or target protein (e.g., sFlt1 protein) is measured. Reduction of target mRNA or protein can be compared to levels of target mRNA or protein in the absence of an RNAi agent or in the presence of an RNAi agent that does not target sFlt1 mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

VI. Methods of Treatment

The present invention provides for both prophylactic and therapeutic methods of treating a subject at risk of (or susceptible to) a disease or disorder caused, in whole or in part, by secreted Flt1 protein. In one embodiment, the disease or disorder is a liver disease or disorder. In another embodiment, the disease or disorder is a kidney disease or disorder. In one embodiment, the disease or disorder is a placental disease or disorder. In one embodiment, the disease or disorder is a pregnancy-related disease or disorder. In a preferred embodiment, the disease or disorder is a disorder associated with the expression of soluble Flt1 protein and in which amplified expression of the soluble Flt1 protein leads to clinical manifestations of PE, postpartum PE, eclampsia and/or HELLP. In some embodiments, the disease or disorder is PE. In some embodiments, the disease or disorder is postpartum PE. In some embodiments, the disease or disorder is eclampsia. In some embodiments, the disease or disorder is HELLP.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for one or more target sequences within the gene (e.g., SEQ ID NOs: 1 or 2 or any combinations thereof), such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the invention can be administered to any patient diagnosed as having or at risk for developing a pregnancy-, liver- and/or kidney-related disorder, such as PE and/or eclampsia. In one embodiment, the patient is diagnosed as having a PE and/or eclampsia, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as two or more symptoms of PE or one or more symptoms of eclampsia. In another embodiment, the patient has not reached an advanced stage of the disease.

Delivery of an RNA silencing agent directly to an organ (e.g., directly to the placenta, liver and/or kidneys) can be at a dosage that is effective to treat or prevent a liver-, kidney- or pregnancy-related disease or disorder, e.g., PE, postpartum PE, eclampsia and/or HELLP.

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary.

VI. Pharmaceutical Compositions and Methods of Administration

The invention pertains to uses of the above-described agents for prophylactic and/or therapeutic treatments as described Infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Pharmaceutical compositions comprising the RNAi agents (e.g., dsRNA) provided herein encompass any pharmaceutically acceptable salts, esters, or salts of such esters. Accordingly, for example, the disclosure is also drawn to pharmaceutically acceptable salts of RNAi agents, prodrugs, pharmaceutically acceptable salts of such prodrugs, and other bioequivalents. Suitable pharmaceutically acceptable salts include, but are not limited to, sodium and potassium salts. In some embodiments, the disclosure provides salts of the RNAi agents (e.g., dsRNA). In some embodiments, the disclosure provides salts of the dsRNA agents. In some embodiments, the disclosure provides salts of the siRNA agents. In some embodiments, the salt is a sodium salt. In some embodiments, the salt is a potassium salt. In some embodiments, the salt is a pharmaceutically acceptable salt. In some embodiments, the salt of the RNAi agent is a pharmaceutically acceptable salt. In some embodiments, the salt of the dsRNA agent is a pharmaceutically acceptable salt. In some embodiments, the salt of the siRNA agent is a pharmaceutically acceptable salt.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

The route of delivery can be dependent on the disorder of the patient. In certain exemplary embodiments, a subject diagnosed with PE, postpartum PE, eclampsia and/or HELLP can be administered an anti-sFlt1 RNA silencing agent of the invention by IV or SC administration. In addition to an RNA silencing agent of the invention, a patient can be administered a second therapy, e.g., a palliative therapy and/or disease-specific therapy. The secondary therapy can be, for example, symptomatic (e.g., for alleviating symptoms), protective (e.g., for slowing or halting disease progression), or restorative (e.g., for reversing the disease process). For the treatment of PE, postpartum PE, eclampsia and/or HELLP, for example, symptomatic therapies can further include the drugs Atenolol, Hydralazine, Labetalol, magnesium sulfate, Methyldopa, Nicardipine, Nifedipine, sodium nitroprusside and the like.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

The phrases "stereochemically isomeric forms", "stereoforms", "stereoisoforms", "stereoisomers", and the like, as used herein, refers to different compounds made up of the same atoms bonded by the same sequence of bonds but having different three-dimensional structures which are not interchangeable. In some embodiments of the disclosure, the pharmaceutical compositions comprising RNAi agents (e.g., dsRNA) can be or include pure preparations of individual stereochemically isomeric forms of the RNAi agents. In some embodiments, the pharmaceutical compositions can be or include mixtures of two or more stereochemically isomeric forms of the RNAi agents.

VII. Kits

In certain other aspects, the invention provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1. Background and Significance of Preeclampsia (PE)

Overwhelming evidence from epidemiological and experimental studies now indicates that PE is caused by elevated levels of "soluble decoy" proteins (soluble FLT1s (sFLT1s)) from the Flt1 gene (VEGFR1) in the mother's blood stream (Young, B. C., Levine, R. J. & Karumanchi, S. A. Pathogenesis of preeclampsia. *Annual review of pathology* 5, 173-192 (2010); Maynard, S. E. et al. Excess placental soluble fms-like tyrosine kinase 1 (sFlt1) may contribute to endothelial dysfunction, hypertension, and proteinuria in preeclampsia. *The Journal of clinical investigation* 111, 649-658 (2003); Levine, R. J. et al. Circulating angiogenic factors and the risk of preeclampsia. *The New England journal of medicine* 350, 672-683 (2004); Heydarian, M. et al. Novel splice variants of sFlt1 are upregulated in preeclampsia. *Placenta* 30, 250-255 (2009)). FLT1 is a receptor tyrosine kinase (RTK) predominantly expressed in the placenta. A general mechanism for RTK modulation is production of truncated, secreted forms of the receptor that act as dominant negative regulators of the overall signaling pathway. Ligand sequestration by such soluble decoys inhibits intracellular signaling by the full-length receptor, thereby desensitizing the system to ligand concentration (Vorlova, S. et al. Induction of antagonistic soluble decoy receptor tyrosine kinases by intronic polyA activation. *Molecular cell* 43, 927-939 (2011).). In the case of FLT1, the soluble decoys are expressed from truncated mRNAs generated by polyadenylation within two introns (i13 and i15) upstream of the exons encoding the fl-FLT1 transmembrane (TM) and kinase domains.

In mammals, FLT1 is predominantly expressed in the placenta, with human placental Flt1 mRNA levels being 10-100 times higher than those observed in other adult tissues (Cerdeira, A. S. & Karumanchi, S. A. Angiogenic factors in preeclampsia and related disorders. *Cold Spring Harbor perspectives in medicine* 2 (2012)). Whereas the full-length isoform predominates in all tissues in non-pregnant adult humans (Id.), placental expression is dominated by three truncated isoforms, sFlt1-i13 short, sFlt1-i13 long and sFlt1-i15a, all of which encode sFLT1 proteins. This same pattern of high Flt1 in placenta and low expression in other non-pregnant adult tissues is observed in rodents.

However, because rodents lack the intron 14 polyadenylation site, they only express a single soluble decoy form: sFlt1-i13. In PE, both full-length (fl-Flt1) and truncated Flt1 mRNAs accumulate to higher levels in the placenta than in normal pregnancies, with the truncated isoforms being even more pronounced. These changes at the mRNA level likely explain the significant rise in sFLT1 proteins in the maternal bloodstream during PE.

Applicability of siRNAs for Treatment of PE

Previous work demonstrated the applicability of siRNA-based therapeutics for the treatment of PE (U.S. Pat. No. 9,862,952, incorporated herein by reference).

Example 2. Optimization of siRNAs Targeting sFLT1

Optimization of the previously described siRNAs was performed to enhance silencing while promoting placental tissue accumulation, minimizing siRNA degradation, and reducing toxicity. Optimization was performed by introducing a 2'-OMe rich scaffold for enhanced stability and PC-DCA conjugated sense strand for enhanced placental delivery. The optimized siRNAs showed increased accumulation, efficacy and safety compared to previously developed chemistries.

2'OMe Content Optimization

Figure 1B:
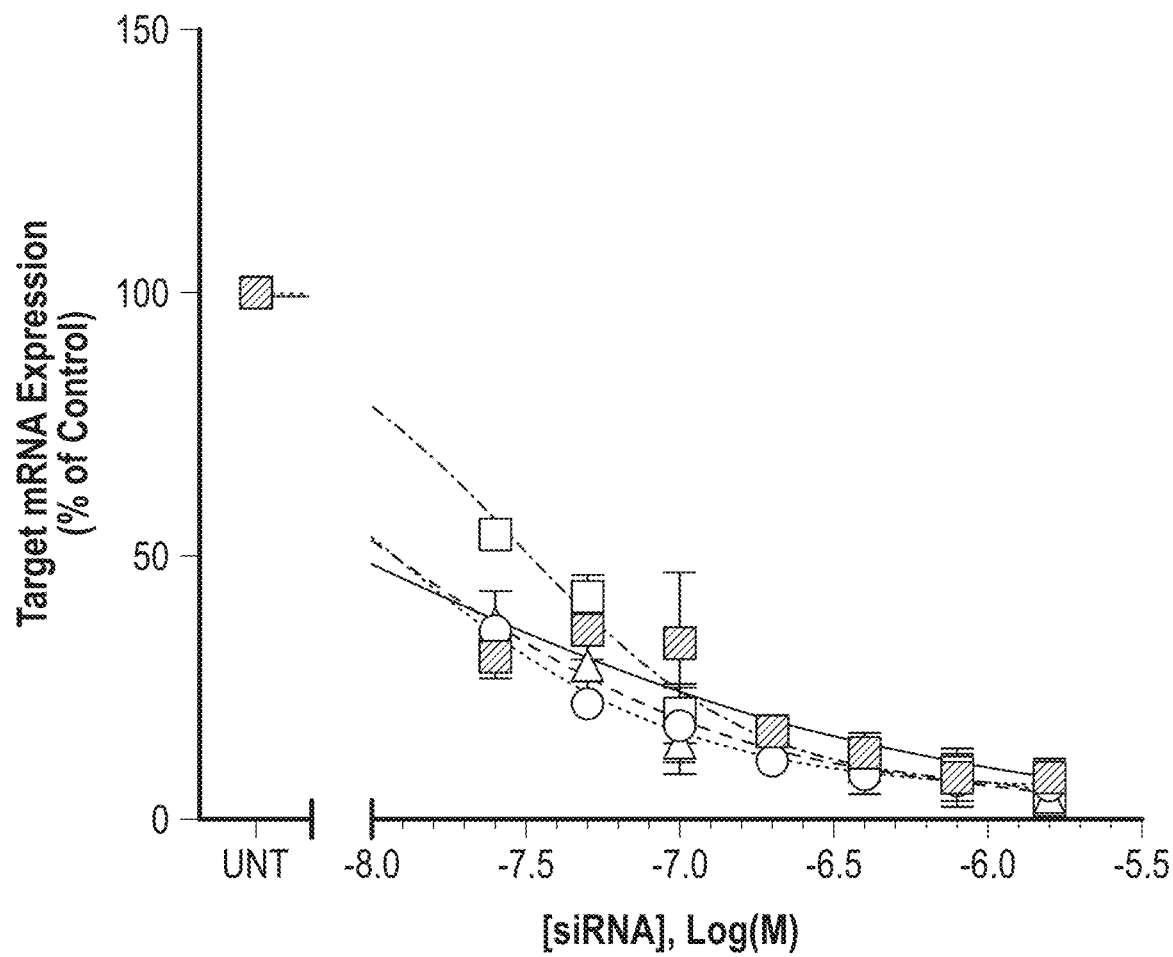

As shown in FIG. 1A, various amounts of 2'OMe modifications were employed in the antisense and sense strand of the siRNAs. As shown in FIG. 1B, Dose response results (n=3, mean±SD) of the siRNAs were produced targeting the sequence of the human flt1 gene at position 2283 (5' CTCTCGGATCTCCAAATTTA 3' (SEQ ID NO: 1). siRNAs targeting position 2519 (5' CATCATAGCTACCATTTATT 3' (SEQ ID NO: 2) were also tested with similar results. HeLa cells treated with siRNAs at concentrations shown for 72 hours. mRNA levels measured using the Dual-Glo® Luciferase Assay System and calculated as percentage of untreated control (C). Table of FIG. 1B—Max. KD (%)—maximum percent target mRNA knockdown with top treatment dose of siRNA, IC50—half maximal inhibitory concentration, AUC—area under the dose response curve, p-value—significance. The results demonstrate that increasing amounts of 2'OMe modifications in the siRNAs do not substantially reduce the silencing efficacy of said siRNAs. 2'OMe modifications are less toxic than 2'F modifications. Accordingly, the 2'OMe-rich siRNAs may be more suitable for therapeutic use.

Sense Strand Conjugate Optimization

Figure 2A:
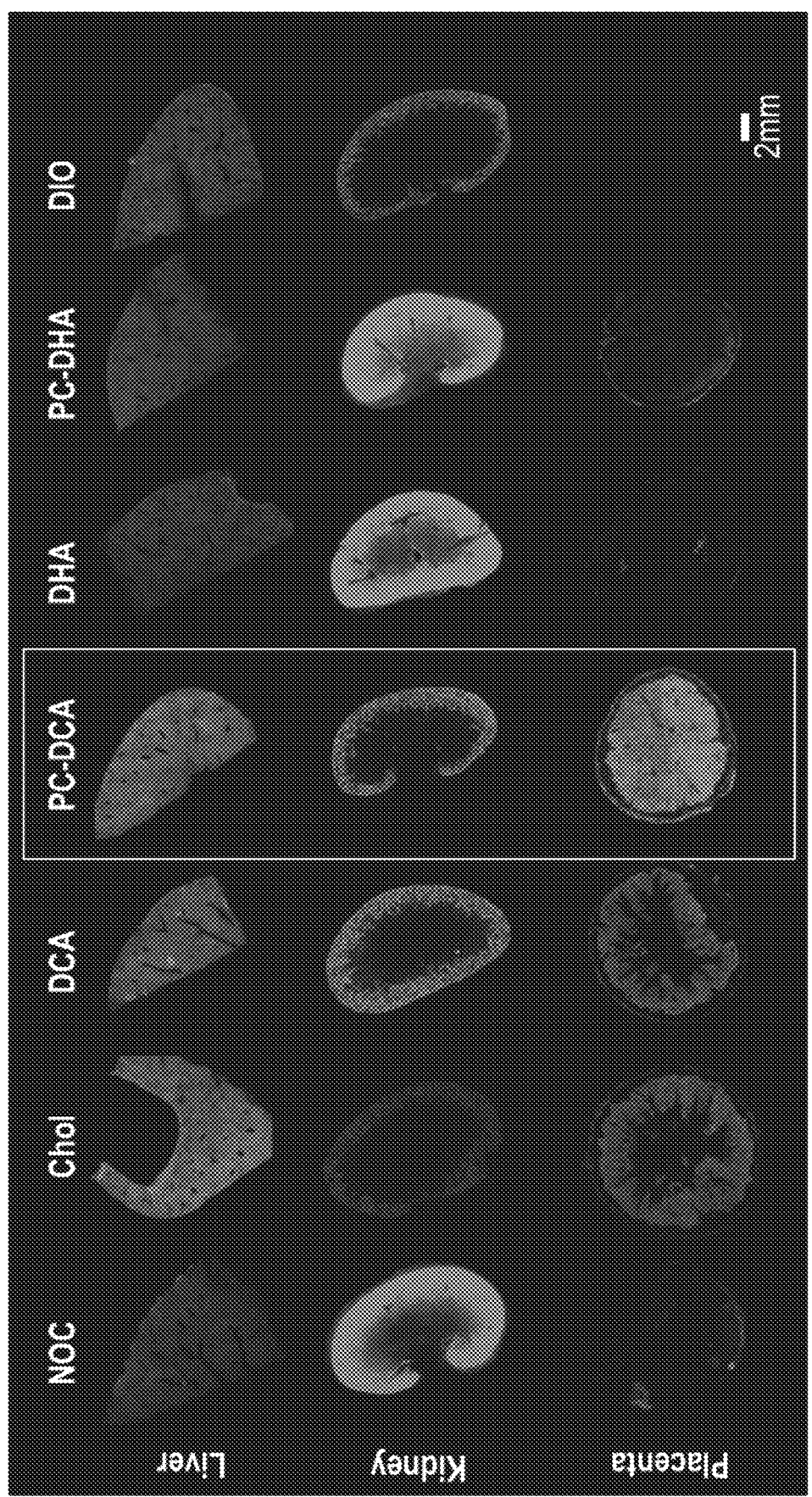
FIG. 2A-FIG. 2B depicts tissue fluorescent images and guide strand accumulation in said tissues.
Figure 2B:
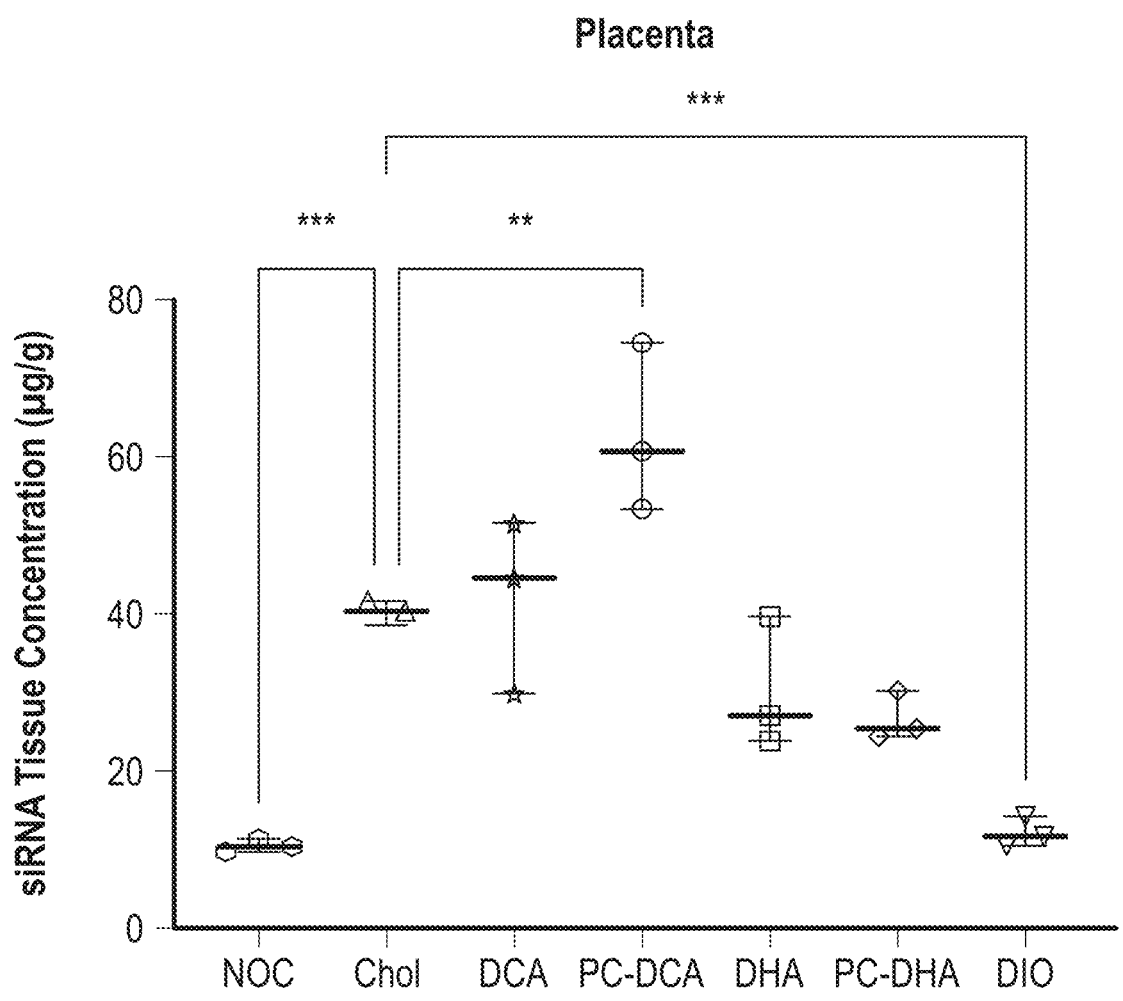

The siRNA conjugate plays an important role in directing the siRNA to the appropriate tissues and cells. As shown in FIG. 2A, Cy3-labelled siRNAs were conjugated with various functional moieties and liver, kidney, and placental tissue delivery was monitored by tissue fluorescent imaging. In this study, pregnant CD1 mice were injected with 20 mg/kg Cy3 labelled siRNA variants. Tissue Fluorescent imaging was performed with a Leica DMi8 inverted tilting microscope. 10× tiled array images. Scale bar=2 mm. All images acquired at identical laser intensity. As shown in FIG. 2B, guide strand accumulation was quantified after 48 hours by PNA hybridization assay (n=3). p-values describe statistically significant differences between each compound and the cholesterol-conjugated compound (One-way ANOVA;  p<0.01; * p<0.001; non-significant differences not marked). NOC—no conjugate, Chol—cholesterol, DCA—docosanoic acid, PC-DCA—phosphocholine-docosanoic acid, DHA—docosahexanoic acid, PC-DHA—phosphocholine-docosahexanoic acid, DIO—di-branched oligonucleotide. The results demonstrate that PC-DCA siRNA conjugates demonstrate enhanced placental accumulation.

Figure 3A:
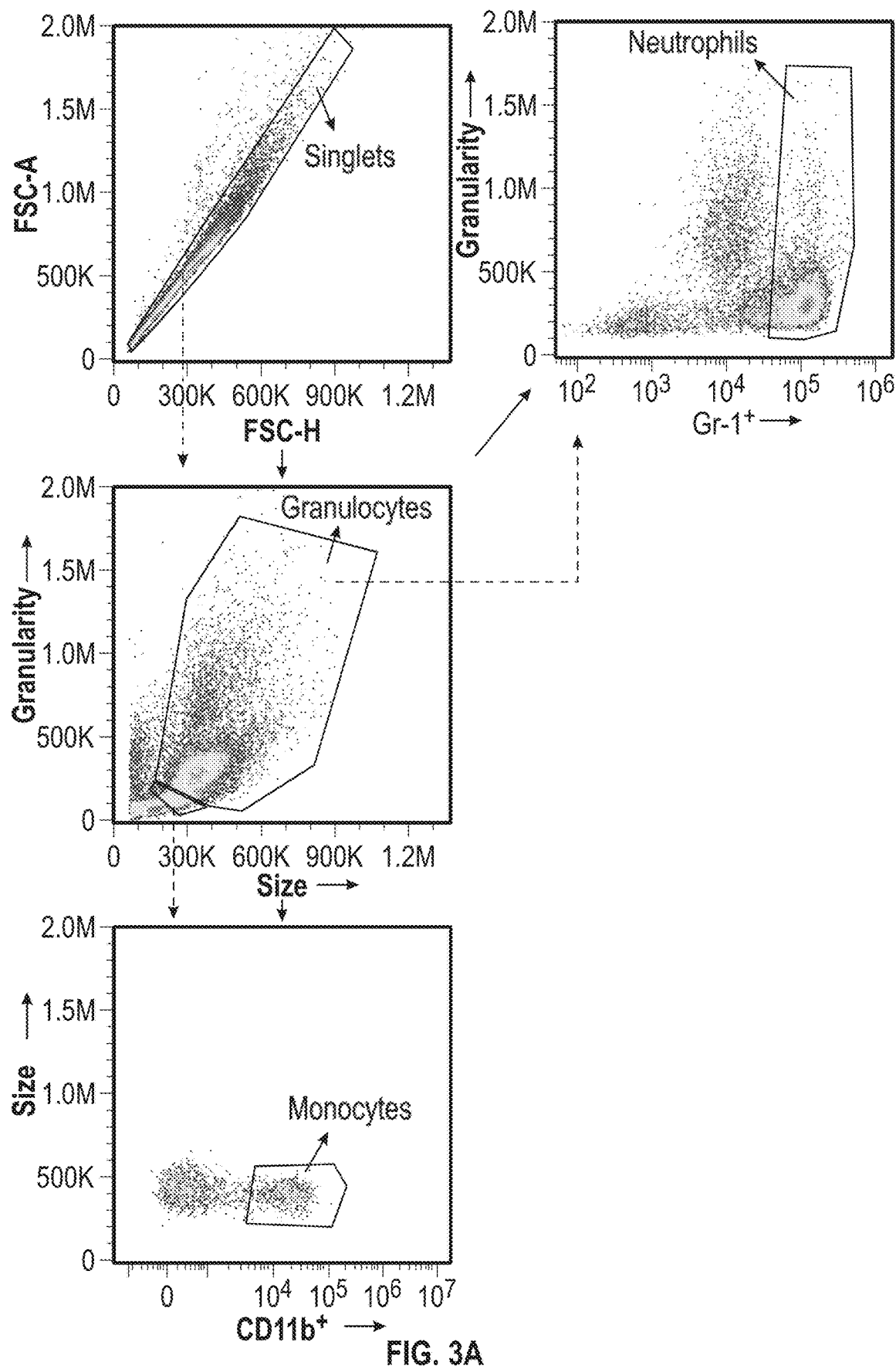
FIG. 3A-FIG. 3D depicts bone marrow tissue accumulation of the tested siRNAs. FACS analysis of bone marrow cells of CD-1 mice injected with Cy3 labelled sFLT1_2283 siRNA variants was performed.
Figure 3B:
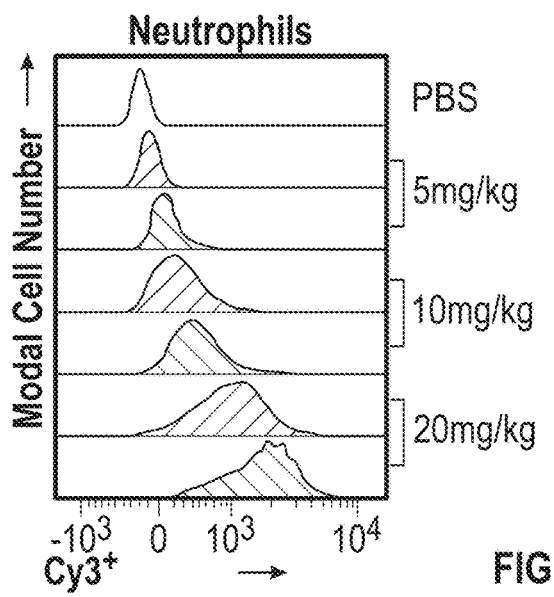
Figure 3B:
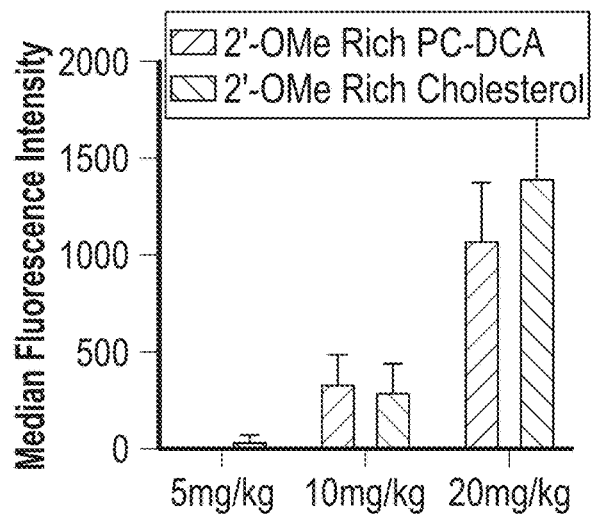
Figure 3C:
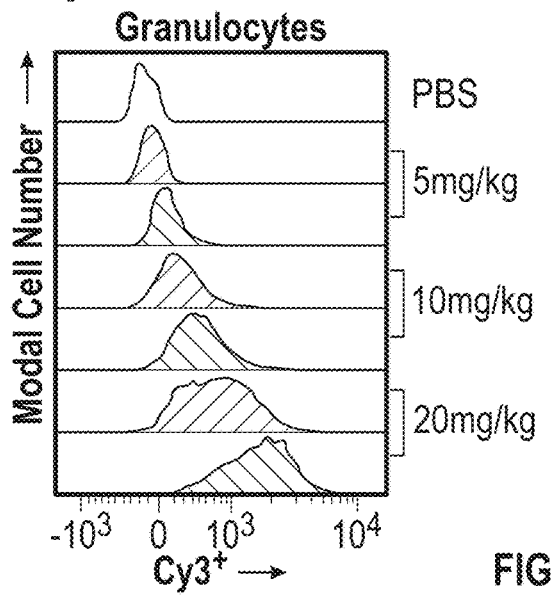
Figure 3C:
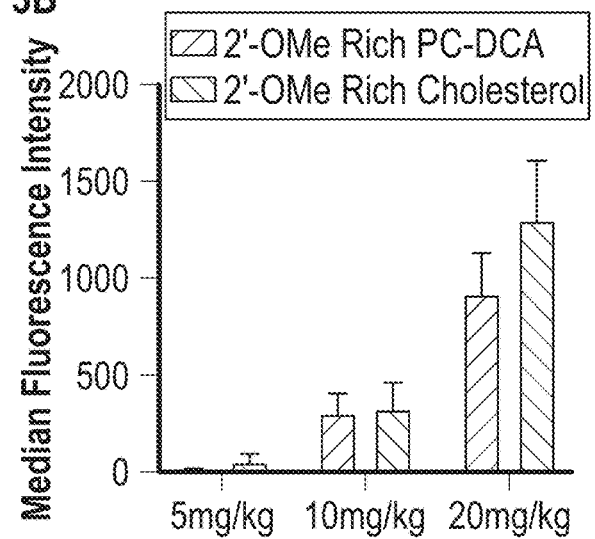
Figure 3D:
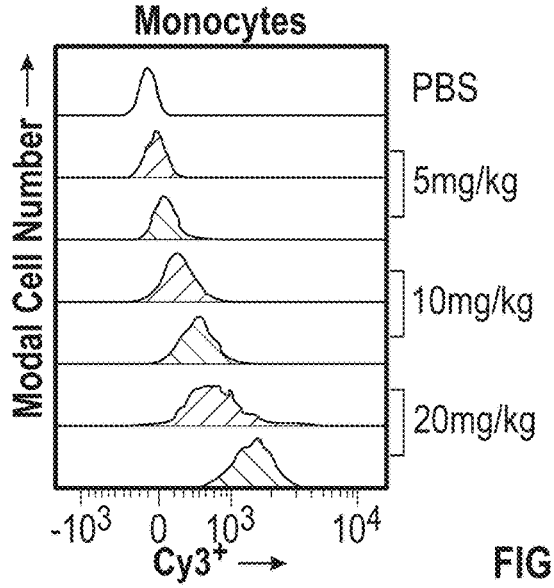
Figure 3D:
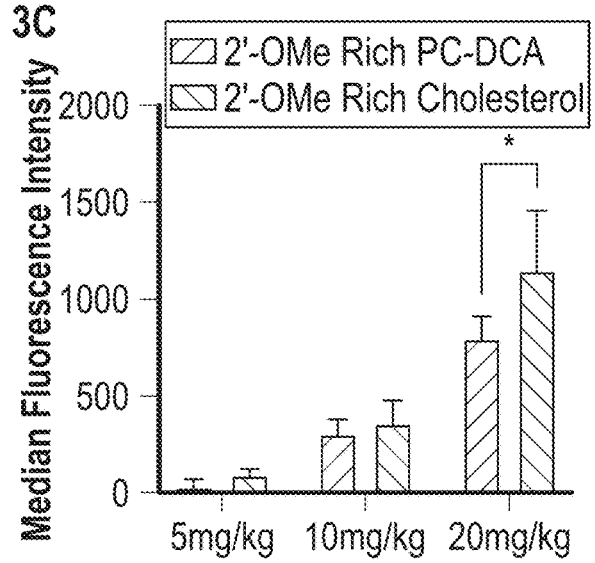

The PC-DCA siRNA conjugates were further characterized to show reduced accumulation in the bone marrow. FACS analysis of bone marrow cells of CD-1 mice injected with Cy3 labelled sFLT1_2283 siRNA variants was performed. FIG. 3A shows the gating scheme used to quantify Cy3 intensity of specific cell populations in the bone marrow in FIG. 3B-FIG. 3D. FIG. 3B shows the frequency distribution histogram of Cy3 fluorescence intensity (left) and bar graphs of Cy3 median fluorescence intensity (right) of bone marrow neutrophils 24 h post injection of siRNA variants. FIG. 3C shows the frequency distribution histogram of Cy3 fluorescence intensity (left) and bar graphs of Cy3 median fluorescence intensity (right) of bone marrow granulocytes 24 h post injection of siRNA variants. FIG. 3D shows the frequency distribution histogram of Cy3 fluorescence intensity (left) and bar graphs of Cy3 median fluorescence intensity (right) of bone marrow monocytes 24 h post injection of siRNA variants. (n=3, mean±SD) p-values describe statistically significant differences between compounds (One-way ANOVA; * p<0.05; non-significant differences not marked). The results show that the PC-DCA conjugated siRNA show lower accumulation in bone marrow monocytes, granulocytes, and neutrophils, demonstrating that the PC-DCA conjugate is useful for placental delivery with minimal off-target accumulation.

Antisense Strand 5' End Optimization

Antisense strands can be susceptible to the act of 5' exonucleases. It is therefore advantageous to protect the 5' end with a modification to reduce degradation. The siRNAs were further optimized by testing the effect of three different antisense 5' end modifications, 5' Vinyl Phosphonate (VP), 5' Phosphorothioate (PS), and 5'-hydroxyl (OH). A schematic of the siRNA chemical modification patterns.

Figure 4A:
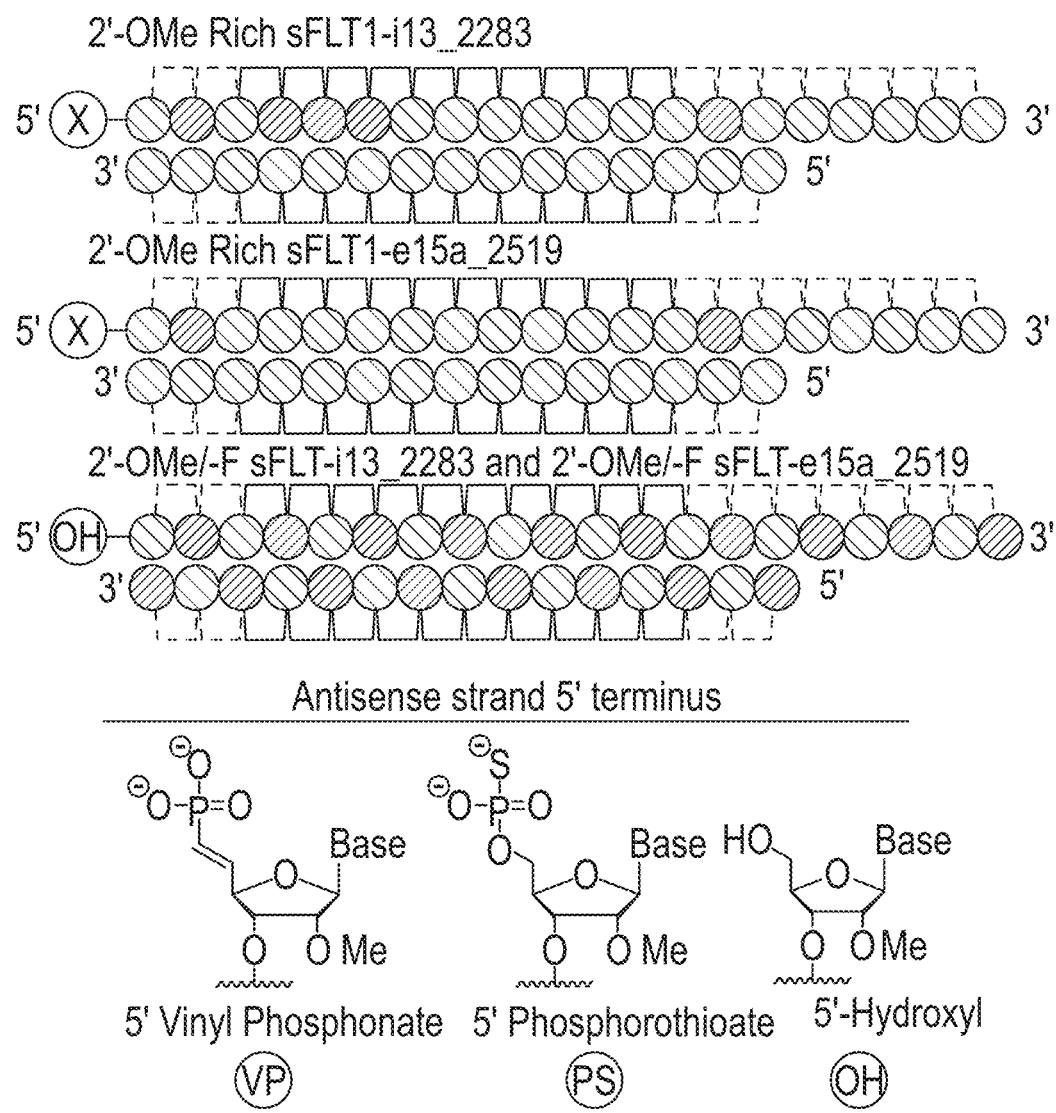
FIG. 4A-FIG. 4F depicts the impact of various 5' antisense modifications on siRNA silencing efficacy. Pregnant CD-1 mice were injected with 20 mg/kg equimolar mixture of 2283 and 2519 siRNA variants on embryonic day (E) 13 and E14.
Figure 4B:
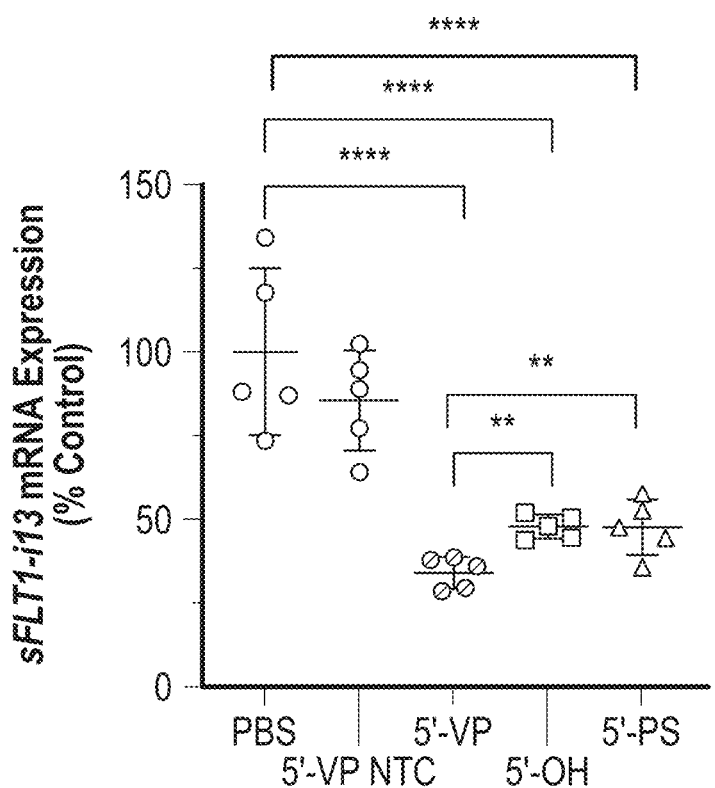

Pregnant CD-1 mice were injected with 20 mg/kg equimolar mixture of 2283 and 2519 siRNA variants on embryonic day (E) 13 and E14. FIG. 4A depicts schematic representations of the chemical pattern of siRNA compounds injected and the chemical structures of 5' moieties tested. As shown in FIG. 4B, sflt1-113 mRNA levels in placenta on E18 were measured using Quantigene 2.0 RNA Assay. Levels were normalized to Flt1 and presented as percentage of PBS control (n=5, mean±SD).

Figure 4C:
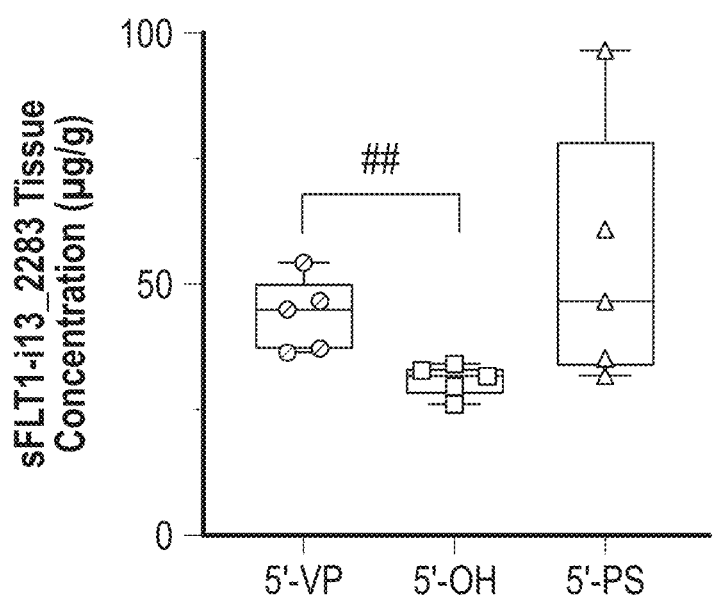
Figure 4D:
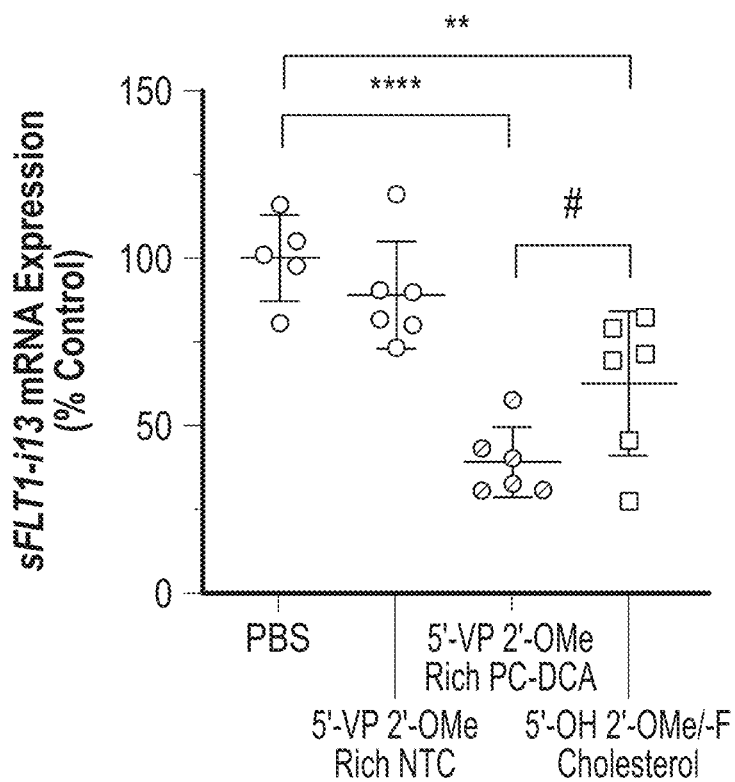
Figure 4E:
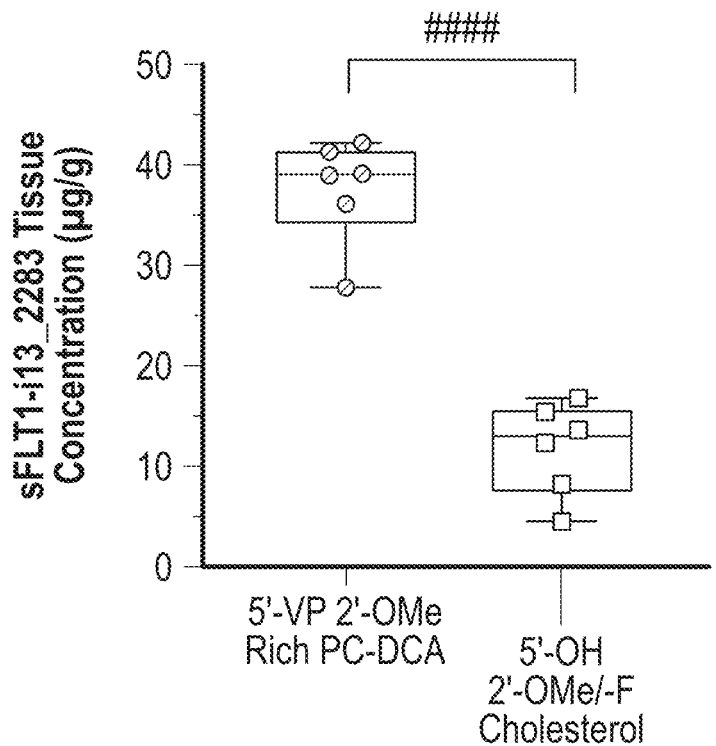
Figure 4F:
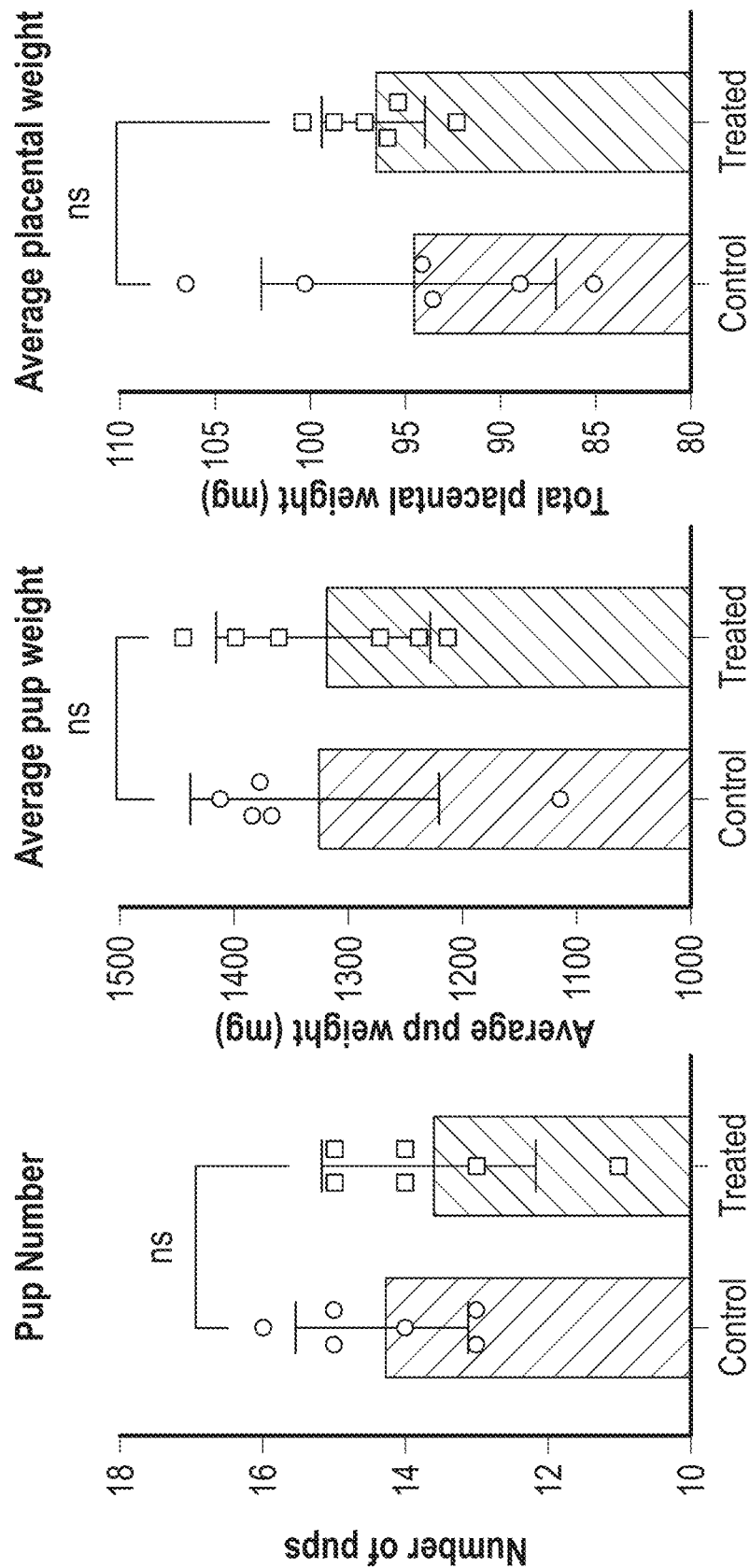

Optimization of 5' moiety, 2' modification pattern and conjugate resulted in increased tissue accumulation and efficacy in vivo. As shown in FIG. 4C, the amount of siRNA accumulation in the placenta on E18 measured using PNA hybridization assay (n=5). p-values describe statistically significant differences between compounds (One-way ANOVA;  p<0.01;  p<0.0001; non-significant differences not marked). As shown in FIG. 4D, slt 1-113 mRNA levels in placenta on E18 measured using Quantigene 2.0 RNA Assay. Levels were normalized to Flt1 and presented as percentage of PBS control (n=6, mean±SD). As shown in FIG. 4E, the amount of siRNA accumulation in the placenta on E18 measured using PNA hybridization assay (n=6). p-values describe statistically significant differences between compounds (One-way ANOVA;  p<0.01; **** p<0.0001; non-significant differences not marked. Unpaired t-test; # p<0.05; #### p<0.0001). As shown in FIG. 4F, the average mouse pup number, average pup weight, and average placental weight were approximately the same between control and treated pregnant mice, indicating that the mixture of 2283 and 2519 siRNA did not negatively impact these metrics.

Reduced Serum Cytokine Production

The optimized siRNAs were tested for their effect on serum cytokine production. The optimized siRNAs were generated to, in part, reduce toxicity and widen the therapeutic index. The reduction in the production of serum cytokines would demonstrate reduce toxicity and a wider therapeutic index.

Figure 5:
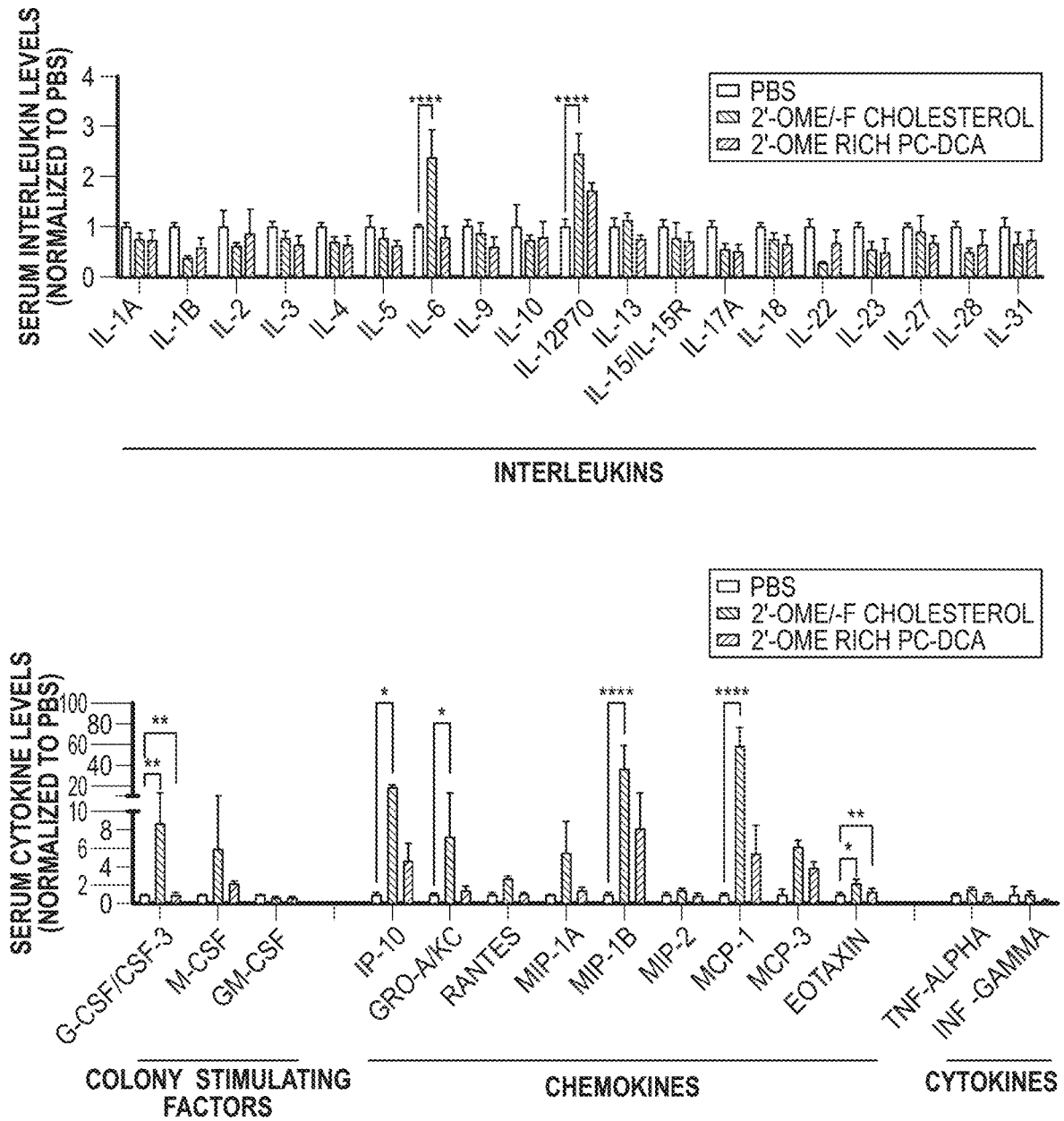
FIG. 5 depicts the impact of the optimized siRNA on serum cytokine production. Serum cytokine levels of CD-1 mice 24 h post injection with 75 mg/kg of sFLT1_2283 siRNA variants (n=3, mean±SD) were measured. p-values describe statistically significant differences between compounds (One-way ANOVA; * p<0.05; p<0.01; * p<0.001; **** p<0.0001; non-significant differences not marked).
Figure 6:
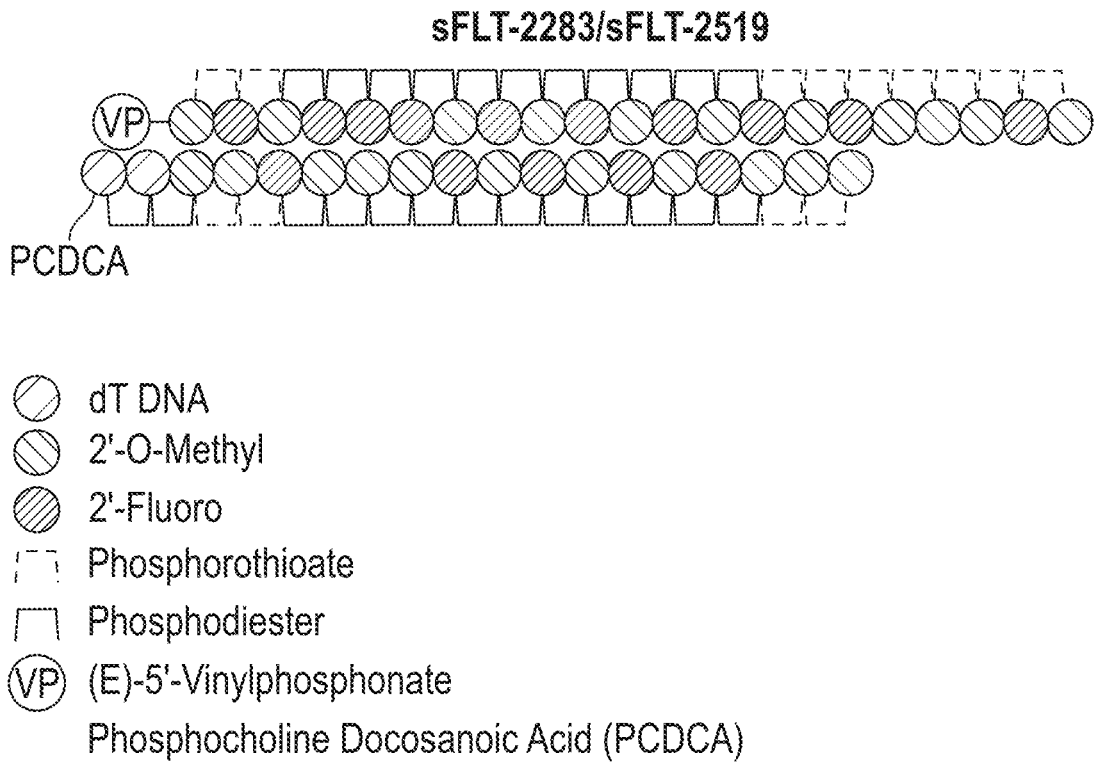
FIG. 6 depicts a schematic of an exemplary siRNA target sFLT1 2283 or 2519.

As shown in FIG. 5, serum cytokine levels of CD-1 mice 24 h post injection with 75 mg/kg of sFLT1_2283 siRNA variants (n=3, mean±SD) were measured. p-values describe statistically significant differences between compounds (One-way ANOVA; * $p<0.05$;  $p<0.01$; * $p<0.001$; **** $p<0.0001$; non-significant differences not marked). Numerous interleukin, colony stimulating factor, and chemokine levels were measured and found to be lower with the second-generation, optimized siRNA compared to the first-generation siRNAs. The wider therapeutic index means that the siRNAs can be dosed at high concentrations without the risk of toxicity issues. This may lead to reduced frequency of administration and/or better silencing of sFLT-1.

The overall results of Example 2 show that the optimized siRNAs targeting the sFlt-1 2283 and 2519 target sites, when compared against the first-generation siRNAs, had similar silencing efficacy with superior placental tissue accumulation, reduced off-target tissue accumulation, reduced degradation, reduced toxicity, and a wider therapeutic index.

Assay Systems in Place to Evaluate Lead Compounds.

The assays and models developed so far are as follows.

Fluorescence Microscopy Evaluation of In Situ Tissue Distribution hsiRNA variants with a Cy3 or Cy5.5 (lower auto-fluorescence) dye attached through a non-degradable linker to the 5' end of sense (passenger) strand were synthesized. This compound was biologically stable with no detectable Cy3 cleavage within 24 hours. The fluorescent sense strand hybridized to its complementary guide strand (thus forming a double-stranded hsiRNA) was administrated to animals and oligonucleotide distribution patterns were examined in 4 μm tissue sections also stained with DAPI or/and cell type selective antibodies. Parallel sections could be stained with standard histology markers enabling detailed histology mapping. Because hsiRNAs are already heavily hydrophobically modified, dye addition has little effect on overall hydrophobicity and therefore minimal impact on oligonucleotide distribution. This assay allowed rapid evaluation of tissue and cell-type distribution and was complemented by a PNA-based quantitative assay for direct guide strand detection.

PNA Hybridization for Quantitative Guide Strand Detection in Tissue Lysates

To enable direct quantification of intact guide stand in tissues, a novel assay was developed and implemented wherein the guide strand was hybridized to a fully complementary Cy3-labeled PNA (peptide nucleic acid) oligonucleotide, and the corresponding duplex was separated from excess single stranded PNA by HPLC. Since PNA is non-charged and has extremely tight binding to the guide strand, it out-competes both the hsiRNA sense strand and any endogenous target sequences. Fluorescence detection of the Cy3-PNA:guide hybrid provided a direct measure of guide strand abundance in tissue lysates. In conjunction with an HPLC auto injector, this assay enabled guide strand quantification in hundreds of samples overnight. The assay was also highly sensitive, with a limit of detection less than 10 fmole/gram, and hybrids containing full-length, partially degraded, 5'-phosphorylated and 5'-dephosphorylated guide strand can all be quantified as separate peaks or shoulders in the HPLC trace. Because this assay could detect both labeled and unlabeled compounds, it can be directly transitioned to future CRO's for clinical sample analysis.

QuantiGene® (Affymetrix) Assay for Direct Detection of Flt1 mRNA Variants in Cells and Tissues QuantiGene® is a highly sensitive 96-well based assay in which mRNA is directly detected through signal amplification directly from tissue and/or cell lysates. By linking this direct detection assay to a 192 well automatic TissueLyser, a high-throughput version was developed which enabled processing of dozens of samples per animal. Thus, quantitative data on expression of targeted and housekeeping genes was generated in many animals at once. In pilot studies, n=8 was sufficient to detect 40% modulation of sFlt1 mRNA isoform expression with 80% confidence. bDNA assays are described in Coles et al. *Nucleic Acid Ther.* (2015) Nov. 23. PMID: 26595721.

ELISA (#MVR100, R&D Systems) for Detection of sFLT1 Proteins in Conditioned Media and Blood This 96-well based assay required only 10 μL of biological fluid per sample. This assay has been optimized over many years for both in vitro and in vivo studies. It is clinically compatible and allows for evaluation of circulating sFLT1 protein levels without animal sacrifice, and will be particularly useful for non-human primate studies.

Normal Mouse Pregnancy Model

The sFlt1-i13 variants are expressed during mouse pregnancy with i13 levels exponentially increasing from days 14-19. Perfect homology between the sFLT1-i13-2283 compound and the i13 mouse variant allows the study both of efficacy and of safety in this simple rodent model.

Preeclampsia Models

Reduced Uterine Perfusion Pressure (RUPP) model of placental ischemia and hypoxia model of preeclampsia is used as described further below.

Baboon Wild-Type Pregnancy Model

The sFlt1-i15a variant is not expressed in rodents during pregnancy, thus overall combination efficacy and safety will be evaluated in wild-type pregnant baboons using ELISA, a non-invasive assay as readout of efficacy.

Example 3. Optimized siRNAs Targeting sFlt-1 In Vitro and in RUPP Rat Model of Preeclampsia Optimized siRNAs targeting sFlt-1 were tested in vitro using a human cell line and in the RUPP rat model of preeclampsia. The following siRNA were used in this example:

|  | Sequence | Molecular Formula of the sodium salt | Molecular Formula of the free acid |
|---|---|---|---|
| sFLT-2283 | Combined sense and antisense strand | $C_{434}H_{527}F_{15}N_{150}Na_{40}O_{250}P_{40}S_{13}$ | $C_{434}H_{567}F_{15}N_{150}O_{250}P_{40}S_{13}$ |
| sFLT-2283 Antisense strand | V(mU)#(fA)#(mA)(fA)(fU)(fU)(mU) (fG)(mG)(fA)(mG)(fA)(mU)(fC) #(mC)#(fG)#(mA)#(mG)#(mA)#(fG) #(mA) (SEQ ID NO: 17) | $C_{215}H_{239}F_{10}N_{86}Na_{22}O_{125}P_{21}S_9$ | $C_{215}H_{261}F_{10}N_{86}O_{125}P_{21}S_9$ |
| sFLT-2283 Sense strand | (mC)#(mG)#(mG)(fA)(mU)(fC) (mU)(fC)(mC)(fA)(mA)(mA)(mU) (fU)#(mU)#(mA)(T)(T)-PCDCA (SEQ ID NO: 18) | $C_{219}H_{288}F_5N_{64}Na_{18}O_{125}P_{19}S_4$ | $C_{219}H_{306}F_5N_{64}O_{125}P_{19}S_4$ |

| Sequence | | Molecular Formula of the sodium salt | Molecular Formula of the free acid |
|---|---|---|---|
| sFLT-2519 | Combined sense and antisense strand | $C_{433}H_{524}F_{15}N_{145}Na_{40}O_{252}P_{40}S_{13}$ | $C_{433}H_{564}F_{15}N_{145}O_{252}P_{40}S_{13}$ |
| sFLT-2519 Antisense strand | V(mU)#(fA)#(mU)(A)(fA)(fA)(mU)(fG)(mG)(fU)(mA)(fG)(mC)(fU)#(mA)#(fU)#(mG)#(mA)#(mU)#(fG)#(mA) (SEQ ID NO: 19) | $C_{214}H_{237}F_{10}N_{82}Na_{22}O_{127}P_{21}S_9$ | $C_{214}H_{259}F_{10}N_{82}O_{127}P_{21}S_9$ |
| sFLT-2519 Sense strand | (mA)#(mU)#(mA)(fG)(mC)(fU)(mA)(fC)(mC)(fA)(mU)(mU)(mU)(fA)#(mU)#(mA)(T)(T)-PCDCA (SEQ ID NO: 20) | $C_{219}H_{287}F_5N_{63}Na_{18}O_{125}P_{19}S_4$ | $C_{219}H_{305}F_5N_{63}O_{125}P_{19}S_4$ |

Legend: m = 2'-O-methyl; f = 2'-fluoro; T = Thymidine; # = Phosphorothioate; V = 5'-Vinylphosphonate; PCDCA = 3'-C7-Phosphocholine-docosanoic acid conjugate through phosphate linker.

FIG. 9, FIG. 10A-FIG. 10B, and FIG. 11A-FIG. 11B depict the optimized sFlt-1 targeting siRNA (sFLT-2283 and sFLT-2519).

Figure 7:
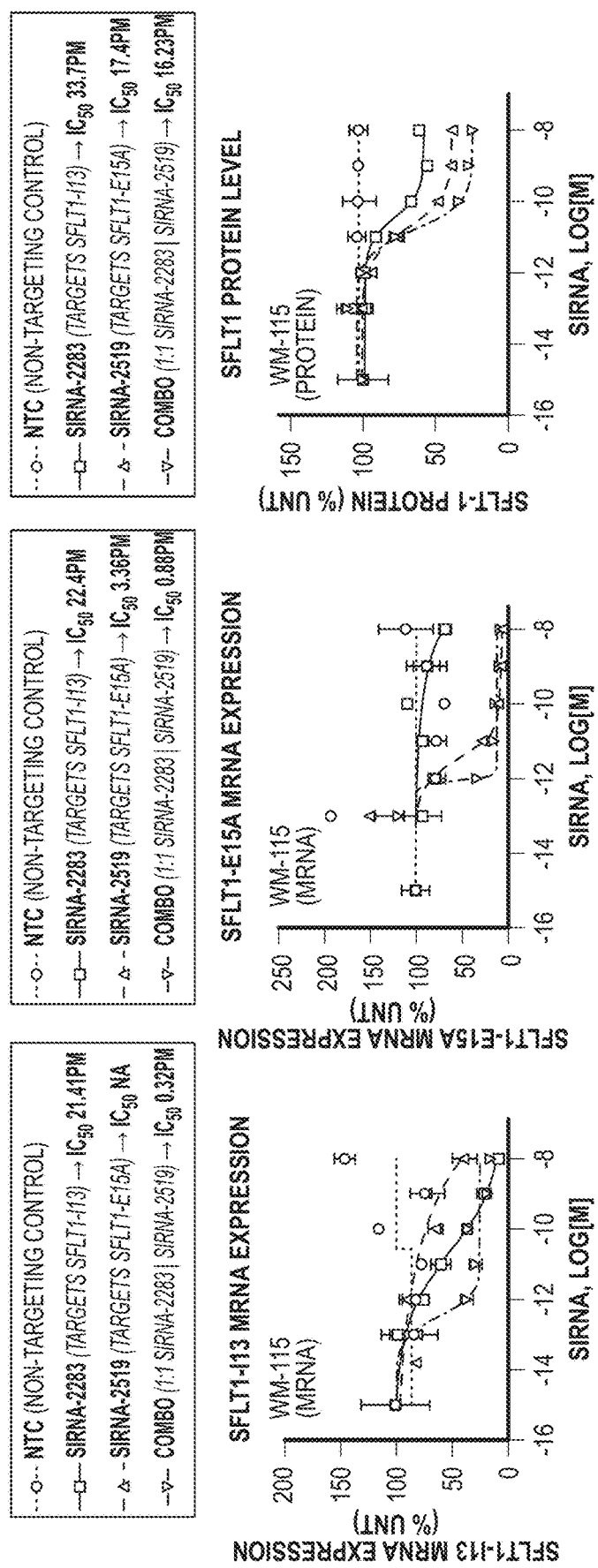
FIG. 7 depicts dose response curves of siRNA-2238 and siRNA-2519 silencing sFLT1-i13 and sFLT1-e15a (respectively), or a combination of the two siRNAs (1:1 siRNA-2238:siRNA-2519). sFLT1-i13 and sFLT1-e15a mRNA expression levels and sFLT1 protein levels were measured at each of the tested siRNA concentrations.

The optimized siRNA were tested in the human WM-115 cell line to analyze the ability of siRNA-2283 and siRNA-2519 to silence their targets. siRNA-2283 (targets sFLT1-i13) and siRNA-2519 (targets sFLT1-e15a) were tested alone or in combination in a 1:1 ratio. As shown in FIG. 7, each siRNA alone was capable of silencing their target sFLT1 mRNA isoform and reducing total sFLT1 protein levels, while the combination demonstrated even greater silencing of individual isoforms and total protein reduction.

The same siRNA were tested in combination in the RUPP (Reduced Uteroplacental Perfusion Model in Pregnant Rats) rat model of pre-eclampsia. The RUPP procedure induces placental ischemia and is a well characterized model of preeclampsia. RUPP rats show hallmark symptoms of preeclampsia, including increased maternal mean arterial blood pressure (MAP) and decreased glomerular filtration rate (GFR) that is accompanied by elevated sFLT1 levels.

Figure 8A:
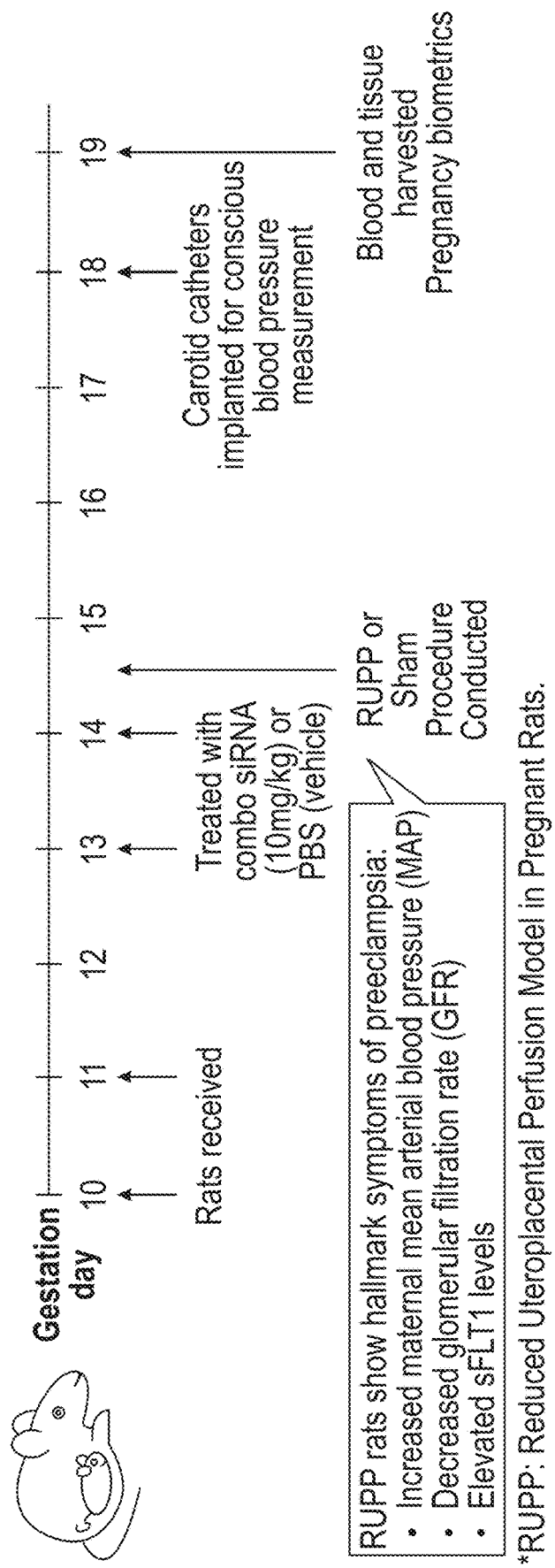
FIG. 8A-FIG. 8C depicts in vivo experiments performed in the Reduced Uteroplacental Perfusion Model in Pregnant Rats (RUPP).

To evaluate the optimized siRNAs targeting sFlt1 in the RUPP model, rats were injected subcutaneously with 10 mg/kg body weight of the combination siRNA therapy (sFLT1 siRNA: (1:1 mixture of siRNA-2283 (sFLT1-i13-targeting) and siRNA-2519 (sFLT1-e15a-targeting)) or a PBS control on gestation days 13 and 14 (see FIG. 8A).

To generate the RUPP model, silver clips were surgically placed around the abdominal aorta and ovarian arteries in the uterus of pregnant Sprague Dawley rats on gestational day 14. Sham surgeries (abdominal incisions and suturing without clip placement) were used as controls.

Blood and tissue were harvested on gestational day 19 and pregnancy biometrics were analyzed. Blood pressure was measured in conscious rats on gestational day 19 and then animals were anesthetized with isoflurane to blood for measurements of sFLT-1 and tissues were collected for histological analysis.

The following assays were performed:

Maternal Blood Pressure Measurements: on gestational day 18, carotid catheters were implanted for measurement of conscious arterial blood pressure and heart rates on day 19.

Fetal and Placental Weights: on gestational day 19, at the time of terminal sacrifice, fetal and placental weights were measured. Total and average fetal and placental weights were calculated per rat.

Fetal Absorption: visually determine the number of fetuses that were absorbed by the mother.

Figure 8B:
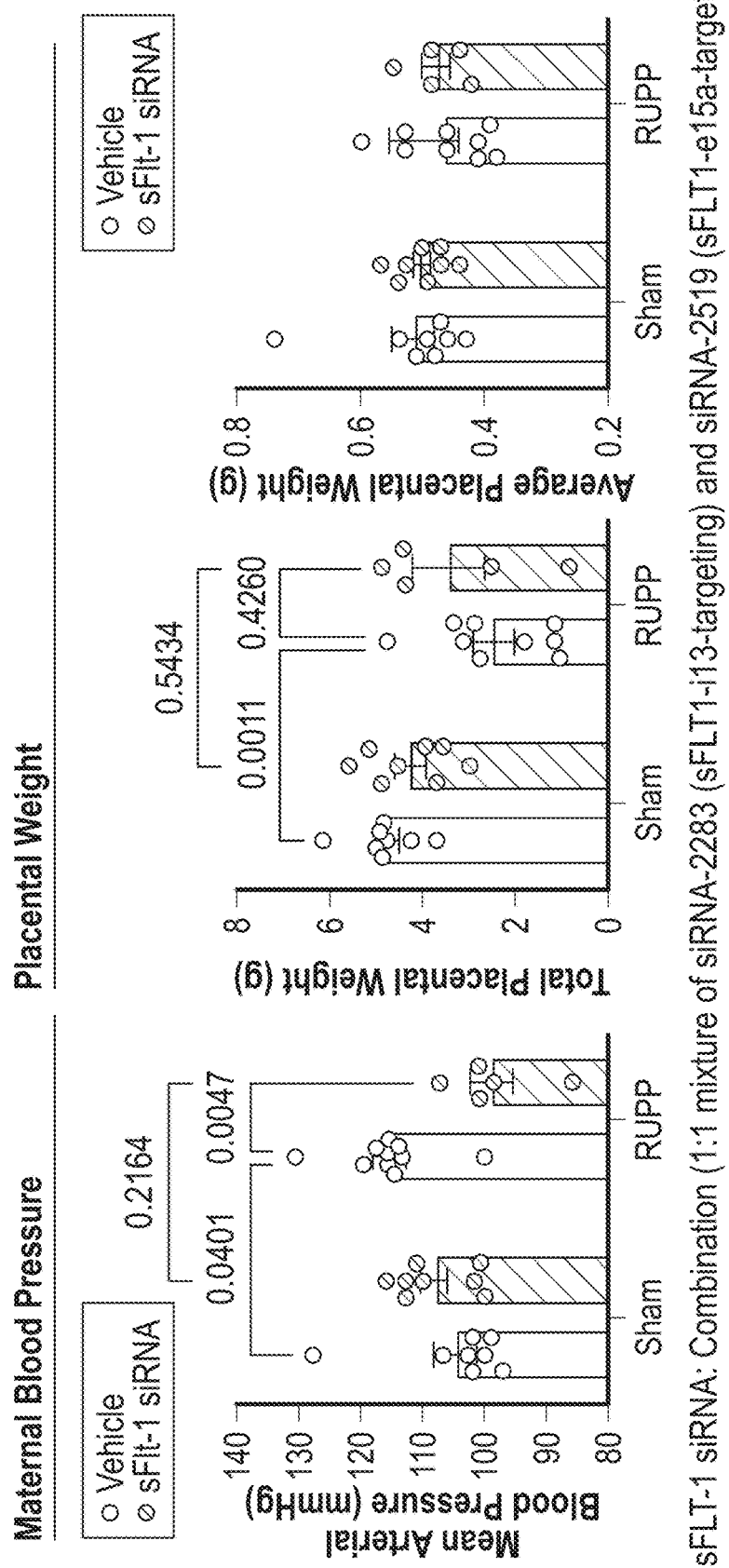
Figure 8C:
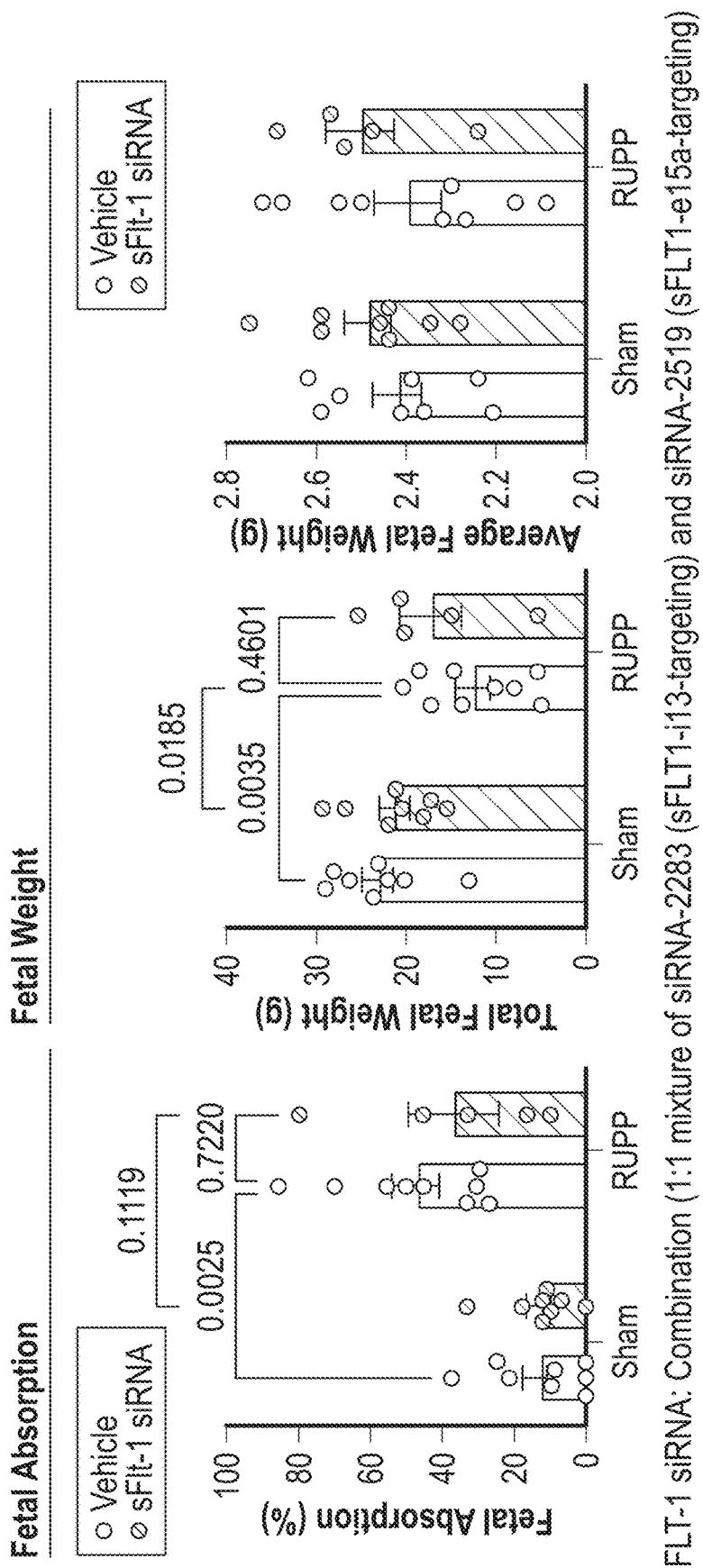
Figure 9:
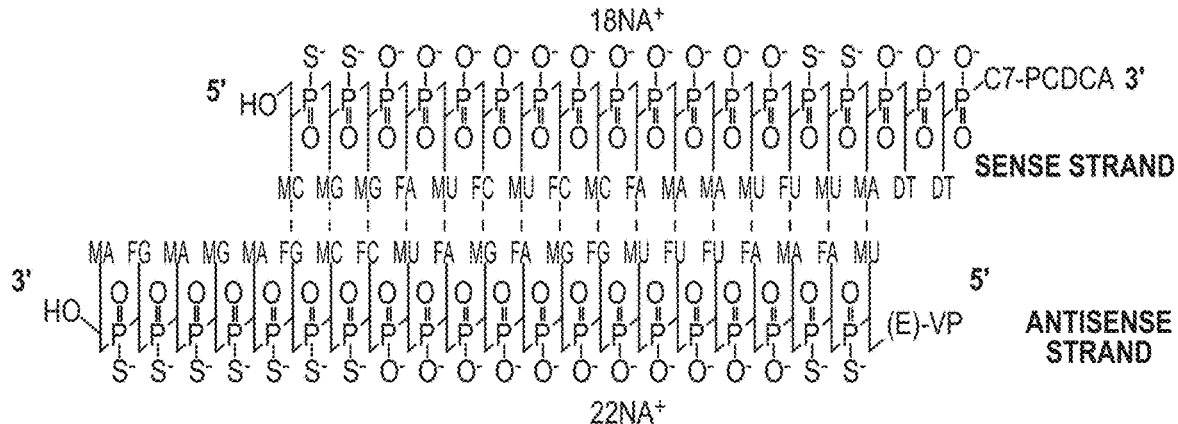
FIG. 9 depicts the chemical structure of the optimized siRNA molecules sFLT1 2283 and sFLT1 2519.
Figure 9:
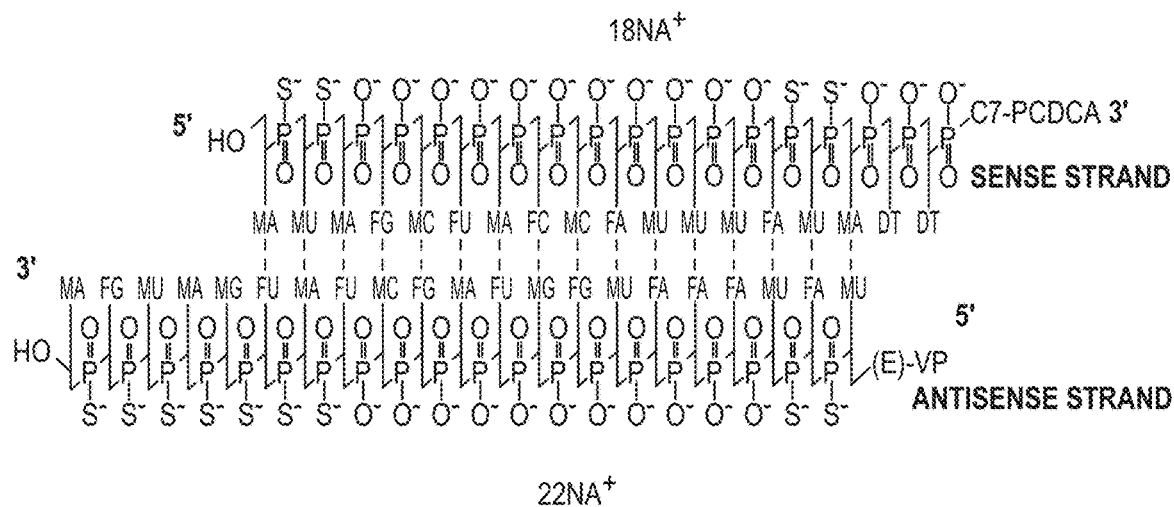
Figure 9:
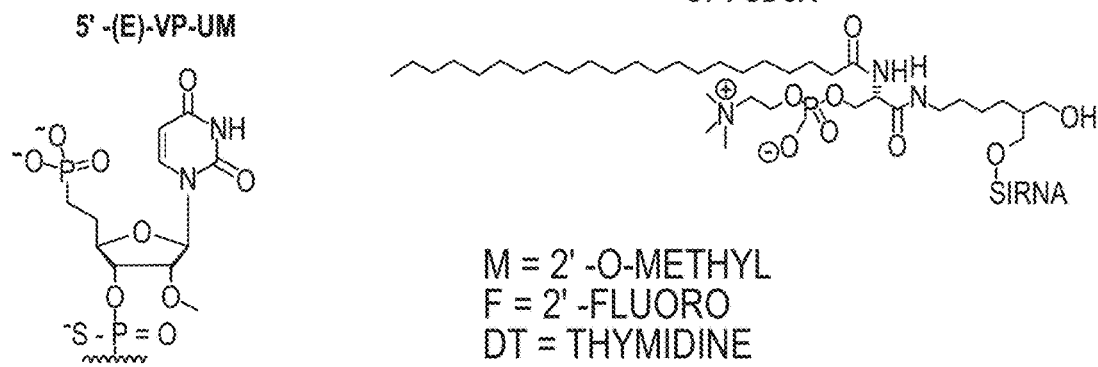
Figure 10A:
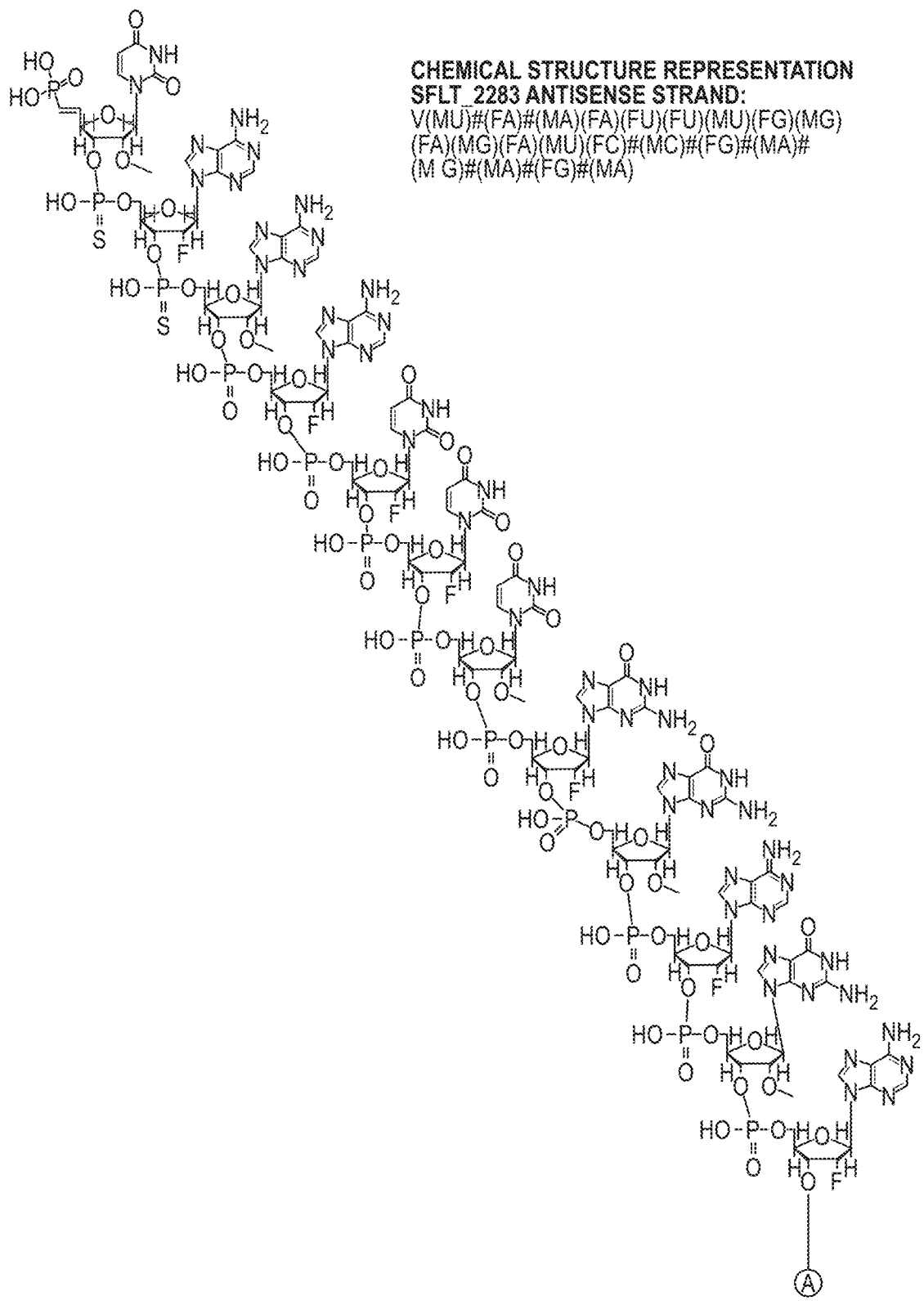
FIG. 10A-FIG. 10B depict the chemical structure of the optimized siRNA molecule sFLT1 2283.
Figure 10A:
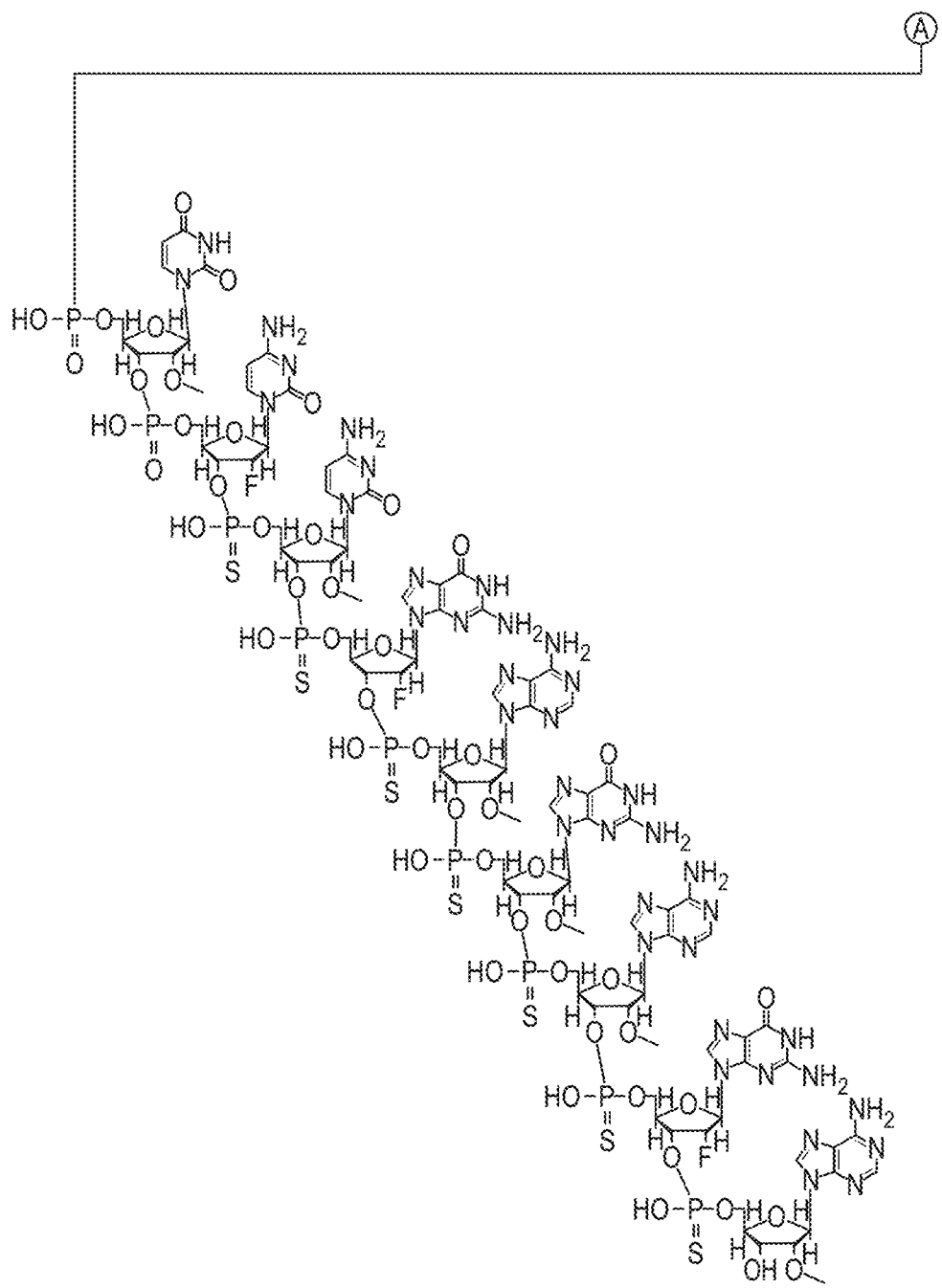
Figure 10B:
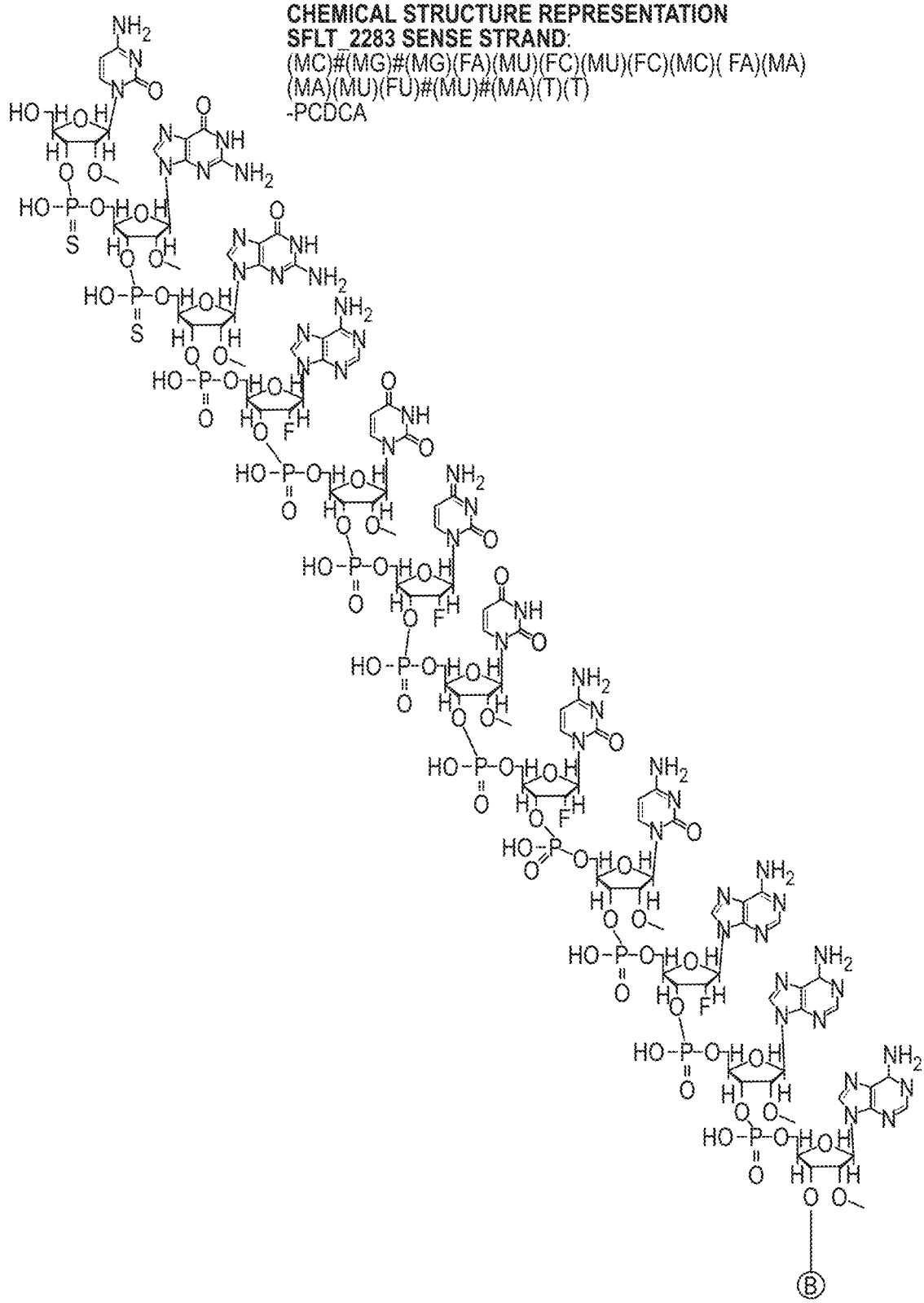
Figure 10B:
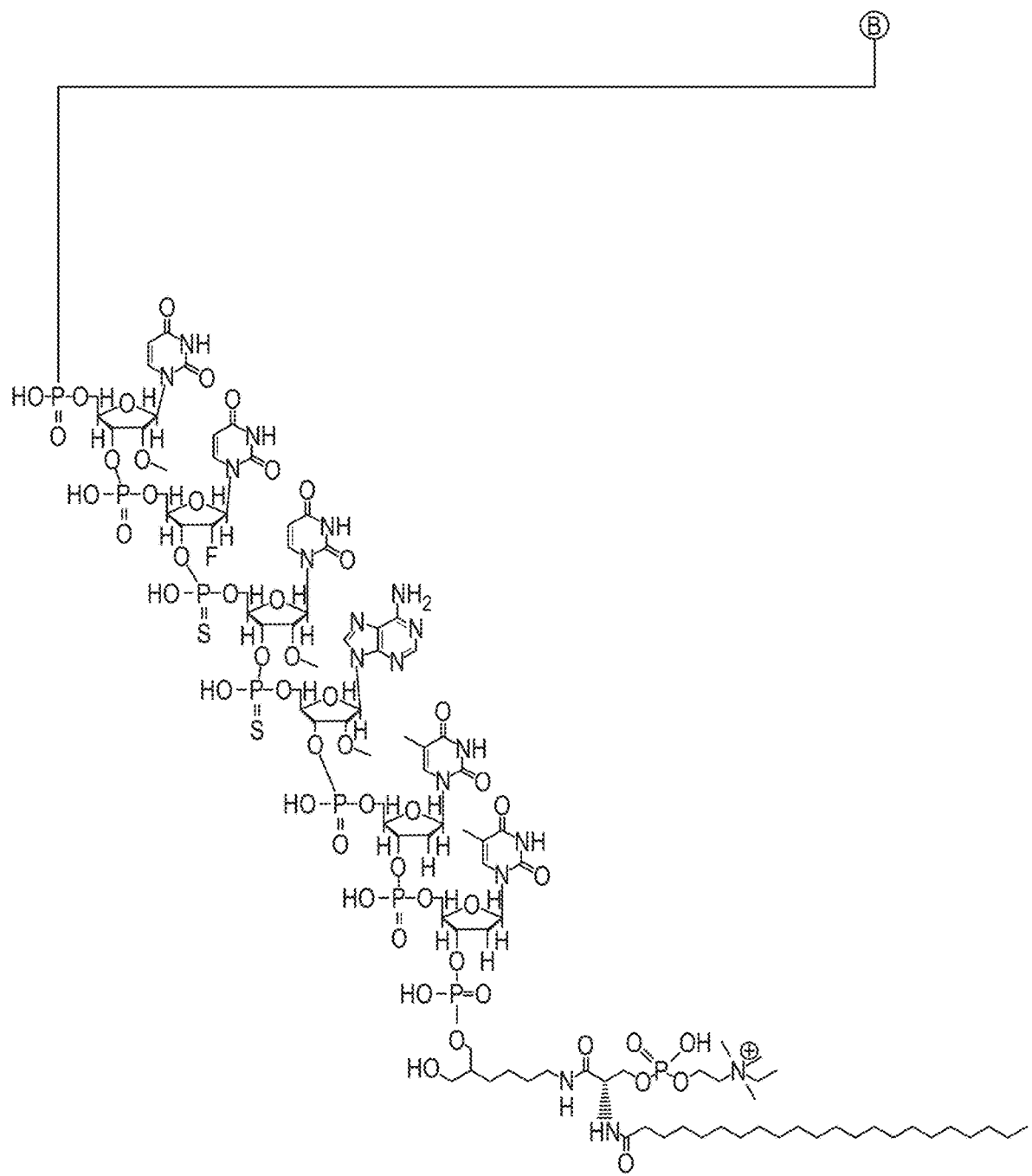
Figure 11A:
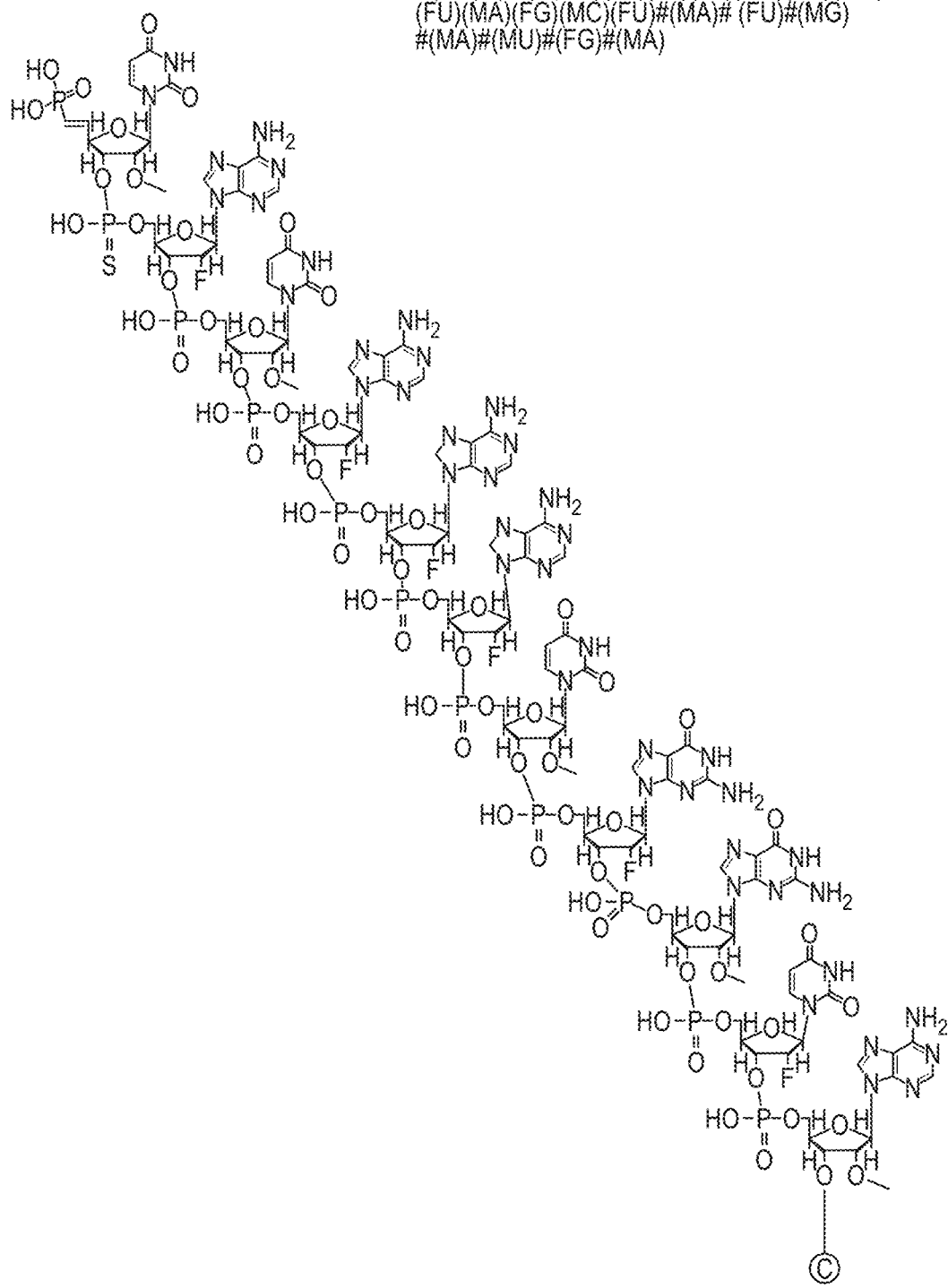
FIG. 11A-FIG. 11B depict the chemical structure of the optimized siRNA molecule sFLT1 2519.
Figure 11A:
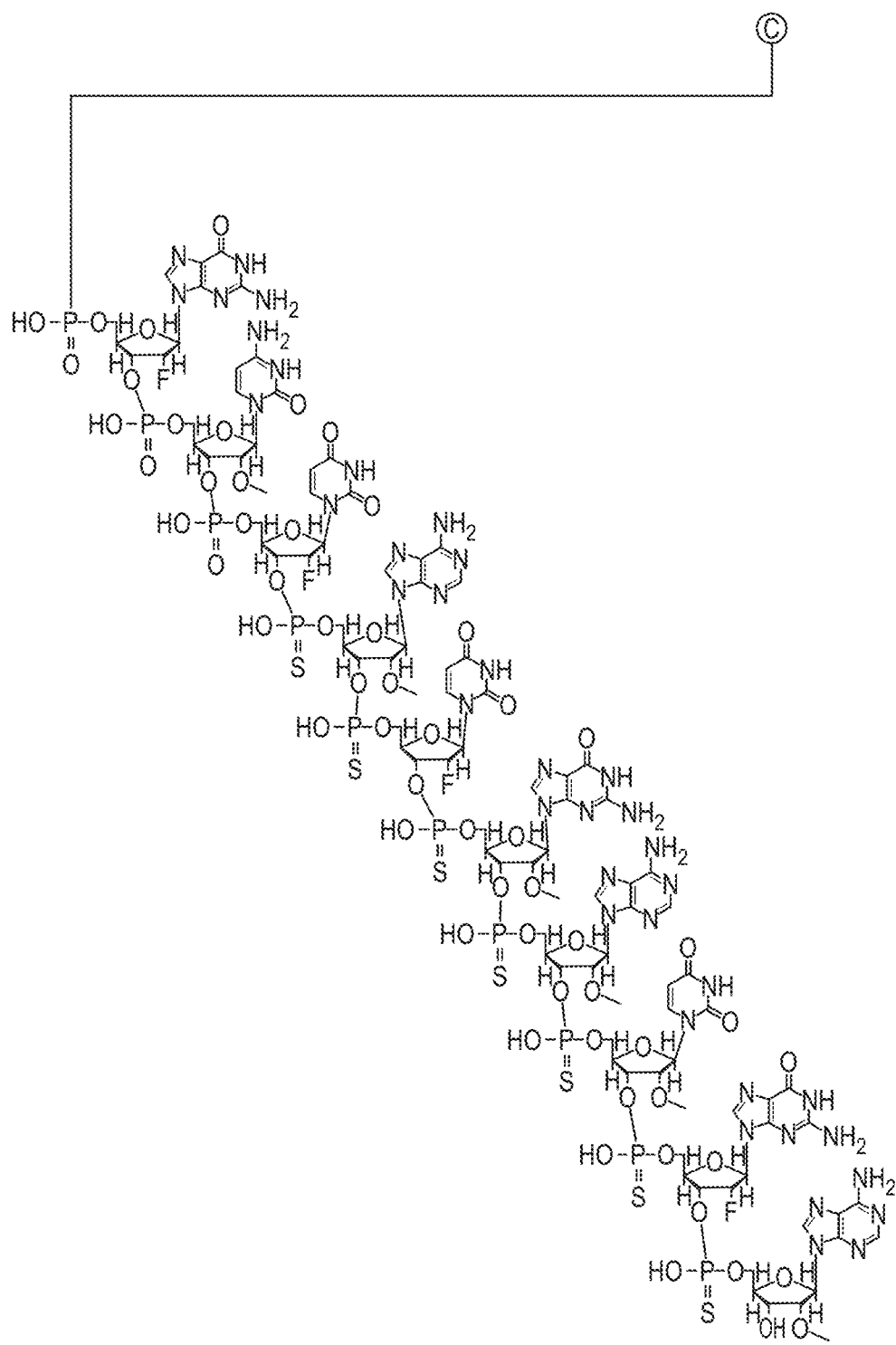
Figure 11B:
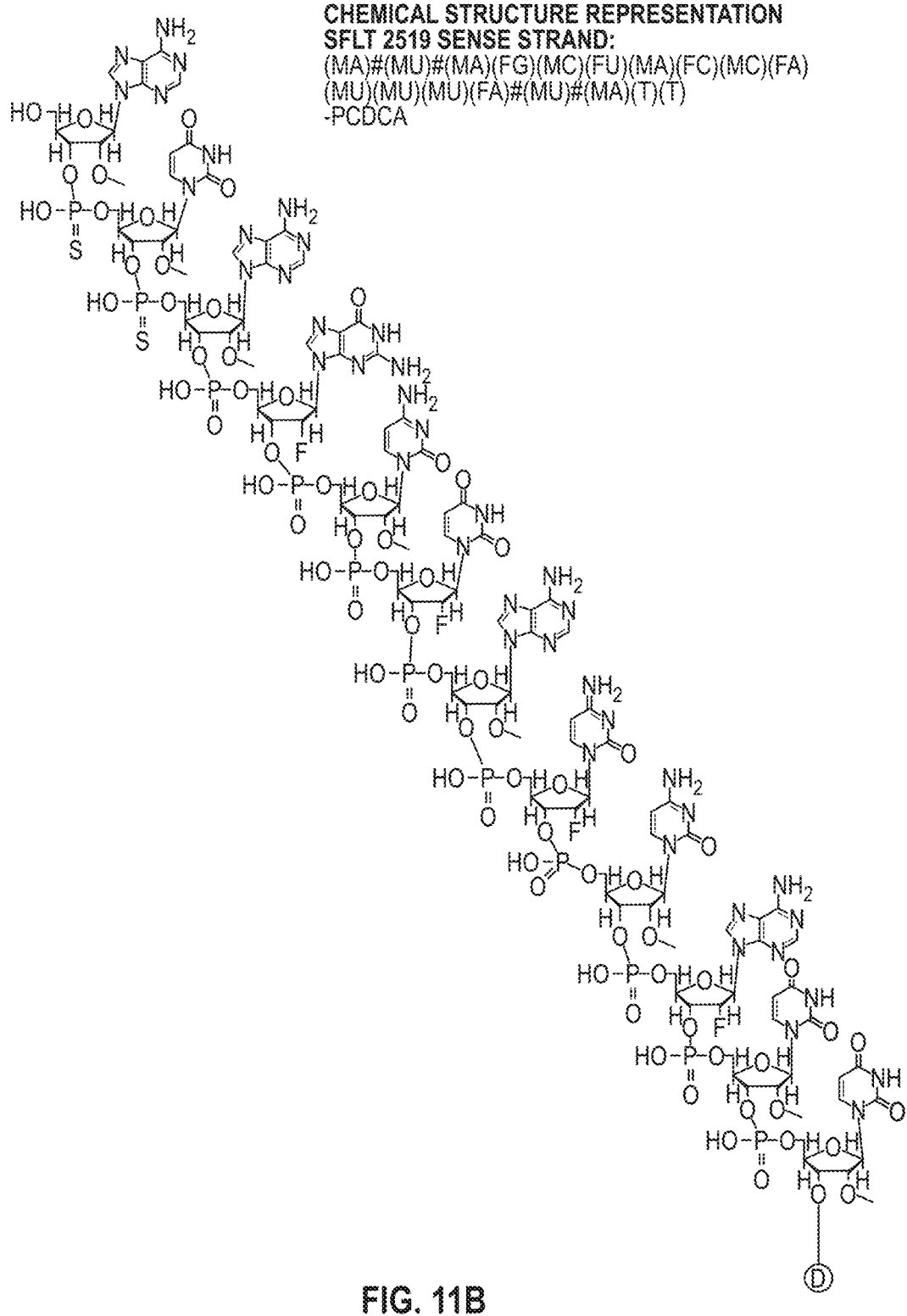
Figure 11B:
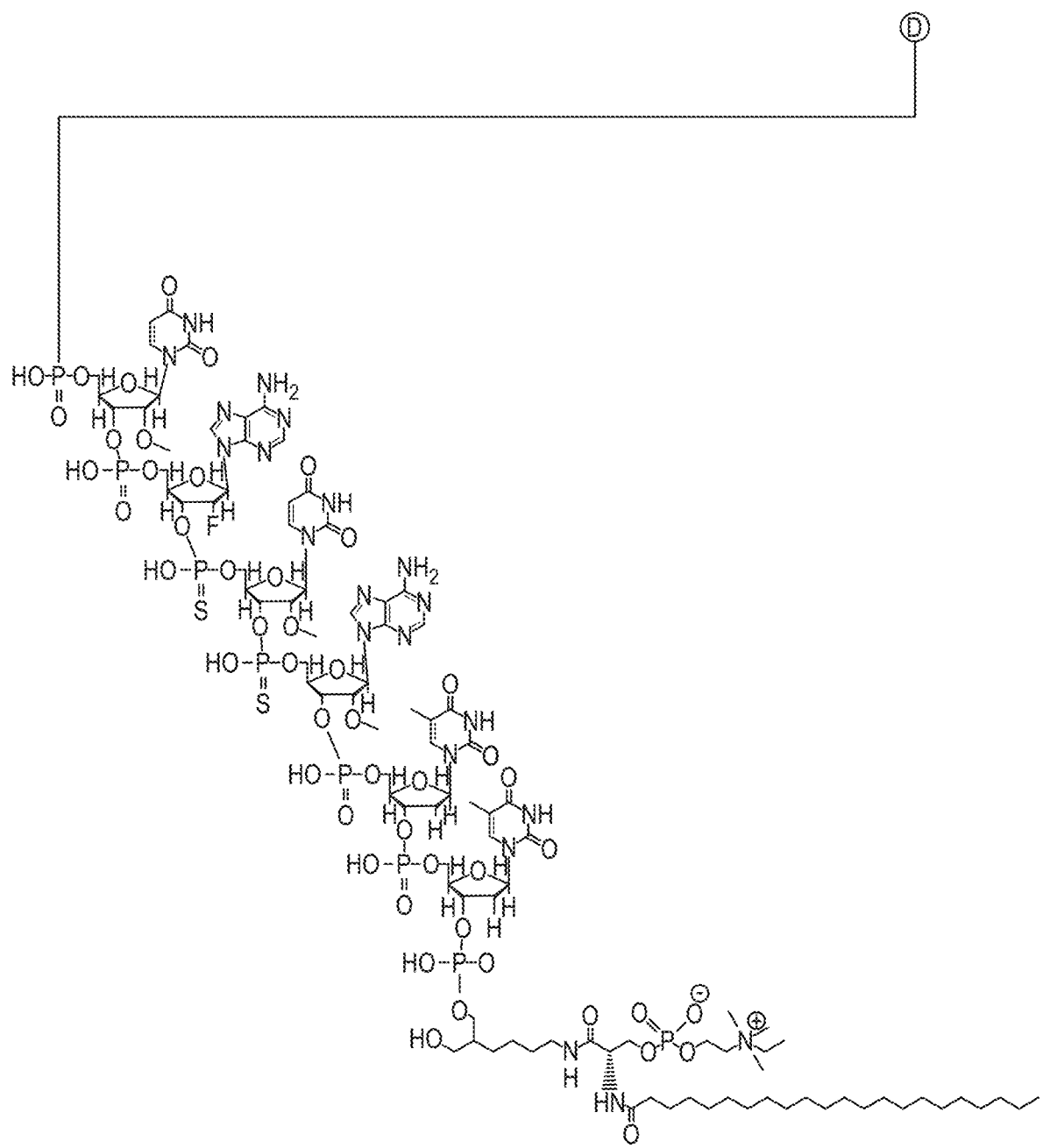

As shown in FIG. 8B, maternal blood pressure was reduced in the combination therapy RUPP group, bringing blood pressure to control levels (Sham). Moreover, placental weight was preserved in the RUPP group treated with the combination therapy (FIG. 8B). As measured by fetal absorption and fetal weight (shown in FIG. 8C), there were no fetal adverse effects and a trend toward improved fetal growth.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A double stranded RNA (dsRNA), wherein said dsRNA comprises an antisense strand and a sense strand, each strand with a 5' end and a 3' end, wherein:
   (1) the antisense strand comprises (mU)#(fA)#(mA)(fA)(fU)(fU)(mU)(fG)(mG)(fA)(mG)(fA)(mU)(fC)#(mC)#(fG)#(mA)#(mG)#(mA)#(fG)#(mA) (SEQ ID NO: 12) or a salt thereof; and
   (2) the sense strand comprises (mC)#(mG)#(mG)(fA)(mU)(fC)(mU)(fC)(mC)(fA)(mA)(mA)(mU)(fU)#(mU)#(mA) (SEQ ID NO: 13) or a salt thereof,
   wherein "m" corresponds to a 2'-O-methyl modification, "f" corresponds to a 2'-fluoro modification, "#" corresponds to a phosphorothioate internucleotide linkage.

2. A double stranded RNA (dsRNA), wherein said dsRNA comprises an antisense strand and a sense strand, each strand with a 5' end and a 3' end, wherein:
   (1) the antisense strand comprises (mU)#(fA)#(mU)(fA)(fA)(fA)(mU)(fG)(mG)(fU)(mA)(fG)(mC)(fU)#(mA)#(fU)#(mG)#(mA)#(mU)#(fG)#(mA) (SEQ ID NO: 16) or a salt thereof; and
   (2) the sense strand comprises (mA)#(mU)#(mA)(fG)(mC)(fU)(mA)(fC)(mC)(fA)(mU)(mU)(mU)(fA)#(mU)#(mA) (SEQ ID NO: 15) or a salt thereof,
   wherein "m" corresponds to a 2'-O-methyl modification, "f" corresponds to a 2'-fluoro modification, "#" corresponds to a phosphorothioate internucleotide linkage.

3. The dsRNA of claim 1, wherein:
   (1) the antisense strand comprises V(mU)#(fA)#(mA)(fA)(fU)(fU)(mU)(fG)(mG)(fA)(mG)(fA)(mU)(fC)#(mC)#(fG)#(mA)#(mG) #(mA)#(fG)#(mA) (SEQ ID NO: 17) or a salt thereof; and
   (2) the sense strand comprises (mC)#(mG)#(mG)(fA)(mU)(fC)(mU)(fC)(mC)(fA)(mA)(mA)(mU)(fU)#(mU)#(mA)(T)(T)-PCDCA (SEQ ID NO: 18) or a salt thereof,
   wherein "m" corresponds to a 2'-O-methyl modification, "f" corresponds to a 2'-fluoro modification, "T" corresponds to a thymidine DNA nucleotide, "#" corresponds to a phosphorothioate internucleotide linkage, "V" corresponds to a 5'-vinylphosphonate, and "PCDCA" corresponds to a 3'-C7-phosphocholine-docosanoic acid conjugate through a phosphate linker.

4. The dsRNA of claim 2, wherein:
   (1) the antisense strand comprises V(mU)#(fA)#(mU)(fA)(fA)(fA)(mU)(fG)(mG)(fU)(mA)(fG)(mC)(fU)#(mA)#(fU)#(mG)#(mA) #(mU)#(fG)#(mA) (SEQ ID NO: 19) or a salt thereof; and
   (2) the sense strand comprises (mA)#(mU)#(mA)(fG)(mC)(fU)(mA)(fC)(mC)(fA)(mU)(mU)(mU)(fA)#(mU)#(mA)(T)(T)-PCDCA (SEQ ID NO: 20) or a salt thereof,
   wherein "m" corresponds to a 2'-O-methyl modification, "f" corresponds to a 2'-fluoro modification, "T" corresponds to a thymidine DNA nucleotide, "#" corresponds to a phosphorothioate internucleotide linkage, "V" corresponds to a 5'-vinylphosphonate, and "PCDCA" corresponds to a 3'-C7-phosphocholine-docosanoic acid conjugate through a phosphate linker.
5. The dsRNA of claim 1, wherein:
(1) the antisense strand comprises Formula I (SEQ ID NO: 27), or a salt thereof:
Formula I
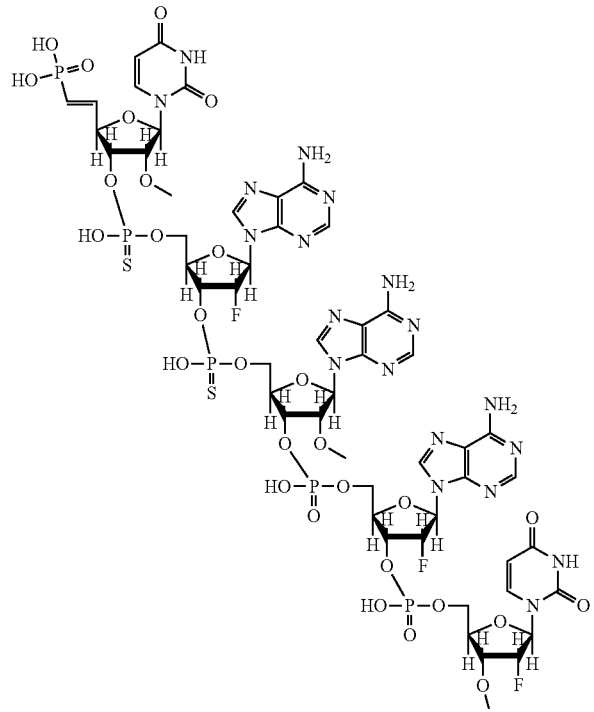
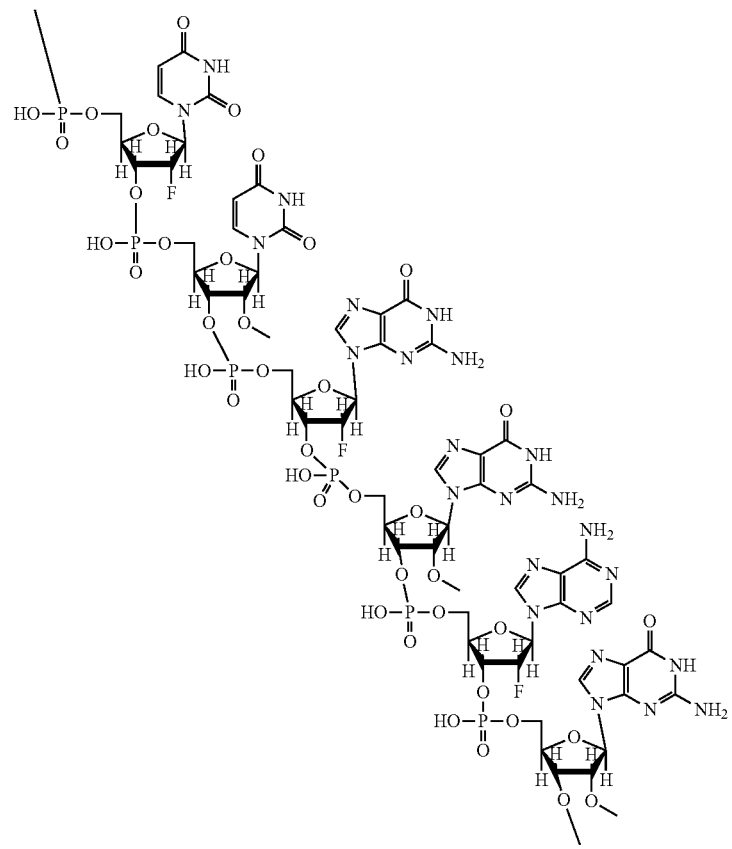

-continued
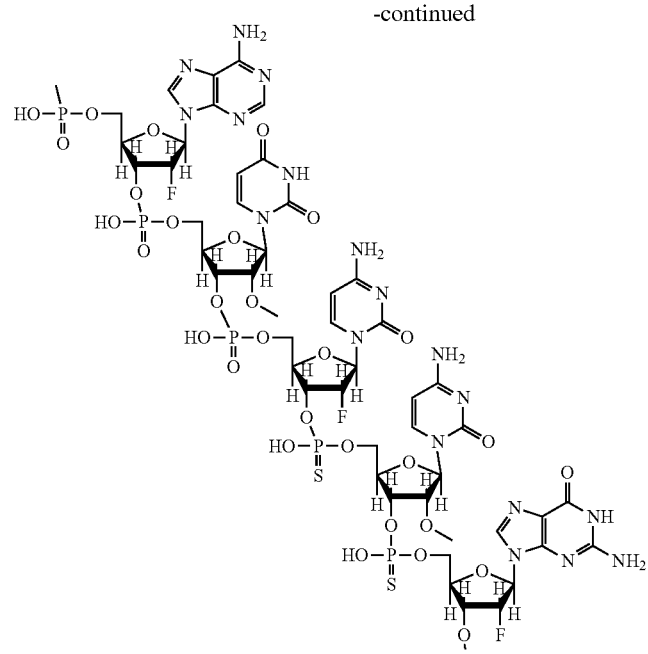
and
(2) the sense strand comprises Formula II (SEQ ID NO: 28), or a salt thereof:
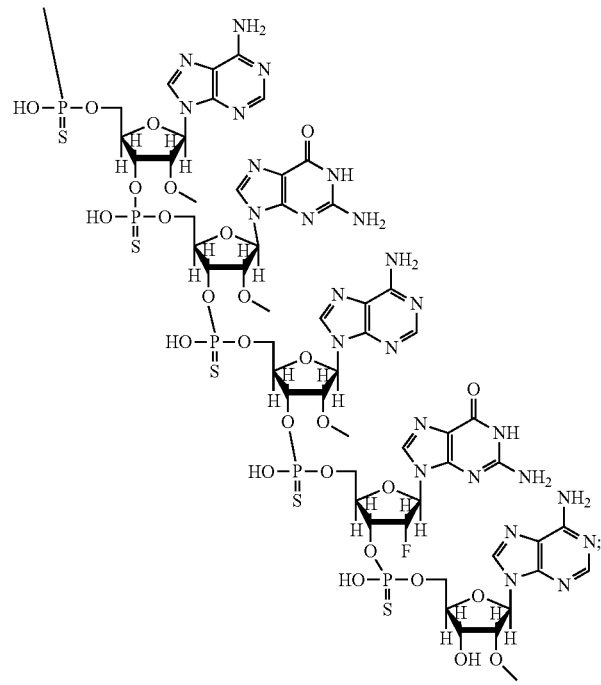

Formula II
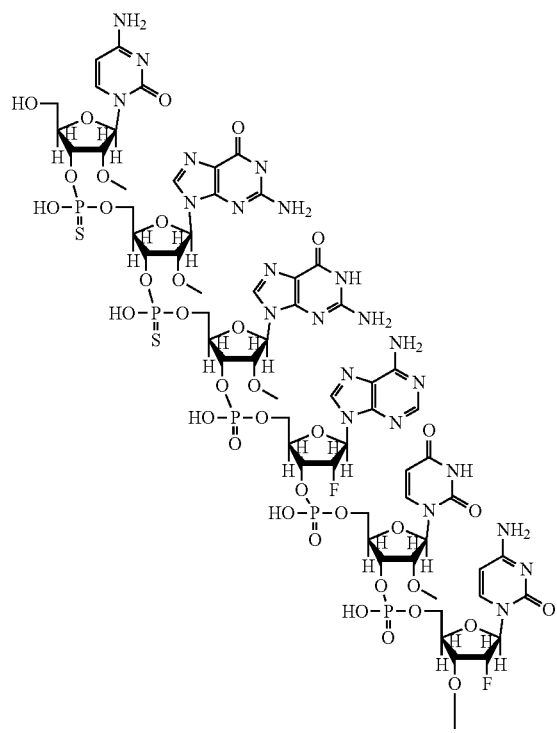
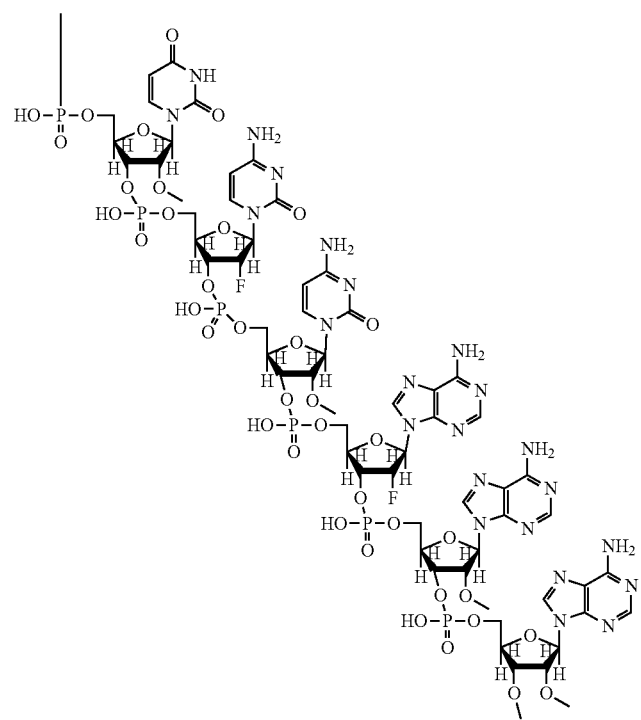

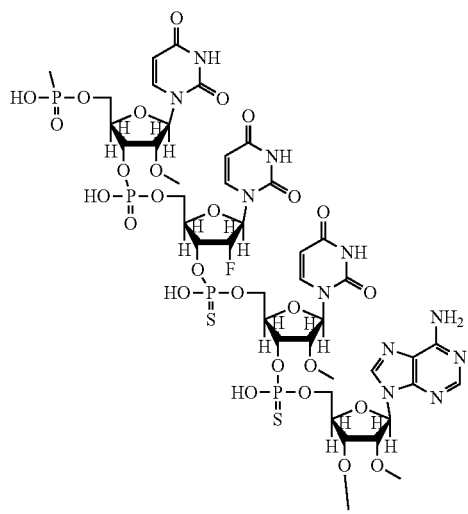
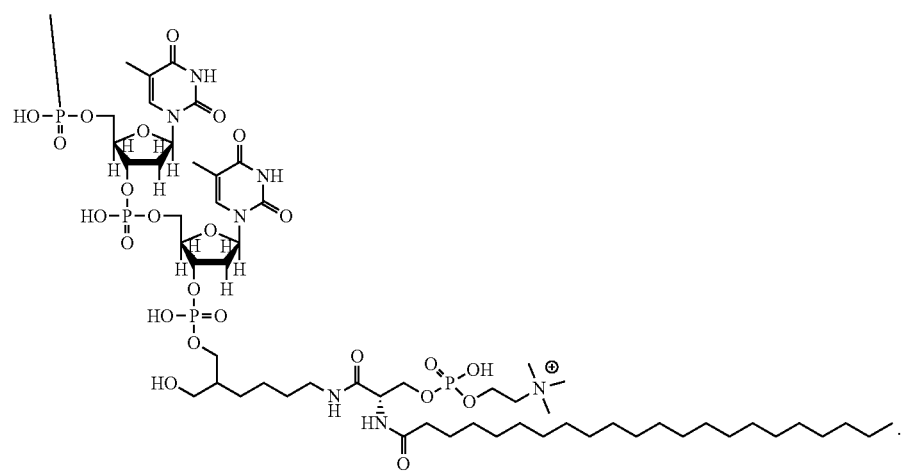
6. The dsRNA of claim 2, wherein:
(1) the antisense strand comprises Formula III (SEQ ID NO: 29), or a salt thereof:

Formula III
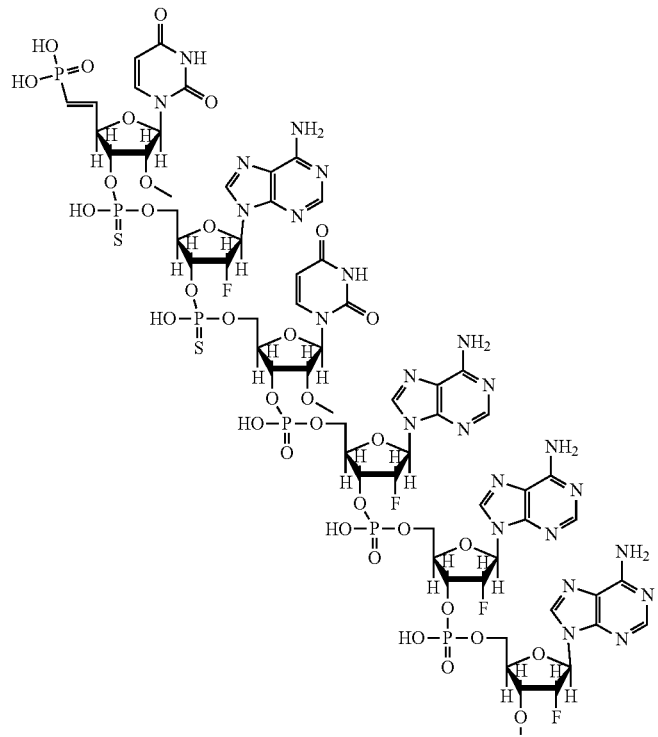
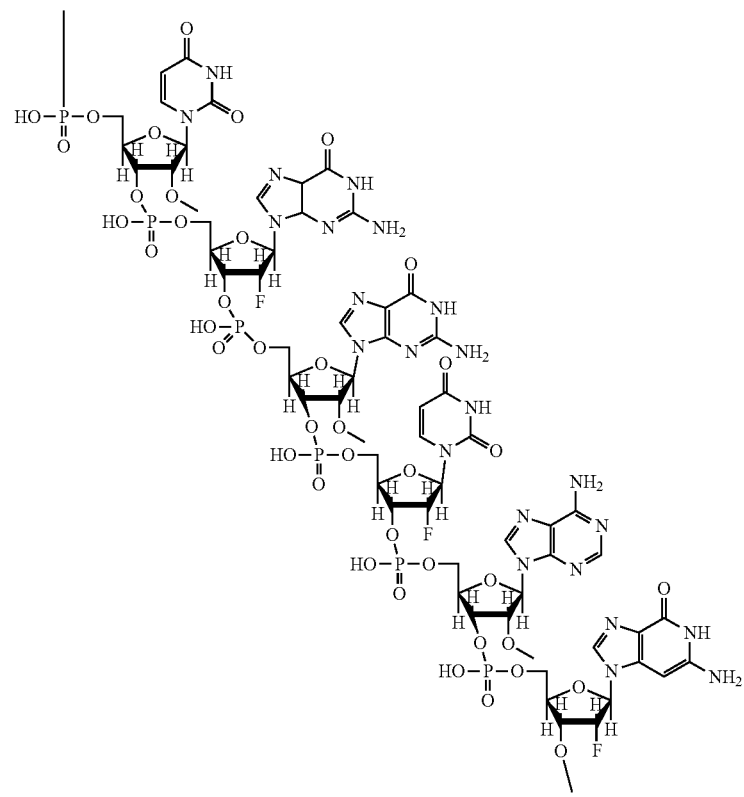

-continued
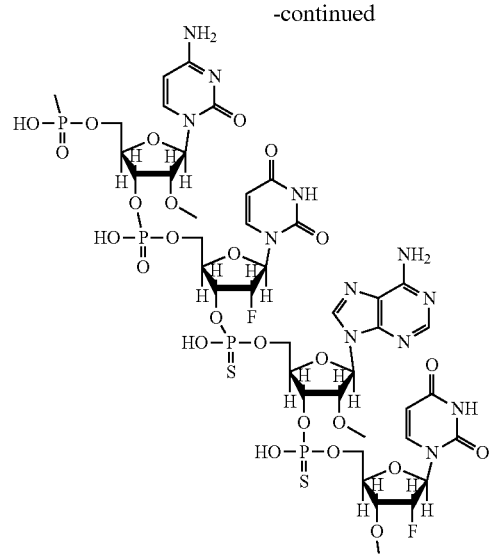
and
(2) the sense strand comprises Formula IV (SEQ ID NO: 30), or a salt thereof:
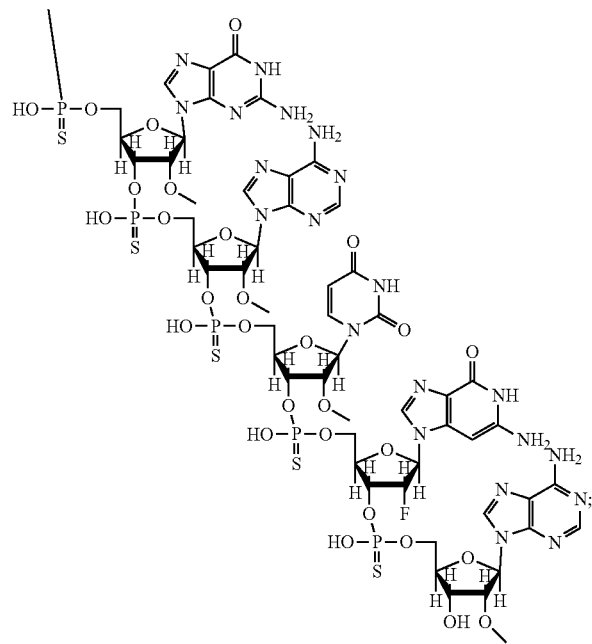

Formula IV
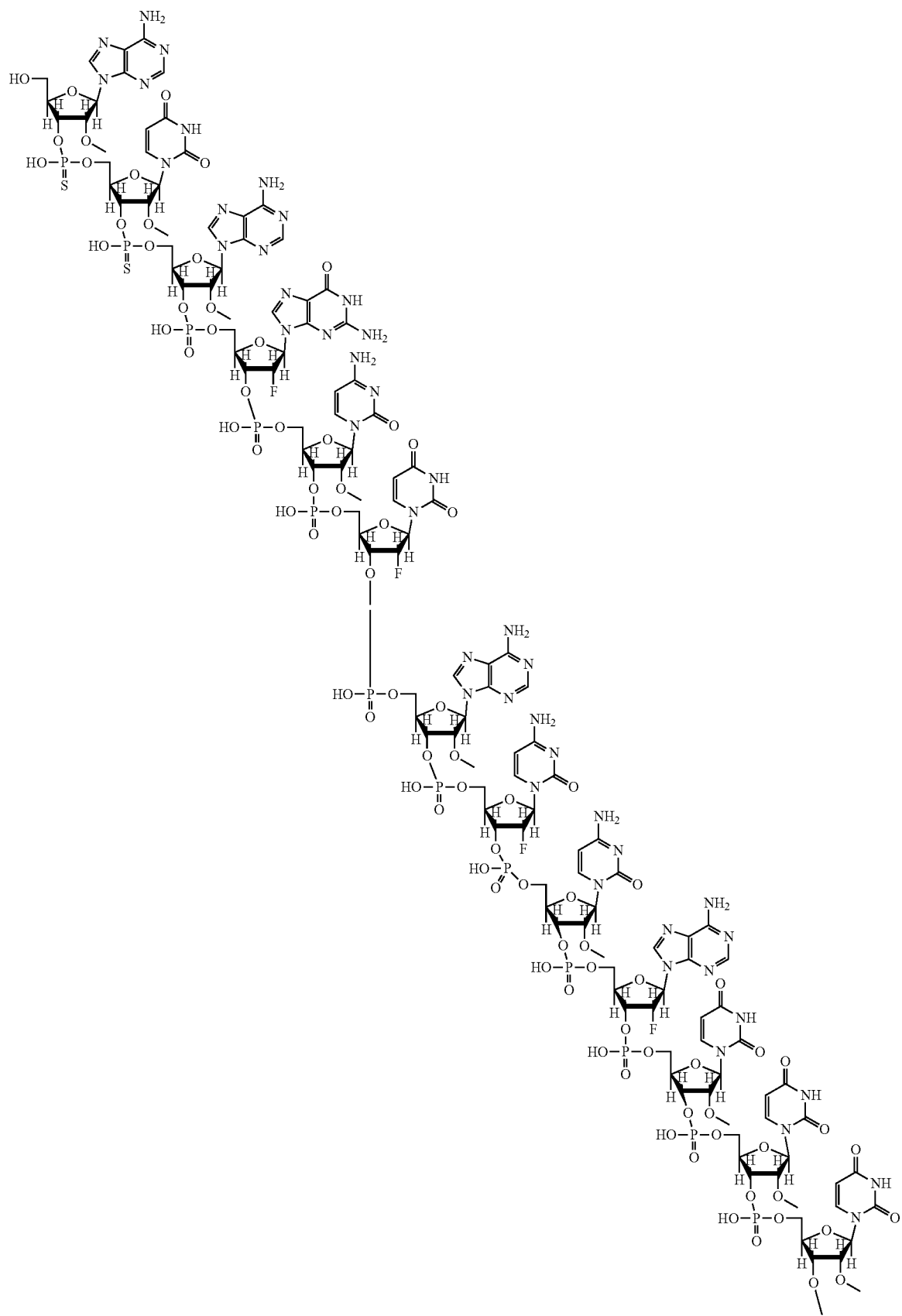

-continued

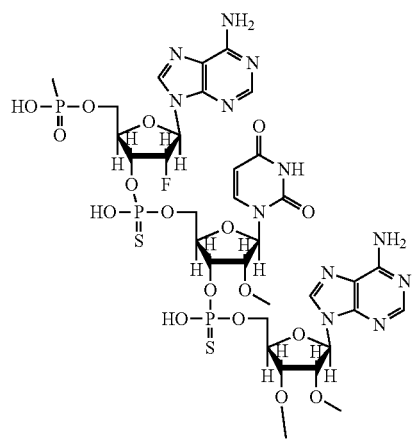

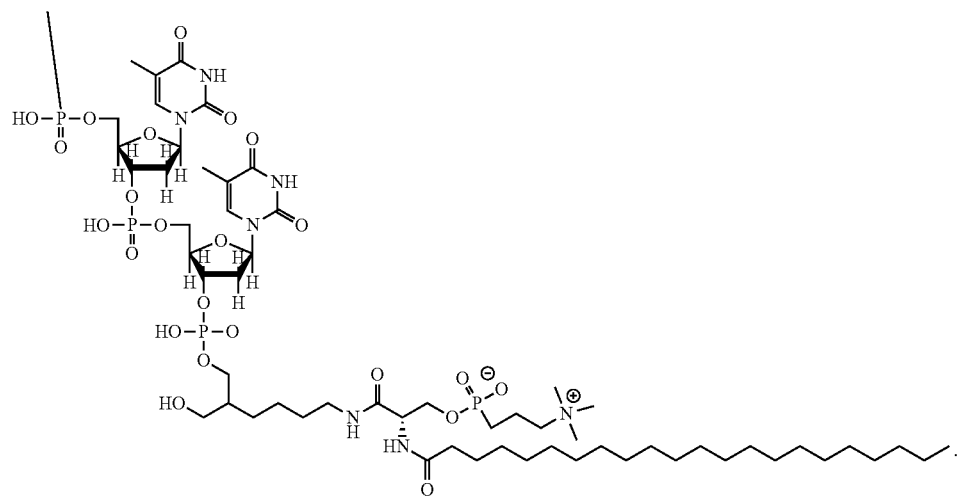

7. A pharmaceutical composition comprising:
a first dsRNA, said first dsRNA comprising an antisense strand and a sense strand, each strand with a 5' end and a 3' end, wherein:
(1) the antisense strand of the first dsRNA comprises V(mU)#(fA)#(mA)(fA)(fU)(fU)(mU)(fG)(mG)(fA) (mG)(fA)(mU)(fC)#(mC)#(fG)#(mA)#(mG) #(mA)# (fG)#(mA) (SEQ ID NO: 17) or a salt thereof; and
(2) the sense strand of the first dsRNA comprises (mC)# (mG)#(mG)(fA)(mU)(fC)(mU)(fC)(mC)(fA)(mA) (mA)(mU)(fU)#(mU)#(mA)(T)(T)-PCDCA (SEQ ID NO: 18) or a salt thereof; and
a second dsRNA, said second dsRNA comprising an antisense strand and a sense strand, each strand with a 5' end and a 3' end, wherein:
(1) the antisense strand of the second dsRNA comprises V(mU)#(fA)#(mU)(fA)(fA)(fA)(mU)(fG)(mG)(fU) (mA)(fG)(mC)(fU)#(mA)#(fU)#(mG)#(mA) #(mU)# (fG)#(mA) (SEQ ID NO: 19) or a salt thereof; and (2) the sense strand of the second dsRNA comprises (mA)#(mU)#(mA)(fG)(mC)(fU)(mA)(fC)(mC)(fA) (mU)(mU)(mU)(fA)#(mU)#(mA)(T)(T)-PCDCA (SEQ ID NO: 20) or a salt thereof,
wherein "m" corresponds to a 2'-O-methyl modification, "f" corresponds to a 2'-fluoro modification, "T" corresponds to a thymidine DNA nucleotide, "#" corresponds to a phosphorothioate internucleotide linkage, "V" corresponds to a 5'-vinylphosphonate, and "PCDCA" corresponds to a 3'-C7-phosphocholine-docosanoic acid conjugate through a phosphate linker.

8. A pharmaceutical composition comprising:
a first dsRNA, said first dsRNA comprising an antisense strand and a sense strand, each strand with a 5' end and a 3' end, wherein:
(1) the antisense strand of the first dsRNA comprises Formula I (SEQ ID NO: 27), or a salt thereof:

Formula I
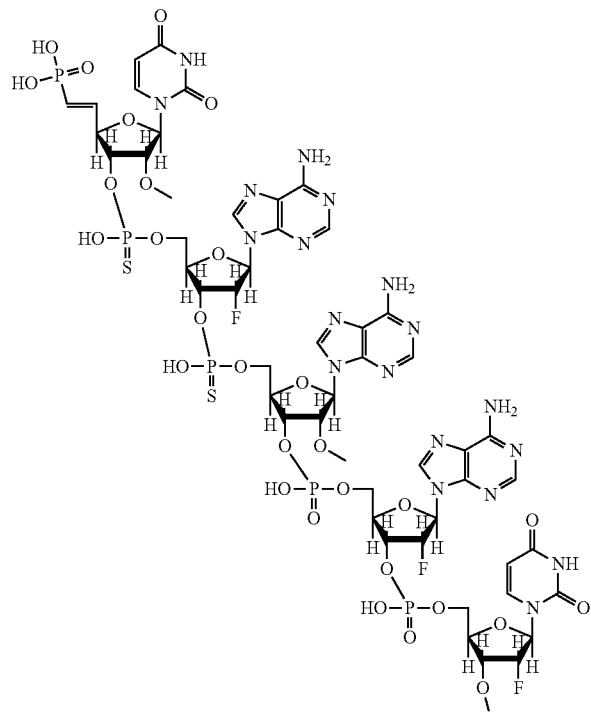
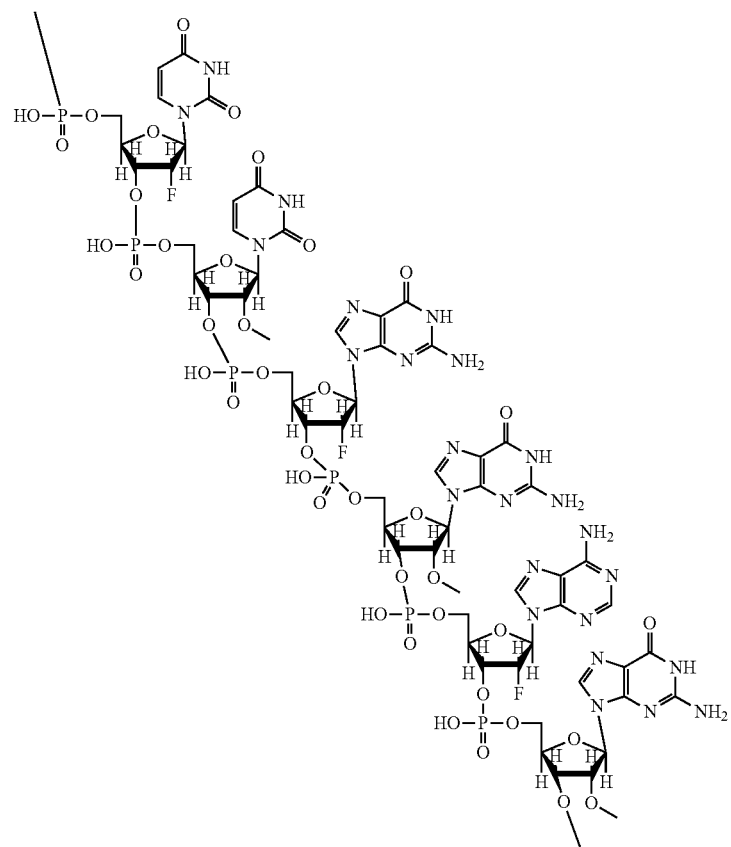

-continued
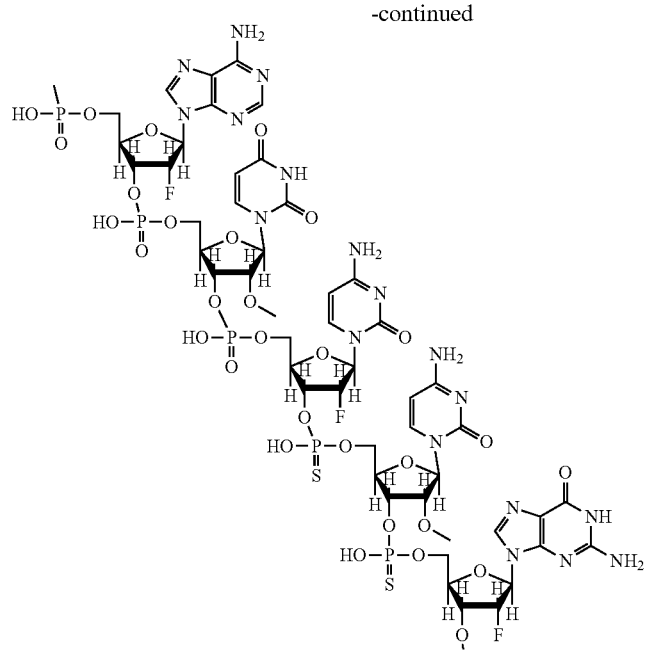
and
(2) the sense strand of the first dsRNA comprises Formula II (SEQ ID NO: 28), or a salt thereof:
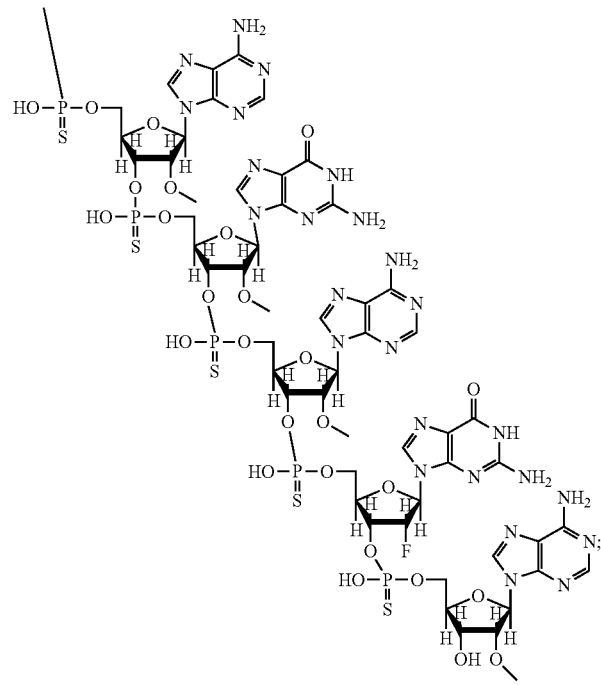

Formula II
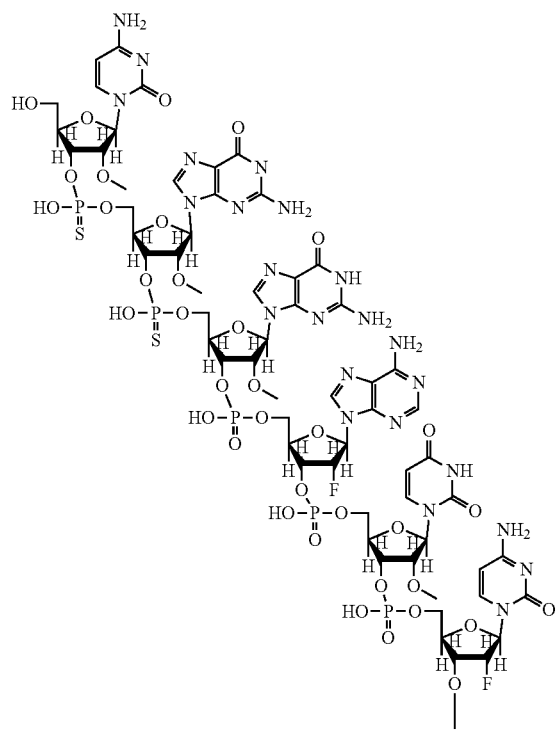
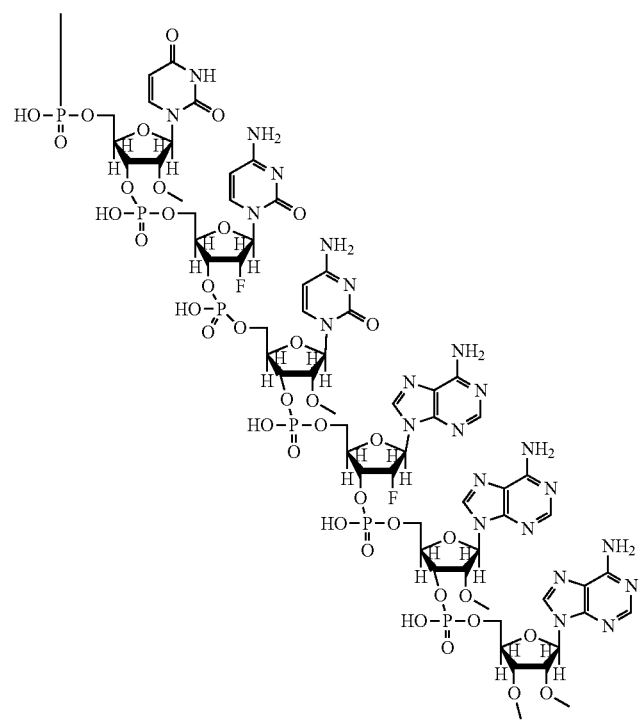

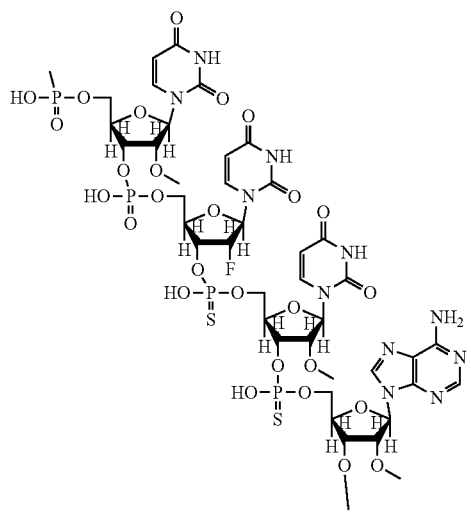
and
a second dsRNA, said second dsRNA comprising an antisense strand and a sense strand, each strand with a 5' end and a 3' end, wherein:
(1) the antisense strand of the second dsRNA comprises Formula III (SEQ ID NO: 29), or a salt thereof:
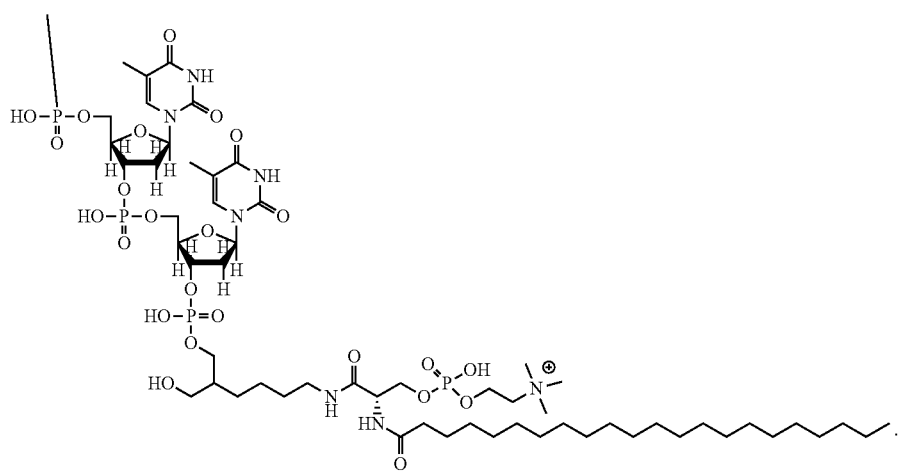

Formula III
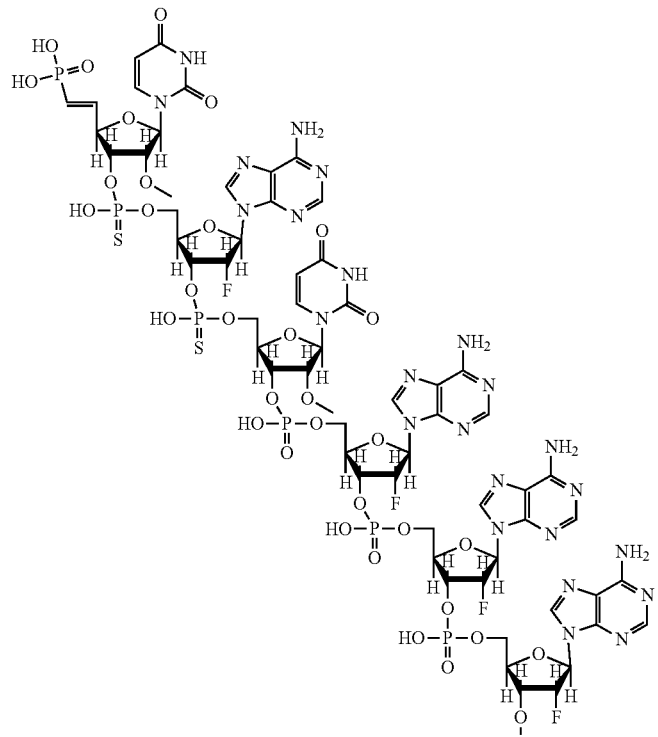
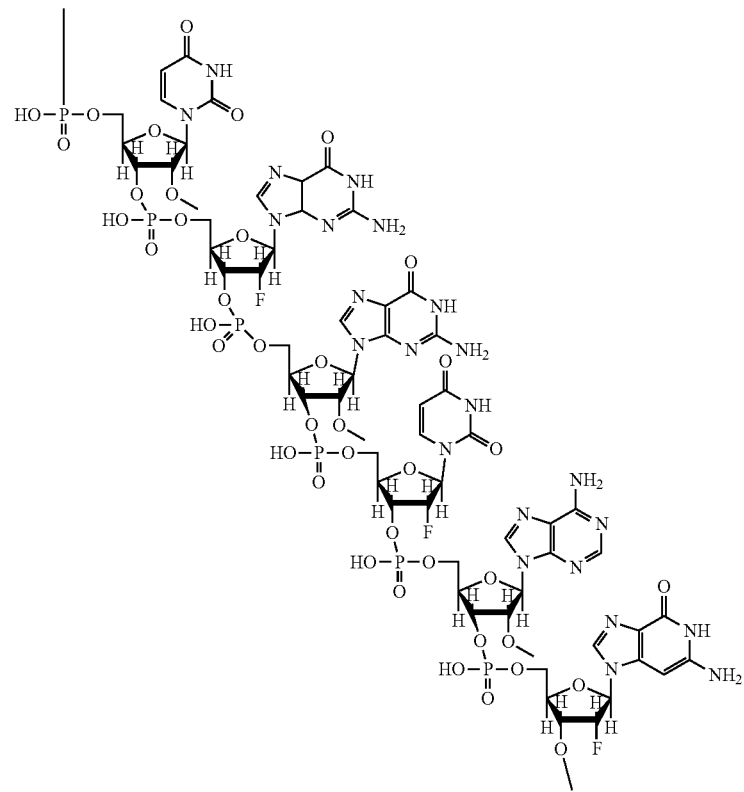

-continued
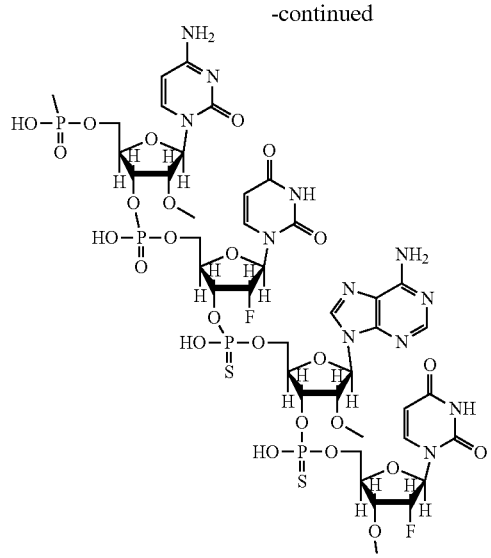
and
(2) the sense strand of the second dsRNA comprises Formula IV (SEQ ID NO: 30), or a salt thereof:
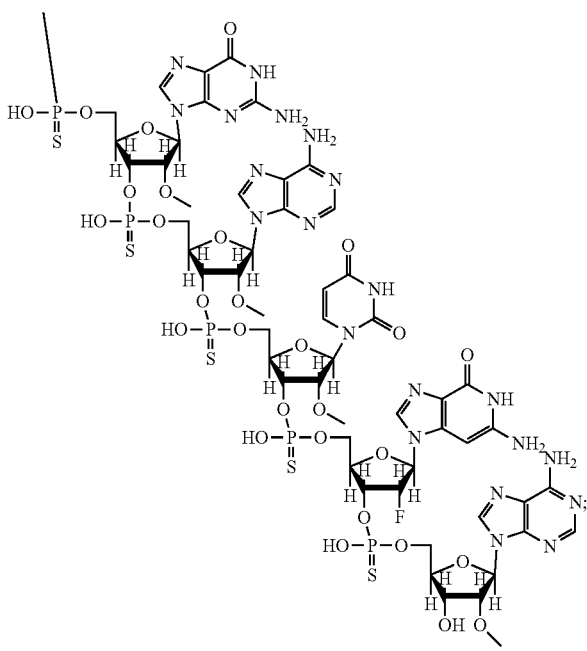

Formula IV
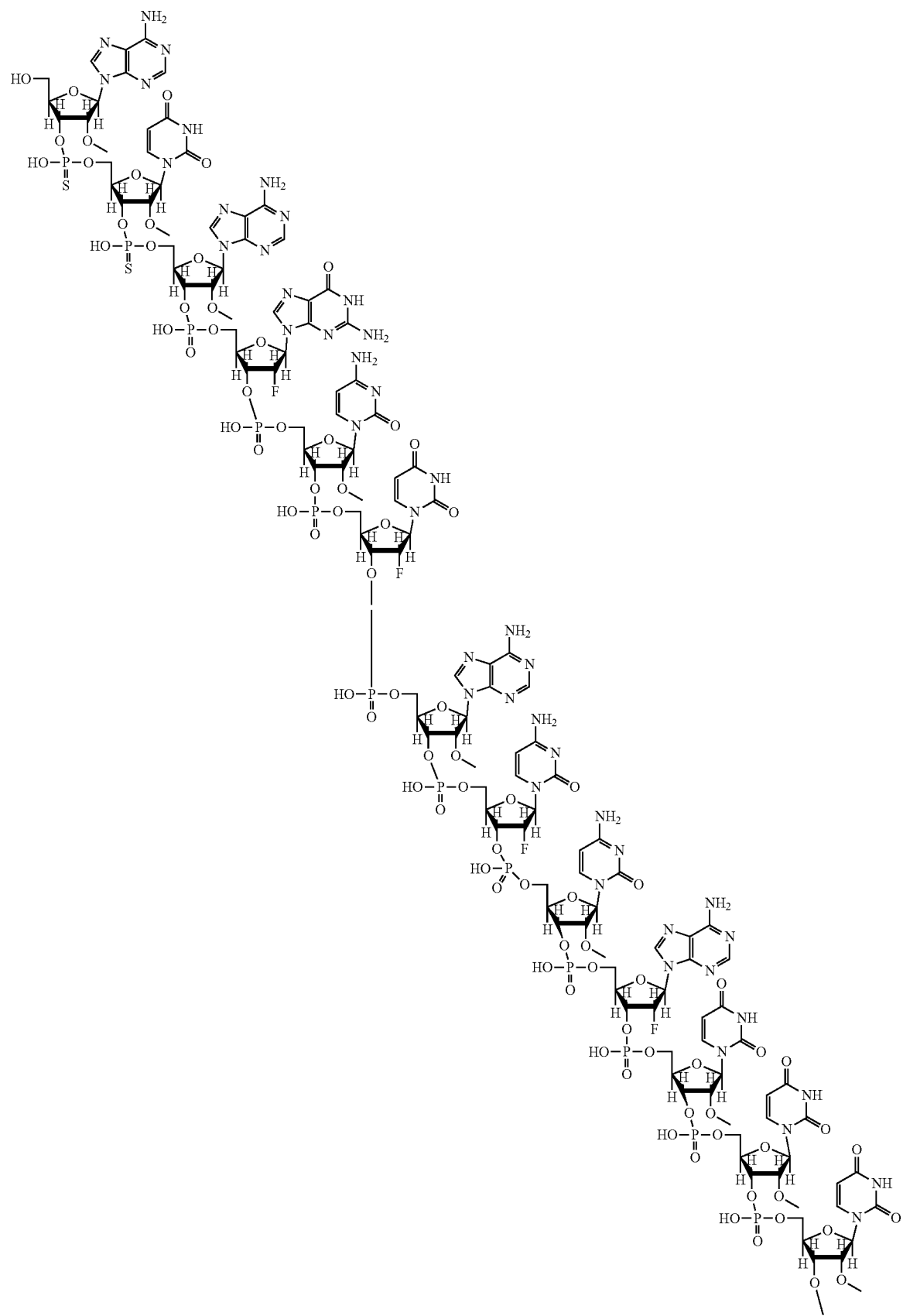

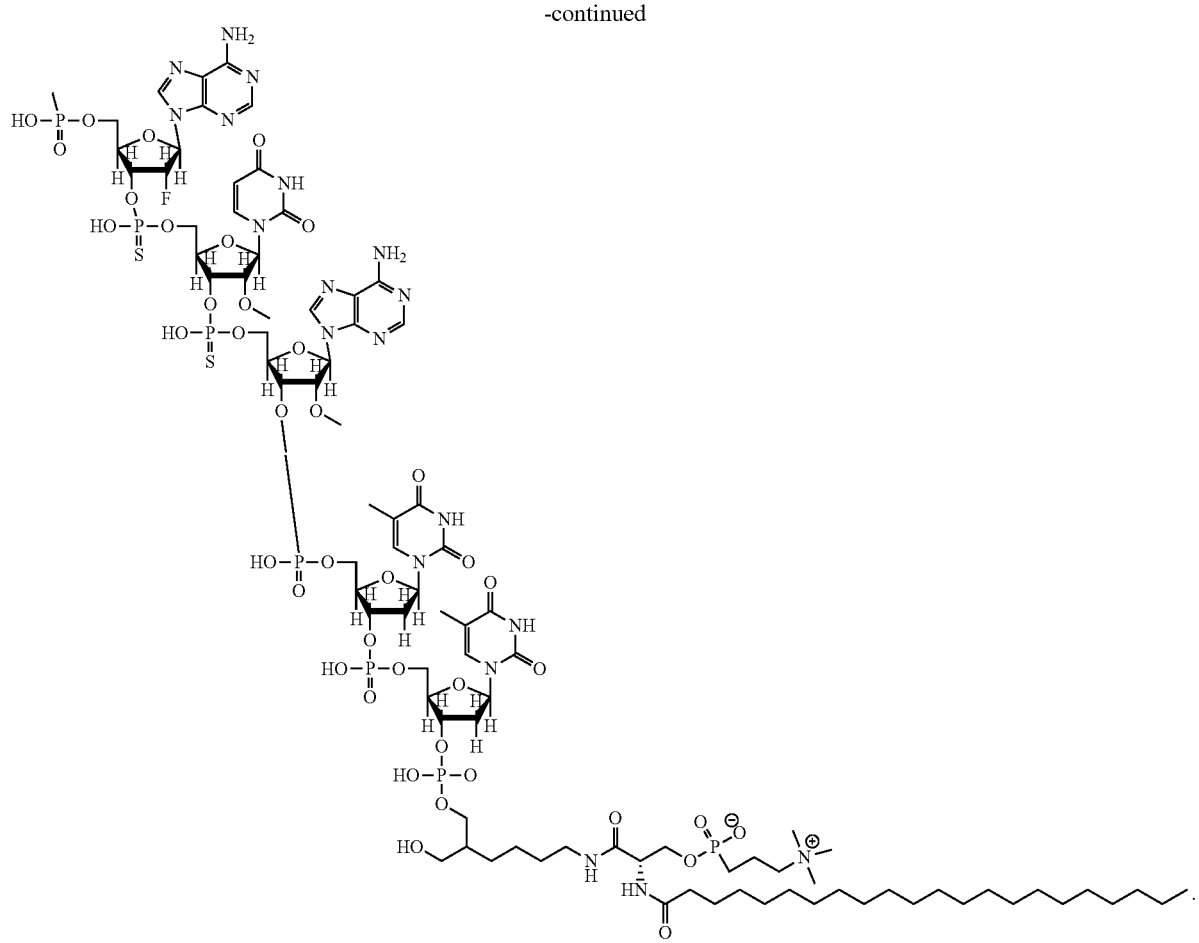

9. The dsRNA of claim 1, wherein a functional moiety is linked to the 3' end of the sense strand.

10. The dsRNA of claim 9, wherein the functional moiety is linked to the sense strand by a linker.

11. The dsRNA of claim 9, wherein the functional moiety comprises a hydrophobic moiety.

12. The dsRNA of claim 11, wherein the hydrophobic moiety is a fatty acid selected from the group consisting of Eicosapentaenoic acid (EPA), Docosahexaenoic acid (DHA) and Docosanoic acid (DCA).

13. The dsRNA of claim 10, wherein the linker comprises an ethylene glycol chain, an alkyl chain, a peptide, an RNA, a DNA, a phosphodiester, a phosphorothioate, a phosphoramidate, an amide, a carbamate, or a combination thereof.

14. The dsRNA of claim 10, wherein the linker is a cleavable linker.

15. The dsRNA of claim 14, wherein the cleavable linker comprises a dTdT dinucleotide with phosphodiester internucleotide linkages.

16. The dsRNA of claim 2, wherein a functional moiety is linked to the 3' end of the sense strand.

17. The dsRNA of claim 16, wherein the functional moiety is linked to the sense strand by a linker.

18. The dsRNA of claim 16, wherein the functional moiety comprises a hydrophobic moiety.

19. The dsRNA of claim 18, wherein the hydrophobic moiety is a fatty acid selected from the group consisting of Eicosapentaenoic acid (EPA), Docosahexaenoic acid (DHA) and Docosanoic acid (DCA).

20. The dsRNA of claim 17, wherein the linker comprises an ethylene glycol chain, an alkyl chain, a peptide, an RNA, a DNA, a phosphodiester, a phosphorothioate, a phosphoramidate, an amide, a carbamate, or a combination thereof.

21. The dsRNA of claim 17, wherein the linker is a cleavable linker.

22. The dsRNA of claim 21, wherein the cleavable linker comprises a dTdT dinucleotide with phosphodiester internucleotide linkages.

23. The dsRNA of claim 1, wherein the salt of SEQ ID NO: 12 or SEQ ID NO: 13 is a sodium salt or a potassium salt.

24. The dsRNA of claim 2, wherein the salt of SEQ ID NO: 15 or SEQ ID NO: 16 is a sodium salt or a potassium salt.

25. The dsRNA of claim 3, wherein the salt of SEQ ID NO: 17 or SEQ ID NO: 18 is a sodium salt or a potassium salt.

26. The dsRNA of claim 4, wherein the salt of SEQ ID NO: 19 or SEQ ID NO: 20 is a sodium salt or a potassium salt.

27. The dsRNA of claim 5, wherein the salt of Formula I or Formula II is a sodium salt or a potassium salt.

28. The dsRNA of claim 6, wherein the salt of Formula III or Formula IV is a sodium salt or a potassium salt.

29. The pharmaceutical composition of claim 7, wherein the salt of SEQ ID NO: 17, SEQ ID NO: 18, SEQ ID NO: 19, or SEQ ID NO: 20 is a sodium salt or a potassium salt.

30. The pharmaceutical composition of claim 8, wherein the salt of Formula I, Formula II, Formula III, or Formula IV is a sodium salt or a potassium salt.

\* \* \* \* \*

SEQUENCE LISTING

<160> NUMBER OF SEQ ID NOS: 30

<210> SEQ ID NO 1
<211> LENGTH: 20
<212> TYPE: DNA
<213> ORGANISM: Homo sapiens

<400> SEQUENCE: 1
ctctcggatc tccaaattta           20

<210> SEQ ID NO 2

```
<211> LENGTH: 20
<212> TYPE: DNA
<213> ORGANISM: Homo sapiens

<400> SEQUENCE: 2
catcatagct accatttatt                                              20

<210> SEQ ID NO 3

<400> SEQUENCE: 3

000

<210> SEQ ID NO 4

<400> SEQUENCE: 4

000

<210> SEQ ID NO 5
<211> LENGTH: 114
<212> TYPE: DNA
<213> ORGANISM: Homo sapiens

<400> SEQUENCE: 5
gtgagcactg caacaaaaag gctgttttct ctcggatctc caaatttaaa agcacaagga    60
atgattgtac cacacaaagt aatgtaaaac attaaaggac tcattaaaaa gtaa         114

<210> SEQ ID NO 6
<211> LENGTH: 456
<212> TYPE: DNA
<213> ORGANISM: Homo sapiens

<400> SEQUENCE: 6
gaagaaagaa attacaatca gaggtgagca ctgcaacaaa aaggctgttt tctctcggat    60
ctccaaattt aaaagcacaa ggaatgattg taccacacaa agtaatgtaa acattaaag   120 gactcattaa aaagtaacag ttgtctcata tcatcttgat ttattgtcac tgttgctaac  180
tttcaggctc ggaggagatg ctcctcccaa aatgagttcg gagatgatag cagtaataat  240 gagaccccg ggctccagct ctgggccccc cattcaggcc gaggggctg ctccgggggg    300 ccgacttggt gcacgtttgg atttggagga tccctgcact gccttctctg tgtttgttgc  360
tcttgctgtt ttctcctgcc tgataaacaa caacttggga tgatcctttc cattttgatg  420
ccaacctctt tttatttta agcggcgccc tatagt                              456

<210> SEQ ID NO 7
<211> LENGTH: 570
<212> TYPE: DNA
<213> ORGANISM: Homo sapiens

<400> SEQUENCE: 7
aactgtatac atcaacgtca ccatcgtcat cgtcatcatc accattgtca tcatcatcat    60
catcgtcatc atcatcatca tcatagctat catcattatc atcatcatca tcatcatcat   120
catagctacc atttattgaa aactattatg tgtcaacttc aaagaactta tcctttagtt   180
ggagagccaa gacaatcata acaataacaa atggccgggc atggtggctc acgcctgtaa   240
tcccagcact ttgggaggcc aaggcaggtg gatcatttga ggtcaggagt ccaagaccag   300
cctgaccaag atggtgaaat gctgtctcta ttaaaaatac aaaattagcc aggcatggtg   360
gctcatgcct gtaatgccag ctactcggga ggctgagaca ggagaatcac ttgaacccag   420
```

```
gaggcagagg ttgcagggag ccgagatcgt gtactgcact ccagcctggg caacaagagc    480
gaaactccgt ctcaaaaaac aaataaataa ataaataaat aaacagacaa aattcacttt    540
ttattctatt aaacttaaca tacatgctaa                                     570
```

<210> SEQ ID NO 8
<211> LENGTH: 21
<212> TYPE: RNA
<213> ORGANISM: Artificial Sequence
<220> FEATURE:
<223> OTHER INFORMATION: Synthetic oligonucleotide
<400> SEQUENCE: 8

```
uaaauuugga gauccgagag a                                              21
```

<210> SEQ ID NO 9
<211> LENGTH: 16
<212> TYPE: RNA
<213> ORGANISM: Artificial Sequence
<220> FEATURE:
<223> OTHER INFORMATION: Synthetic oligonucleotide
<400> SEQUENCE: 9

```
cggaucucca aauuua                                                    16
```

<210> SEQ ID NO 10
<211> LENGTH: 21
<212> TYPE: RNA
<213> ORGANISM: Artificial Sequence
<220> FEATURE:
<223> OTHER INFORMATION: Synthetic oligonucleotide
<400> SEQUENCE: 10

```
uauaaauggu agcuaugaug a                                              21
```

<210> SEQ ID NO 11
<211> LENGTH: 16
<212> TYPE: RNA
<213> ORGANISM: Artificial Sequence
<220> FEATURE:
<223> OTHER INFORMATION: Synthetic oligonucleotide
<400> SEQUENCE: 11

```
auagcuacca uuuaua                                                    16
```

<210> SEQ ID NO 12
<211> LENGTH: 21
<212> TYPE: RNA
<213> ORGANISM: Artificial Sequence
<220> FEATURE:
<223> OTHER INFORMATION: Synthetic oligonucleotide
<400> SEQUENCE: 12

```
uaaauuugga gauccgagag a                                              21
```

<210> SEQ ID NO 13
<211> LENGTH: 16
<212> TYPE: RNA
<213> ORGANISM: Artificial Sequence
<220> FEATURE:
<223> OTHER INFORMATION: Synthetic oligonucleotide
<400> SEQUENCE: 13

```
cggaucucca aauuua                                                    16
```

<210> SEQ ID NO 14
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 14
uauaaauggu agcuaugaug a                                              21

<210> SEQ ID NO 15
<211> LENGTH: 16
<212> TYPE: RNA
<213> ORGANISM: Artificial Sequence
<220> FEATURE:
<223> OTHER INFORMATION: Synthetic oligonucleotide

<400> SEQUENCE: 15
auagcuacca uuuaua                                                    16

<210> SEQ ID NO 16
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 16
uauaaauggu agcuaugaug a                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 17
uaaauuugga gauccgagag a                                              21

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
cggaucucca aauuuatt                                                  18

<210> SEQ ID NO 19
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 19
uauaaauggu agcuaugaug a                                              21

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

```
<400> SEQUENCE: 20
auagcuacca uuuauatt                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 21
cggaucucca aauuuatt                                                 18

<210> SEQ ID NO 22
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 22
uaaauuugga gauccgagag a                                             21

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
auagcuacca uuuauatt                                                 18

<210> SEQ ID NO 24
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 24
uauaaauggu agcuaugaug a                                             21

<210> SEQ ID NO 25
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 25
uauaaauggu agcuaugaug a                                             21

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 26
auagcuacca uuuauatt                                                 18

<210> SEQ ID NO 27
```

```
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 27
uaaauuugga gauccgagag a                                              21

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
cggaucucca aauuuatt                                                  18

<210> SEQ ID NO 29
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 29
uauaaauggu agcuaugaug a                                              21

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 30
auagcuacca uuuauatt                                                  18
```